(12) United States Patent
Gravestock et al.

(10) Patent No.: US 7,498,350 B2
(45) Date of Patent: Mar. 3, 2009

(54) OXAZOLIDINONES AS ANTIBACTERIAL AGENTS

(75) Inventors: Michael Barry Gravestock, Waltham, MA (US); Neil James Hales, Macclesfield (GB); Folkert Reck, Waltham, MA (US); Fei Zhou, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 543 days.

(21) Appl. No.: 10/536,687

(22) PCT Filed: Nov. 24, 2003

(86) PCT No.: PCT/GB03/05091

§ 371 (c)(1),
(2), (4) Date: May 27, 2005

(87) PCT Pub. No.: WO2004/048350

PCT Pub. Date: Jun. 10, 2004

(65) Prior Publication Data

US 2006/0116386 A1    Jun. 1, 2006

(30) Foreign Application Priority Data

Nov. 28, 2002  (GB)  .................. 0227704.4
May 10, 2003  (GB)  .................. 0310828.9

(51) Int. Cl.
*A61K 31/44*  (2006.01)
*C07D 413/00*  (2006.01)
(52) U.S. Cl. .................. 514/340; 546/271.4
(58) Field of Classification Search .............. 546/271.4; 514/357, 340
See application file for complete search history.

(56) References Cited

U.S. PATENT DOCUMENTS

2002/0115669 A1    8/2002    Pilushchev et al.

FOREIGN PATENT DOCUMENTS

| WO | WO 01/81350 | 11/2001 |
|---|---|---|
| WO | WO 01/94342 | 12/2001 |
| WO | WO 02/081470 | 10/2002 |
| WO | WO 03/022824 | 3/2003 |
| WO | WO 03/035648 | 5/2003 |
| WO | WO 03/072575 | 9/2003 |
| WO | WO 03/072576 | 9/2003 |
| WO | WO 2004/048370 | 6/2004 |
| WO | WO 2004/048392 | 6/2004 |

OTHER PUBLICATIONS

Hcaplus 53:2071f-i.*
Rondstedt, Christian S., Jr. et al.: "Unsaturated sulfonic acids. V." Journal of the American Chemical Society, vol. 77, 1955, pp. 6532-6540, XP002290054.

* cited by examiner

*Primary Examiner*—Janet L Andres
*Assistant Examiner*—Binta M Robinson
(74) *Attorney, Agent, or Firm*—Morgan, Lewis & Bockius LLP

(57) ABSTRACT

A compound of the formula (I), or a pharmaceutically-acceptable salt, or in-vivo hydrolysable ester thereof: Wherein C is selected from (D) and (E), $R_2a$, $R_6a$, and $R_3a$ are independently selected from for example H, $CF_3$, Me and Et; $R_2b$ and $R6b$ are independently selected from for example H, F, $CF_3$, Me and Et; $R_1b$ is for example optionally substituted diazolyl, triazolyl or tetrazolyl; $R_4$ is for example an optionally substituted 5- or 6-membered heterocyclic ring system. Methods for making compounds of the formula (I), compositions containing them and their use as antibacterial agents are also described.

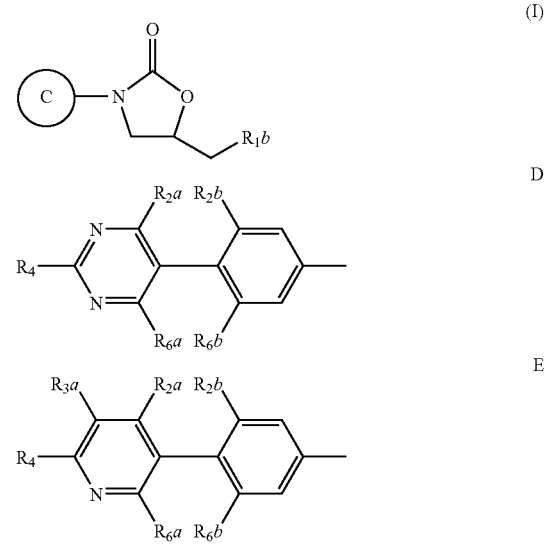

15 Claims, No Drawings

OXAZOLIDINONES AS ANTIBACTERIAL AGENTS

CROSS-REFERENCE TO RELATED APPLICATIONS

This application is a US National Stage under 35 U.S.C § 371 of International Application No. PCT/GB2003/005091 (filed Nov. 24, 2003) which claims priority under 35 U.S.C. § 119(a)-(d) to Application No. GB 0310828.9 filed on May 10, 2003 and GB 0227704.4 filed Nov. 28, 2002, the specification of which is incorporated by reference herein.

The present invention relates to antibiotic compounds and in particular to antibiotic compounds containing substituted oxazolidinone rings. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant staphylococcus (MRSA), methicillin resistant coagulase negative staphylococci (MRCNS), penicillin resistant Streptococcus pneumoniae and multiply resistant Enterococcus faecium.

The major clinically effective antibiotic for treatment of such resistant Grain-positive pathogens is vancomycin. Vancomycin is a glycopeptide and is associated with various toxicities including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including H. influenzae and M. catarrhalis.

Certain antibacterial compounds containing an oxazolidinone ring have been described in the art (for example, Walter A. Gregory et al in J. Med. Chem. 1990, 33, 2569-2578 and 1989, 32(8), 1673-81; Chung-Ho Park et al in J. Med. Chem. 1992, 35, 1156-1165). Bacterial resistance to known antibacterial agents may develop, for example, by (i) the evolution of active binding sites in the bacteria rendering a previously active pharmacophore less effective or redundant, and/or (ii) the evolution of means to chemically deactivate a given pharmacophore, and/or (iii) the evolution of efflux pathways. Therefore, there remains an ongoing need to find new antibacterial agents with a favourable pharmacological profile, in particular for compounds containing new, more potent, pharmacophores.

Accordingly the present invention provides a compound of the formula (I), or a pharmaceutically-acceptable salt, or an in-vivo-hydrolysable ester thereof,

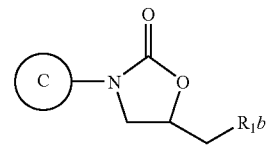

(I)

wherein group C is selected from groups D and E,

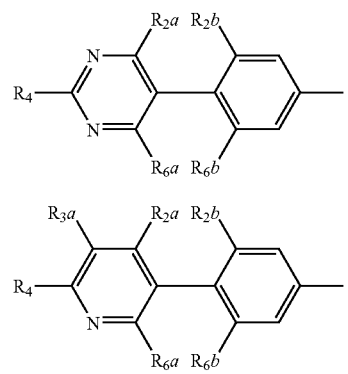

wherein in D and E the phenyl ring is attached to the oxazolidinone in (I); $R_1b$ is HET1 or HET2, wherein i) HET1 is an N-linked 5-membered, fully or partially unsaturated heterocyclic ring, containing either (i) 1 to 3 further nitrogen heteroatoms or (ii) a further heteroatom selected from O and S together with an optional further nitrogen hetero atom; which ring is optionally substituted on a C atom, other than a C atom adjacent to the linking N atom, by an oxo or thioxo group; and/or which ring is optionally substituted on any available C atom, other than a C atom adjacent to the linking N atom, by a substituent selected from RT as hereinafter defined and/or on an available nitrogen atom, other than a N atom adjacent to the linking N atom, (provided that the ring is not thereby quaternised) by (1-4C)alkyl;

ii) HET2 is an N-linked 6-membered di-hydro-heteroaryl ring containing up to three nitrogen heteroatoms in total (including the linking heteroatom), which ring is substituted on a suitable C atom, other than a C atom adjacent to the lining N atom, by oxo or thioxo and/or which ring is optionally substituted on any available C atom, other than a C atom adjacent to the linking N atom, by one or two substituents independently selected from RT as hereinafter defined and/or on an available nitrogen atom, other than a N atom adjacent to the linking N atom, (provided that the ring is not thereby quaternised) by (1-4C)alkyl;

RT is selected from a substituent from the group:

(RTa1) hydrogen, halogen, (1-4C)alkoxy, (2-4C)alkenyloxy, (2-4C)alkenyl, (2-4C)alkynyl, (3-6C)cycloalkyl, (3-6C)cycloalkenyl, (1-4C)alkylthio, amino, azido, cyano and nitro; or (RTa2) (1-4C)alkylamino, di-(1-4C)alkylamino, and (2-4C)alkenylamino;

or RT is selected from the group (RTb1) (1-4C)alkyl group which is optionally substituted by one substituent selected from hydroxy, (1-4C)alkoxy, (1-4C)alkylthio, cyano and azido; or (RTb2) (1-4C)alkyl group which is optionally substituted by one substituent selected from (2-4C)alkenyloxy, (3-6C)cycloalkyl, and (3-6C)cycloalkenyl;

or RT is selected from the group (RTc) a fully saturated 4-membered monocyclic ring containing 1 or 2 heteroatoms independently selected from O, N and S (optionally oxidised), and linked via a ring nitrogen or carbon atom;

and wherein at each occurrence of an RT substituent containing an alkyl, alkenyl, alkynyl, cycloalkyl or cycloalkenyl moiety in (RTa1) or (RTa2), (RTb1) or (RTb2), or (RTc) each such moiety is optionally substituted on an available carbon atom with one, two, three or more substituents independently selected from F, Cl, Br, OH and CN;

$R_2a$ and $R_6a$ are independently selected from H, $CF_3$, OMe, SMe, Me and Et;

$R_2b$ and $R_6b$ are independently selected from H, F, Cl, $CF_3$, OMe, SMe, Me and Et;

$R_3a$ is selected from H, (1-4C)alkyl, cyano, Br, F, Cl, OH, (1-4C)alkoxy, —S(O)$_n$(1-4C)alkyl (wherein n=0, 1, or 2), amino, (1-4C)alkylcarbonylamino, nitro, —CHO, —CO(1-4C)alkyl, —CONH$_2$ and —CONH(1-4C)alkyl;

$R_4$ is selected from $R_4a$ and $R_4b$ wherein $R_4a$ is selected from azido, —NR$_7$R$_8$, OR$_{10}$, (1-4C)alkyl, (1-4C)alkoxy, (3-6C)cycloalkyl, —(CH$_2$)$_k$—R$_9$, AR1, AR2, (1-4C)alkanoyl, —CS(1-4C)alkyl, —C(=W)NRvRw [wherein W is O or S, Rv and Rw are independently H, or (1-4C)alkyl], —(C=O)$_1$—R$_6$, —COO(1-4C)alkyl, —C=OAR1, —C=OAR2, —COOAR1, S(O)n(1-4C)alkyl (wherein n=1 or 2), —S(O)pAR1, —S(O)pAR2 and —C(=S)O(1-4C)alkyl; wherein any (1-4C)alkyl chain may be optionally substituted by (1-4C)alkyl, cyano, hydroxy or halo; p=0, 1 or 2;

$R_4b$ is selected from HET-3;

$R_6$ is selected from hydrogen, (1-4C)alkoxy, amino, (1-4C)alkylamino and hydroxy(1-4C)alkylamino;

k is 1 or 2;

l is 1 or 2;

$R_7$ and $R_8$ are independently selected from H and (1-4C)alkyl, or wherein $R_7$ and $R_8$ taken together with the nitrogen to which they are attached can form a 5-7 membered ring optionally with an additional heteroatom selected from N, O, S(O)n (wherein n=1 or 2) in place of 1 carbon atom of the so formed ring; wherein the ring may be optionally substituted by one or two groups independently selected from (1-4C)alkyl, (3-6C)cycloalkyl, (1-4C)alkanoyl, —COO(1-4C)alkyl, —S(O)n(1-4C)alkyl (wherein n=1 or 2), AR1, AR2, —C=OAR1, —C=OAR2, —COOAR1, —CS(1-4C)alkyl, —C(=S)O(1-4C)alkyl, —C(=W)NRvRw [wherein W is O or S, Rv and Rw are independently H, or (1-4C)alkyl], —S(O)pAR1 and —S(O)pAR2; wherein any (1-4C)alkyl, (3-6C)cycloalkyl or (1-4C)alkanoyl group may be optionally substituted (except on a carbon atom adjacent to a heteroatom) by one or two substituents selected from (1-4C)alkyl, cyano, hydroxy, halo, amino, (1-4C)alkylamino and di(1-4C)alkylamino; p=0, 1 or 2;

$R_9$ is independently selected from $R_9a$ to $R_9d$ below:

$R_9a$: AR1, AR2, AR2a, AR2b, AR3, AR3a, AR3b, AR4, AR4a, CY1, CY2;

$R_9b$: cyano, carboxy, (1-4C)alkoxycarbonyl, —C(=W)NRvRw [wherein W is O or S, Rv and Rw are independently H, or (1-4C)alkyl and wherein Rv and Rw taken together with the amide or thioamide nitrogen to which they are attached can form a 5-7 membered ring optionally with an additional heteroatom selected from N, O, S(O)n in place of 1 carbon atom of the so formed ring; wherein when said ring is a piperazine ring, the ring may be optionally substituted on the additional nitrogen by a group selected from (1-4C)alkyl, (3-6C)cycloalkyl, (1-4C)alkanoyl, —COO(1-4C)alkyl, —S(O)n(1-4C)alkyl (wherein n=1 or 2), —COOAR1, —CS(1-4C)alkyl and —C(=S)O(1-4C)alkyl; wherein any (1-4C)alkyl, (3-6C)cycloalkyl or (1-4C)alkanoyl group may itself optionally be substituted by cyano, hydroxy or halo)], ethenyl, 2-(1-4C)alkylethenyl, 2-cyanoethenyl, 2-cyano-2-((1-4C)alkyl)ethenyl, 2-nitroethenyl, 2-nitro-2-((1-4C)alkyl)ethenyl, 2-((1-4C)alkylaminocarbonyl)ethenyl, 2-((1-4C)alkoxycarbonyl)ethenyl, 2-(AR1)ethenyl, 2-(AR2)ethenyl, 2-(AR2a)ethenyl;

$R_9c$: (1-6C)alkyl

{optionally substituted by one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkylcarbonyl, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], and amino; and/or optionally substituted by one group selected from carboxy, phosphonate [phosphono, —P(O)(OH)$_2$, and mono- and di-(1-4C)alkoxy derivatives thereof], phosphinate [—P(OH)$_2$ and mono- and di-(1-4C)alkoxy derivatives thereof], cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino-, (1-4C)alkoxycarbonylamino-, N-(1-4C)alkyl-N-(1-6C)alkanoylamino-, —C(=W)NRvRw [wherein W is O or S, Rv and Rw are as hereinbefore defined], (=NORv) wherein Rv is as hereinbefore defined, (1-4C)alkylS(O)$_p$NH, (1-4C)alkylS(O)$_p$-((1-4C)alkyl)N—, fluoro(1-4C)alkylS(O)$_p$NH—, fluoro(1-4C)alkylS(O)$_p$((1-4C)alkyl)N—, (1-4C)alkylS(O)$_q$—, CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups}; wherein any (1-4C)alkyl present in any substituent on $R_9c$ may itself be substituted by one or two groups independently selected from cyano, hydroxy, halo, amino, (1-4C)alkylamino and di(1-4C)alkylamino, provided that such a substituent is not on a carbon adjacent to a heteroatom atom if present;

$R_9d$: $R_{14}$C(O)O(1-6C)alkyl- wherein $R_{14}$ is AR1, AR2, (1-4C)alkylamino, benzyloxy-(1-4C)alkyl or (1-10C)alkyl {optionally substituted as defined for ($R_9c$)}; $R_{10}$ is selected from hydrogen, $R_9c$ (as hereinbefore defined), (1-4C)acyl and (1-4C)alkylsulfonyl;

HET-3 is selected from:

a) a 5-membered heterocyclic ring containing at least one nitrogen and/or oxygen in which any carbon atom is a C=O, C=N, or C=S group, wherein said ring is of the formula HET3-A to HET3-E below:

HET3-A
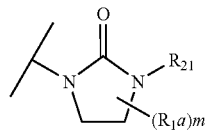
HET3-B
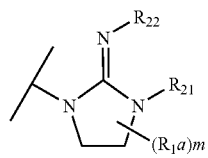
HET3-C
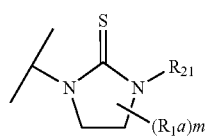
HET3-D
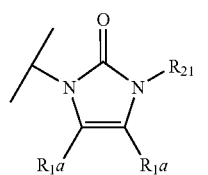
HET3-E
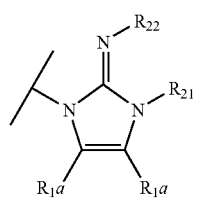
b) a carbon-linked 5- or 6-membered heteroaromatic ring containing 1, 2, 3, or 4 heteroatoms independently selected from N, O and S selected from HET3-F to HET3-Y below:
HET3-F
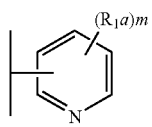
HET3-G
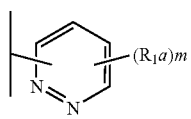
HET3-H
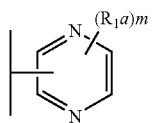
HET3-I
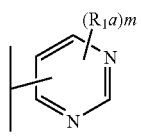
HET3-J
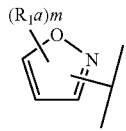
HET3-K
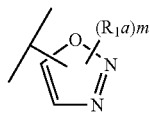
HET3-L
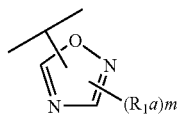
HET3-M
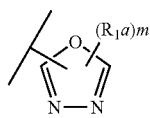
HET3-N
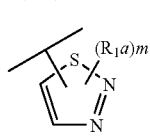
HET3-O
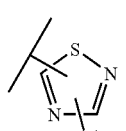
HET3-P
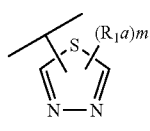
HET3-Q
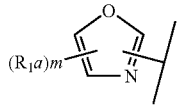
HET3-R
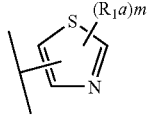
HET3-S
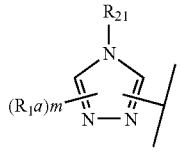
HET3-T
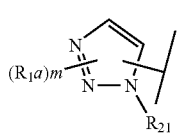

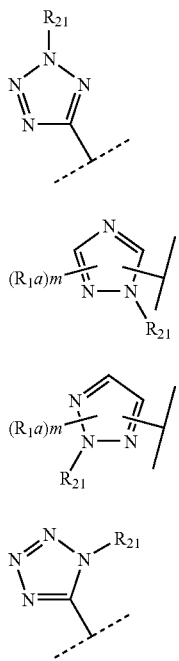
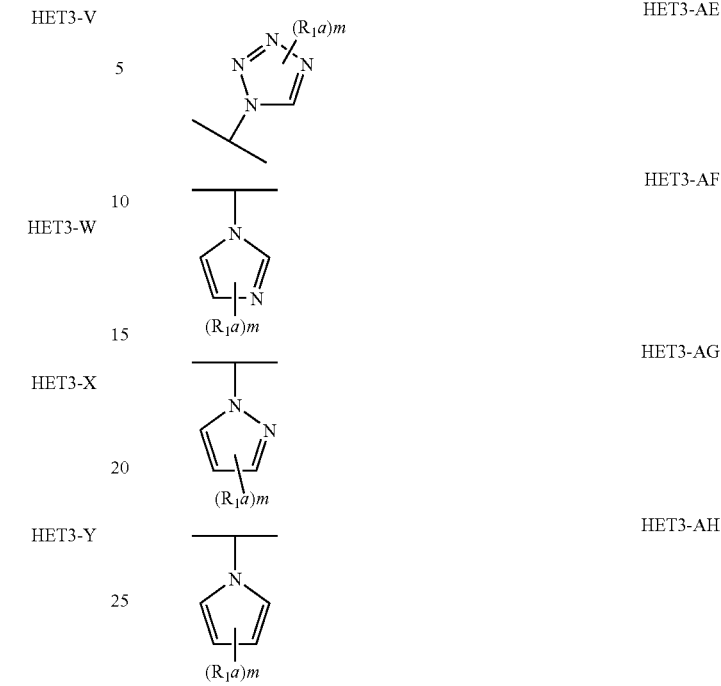

c) a nitrogen-linked 5- or 6-membered heteroaromatic ring containing 1, 2, 3, or 4 heteroatoms independently selected from N, O and S selected from HET3-Z to HET3-AH below:

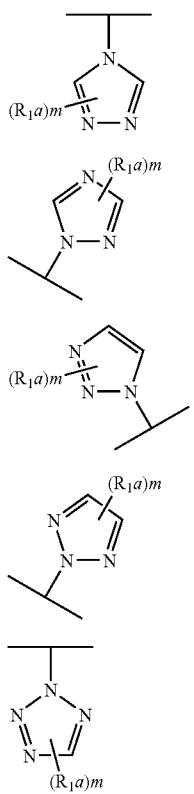

wherein in HET-3, $R_1a$ is a substituent on carbon;
$R_1a$ is independently selected from $R_1a1$ to $R_1a5$ below:

$R_1a1$: AR1, AR2, AR2a, AR2b, AR3, AR3a, AR3b, AR4, AR4a, CY1, CY2;

$R_1a2$: cyano, carboxy, (1-4C)alkoxycarbonyl, —C(=W)NRvRw [wherein W is O or S, Rv and Rw are independently H, or (1-4C)alkyl and wherein Rv and Rw taken together with the amide or thioamide nitrogen to which they are attached can form a 5-7 membered ring optionally with an additional heteroatom selected from N, O, S(O)n in place of 1 carbon atom of the so formed ring; wherein when said ring is a piperazine ring, the ring may be optionally substituted on the additional nitrogen by a group selected from (1-4C)alkyl, (3-6C)cycloalkyl, (1-4C)alkanoyl, —COO(1-4C)alkyl, —S(O)n(1-4C)alkyl (wherein n=1 or 2), —COOAR1, —CS(1-4C)alkyl) and —C(=S)O(1-4C)alkyl; wherein any (1-4C)alkyl, (1-4C)alkanoyl and (3-4C)cycloalkyl substituent may itself be substituted by cyano, hydroxy or halo, provided that, such a substituent is not on a carbon adjacent to a nitrogen atom of the piperazine ring], ethenyl, 2-(1-4C)alkylethenyl, 2-cyanoethenyl, 2-cyano-2-((1-4C)alkyl)ethenyl, 2-nitroethenyl, 2-nitro-2-((1-4C)alkyl)ethenyl, 2-((1-4C)alkylaminocarbonyl)ethenyl, 2-((1-4C)alkoxycarbonyl)ethenyl, 2-(AR1)ethenyl, 2-(AR2)ethenyl, 2-(AR2a)ethenyl;

$R_1a3$: (1-10C)alkyl

{optionally substituted by one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkylcarbonyl, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], and amino; and/or optionally substituted by one group selected from carboxy, phosphonate [phosphono, —P(O)(OH)$_2$, and mono- and di-(1-4C)alkoxy derivatives thereof], phosphinate [—P (OH)$_2$ and mono- and di-(1-4C)alkoxy derivatives thereof], cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino-, (1-4C)alkoxycarbonylamino-, N-(1-4C)alkyl-N-(1-6C)alkanoylamino-, —C(=W)NRvRw [wherein W is O or S, Rv and Rw are independently H, or (1-4C)alkyl and wherein Rv and Rw taken together with the amide or thioamide nitrogen to which they are attached can form a 5-7 membered ring optionally with an additional hetero atom selected from N, O, S(O)n in place of 1 carbon atom of the so formed ring; wherein when said ring is a piperazine ring, the ring may be optionally substituted on the additional nitrogen by a group selected from (1-4C)alkyl, (3-6C)cycloalkyl, (1-4C)alkanoyl, —COO(1-4C)alkyl, —S(O)$_n$(1-4C)alkyl (wherein n=1 or 2), —COOAR1, —CS(1-4C)alkyl and —C(=S)O(1-4C)alkyl], (=NORv) wherein Rv is as hereinbefore defined, (1-4C)alkylS(O)$_p$NH—, (1-4C)alkylS(O)$_p$-((1-4C)alkyl)N—, fluoro(1-4C)alkylS(O)$_p$NH—, fluoro(1-4C)alkylS(O)$_p$((1-4C)alkyl)N—, (1-4C)alkylS(O)$_q$—, CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups}; wherein any (1-4C)alkyl, (1-4C)alkanoyl and (3-6C)cycloalkyl present in any substituent on R$_1$a3 may itself be substituted by one or two groups independently selected from cyano, hydroxy, halo, amino, (1-4C)alkylamino and di(1-4C)alkylamino, provided that such a substituent is not on a carbon adjacent to a heteroatom atom if present;

R$_1$a4: R$_{14}$C(O)O(1-6C)alkyl- wherein R$_{14}$ is AR1, AR2, AR2a, AR2b, (1-4C)alkylamino, benzyloxy-(1-4C)alkyl or (1-10C)alkyl {optionally substituted as defined for (R$_1$a3)};

R$_1$a5: F, Cl, hydroxy, mercapto, (1-4C)alkylS(O)$_p$— (p=0, 1 or 2), —NR$_7$R$_8$ (wherein R$_7$ and R$_8$ are as hereinbefore defined) or —OR$_{10}$ (where R$_{10}$ is as hereinbefore defined); m is 0, 1 or 2;

R$_{21}$ is selected from hydrogen, methyl [optionally substituted with cyano, trifluoromethyl, —C=WNRvRw (where W, Rv and Rw are as hereinbefore defined for R$_1$a3), (1-4C)alkoxycarbonyl, (1-4C)alkoxy-(1-4C)alkoxycarbonyl, (1-4C)alkoxy-(1-4C)alkoxy-(1-4C)alkoxycarbonyl, CY1, CY2, AR1, AR2, AR2a, AR2b (not linked through nitrogen) or AR3], (2-10C)alkyl [optionally substituted other than on a carbon attached to the HET-3 ring nitrogen with one or two groups independently selected from the optional subsituents defined for R$_1$a3] and R$_{14}$C(O)O(2-6C)alkyl-, wherein R$_{14}$ is as defined hereinbefore for R$_1$a4 and wherein R$_{14}$C(O)O group is attached to a carbon other than the carbon attached to the HET-3 ring nitrogen;

R$_{22}$ is cyano, —COR$_{12}$, —COOR$_{12}$, —CONHR$_{12}$, —CON(R$_{12}$)(R$_{13}$), —SO$_2$R$_{12}$ (provided that R$_{12}$ is not hydrogen), —SO$_2$NHR$_{12}$, —SO$_2$N(R$_{12}$)(R$_{13}$) or NO$_2$, wherein R$_{12}$ and R$_{13}$ are as defined hereinbelow;

R$_{12}$ and R$_{13}$ are independently selected from hydrogen, phenyl (optionally substituted with one or more substituents selected from halogen, (1-4C)alkyl and (1-4C)alkyl substituted with one, two, three or more halogen atoms) and (1-4C)alkyl (optionally substituted with one, two, three or more halogen atoms), or for any N(R$_{12}$)(R$_{13}$) group, R$_{12}$ and R$_{13}$ may be taken together with the nitrogen to which they are attached to form a 5-7 membered ring optionally with an additional heteroatom selected from N, O, S(O)n in place of 1 carbon atom of the so formed ring; wherein the ring may be optionally substituted by one or two groups independently selected from (1-4C)alkyl (optionally substituted on a carbon not adjacent to the nitrogen by cyano, hydroxy or halo), (3-6C)cycloalkyl, (1-4C)alkanoyl, —COO(1-4C)alkyl, —S(O)$_n$(1-4C)alkyl (wherein n=1 or 2), AR1, AR2, —C=OAR1, —C=OAR2, —COOAR1, —CS(1-4C)alkyl, —C(=S)O(1-4C)alkyl, —C(=W)NRvRw [wherein W is O or S, Rv and Rw are independently H, or (1-4C)alkyl], —S(O)pAR1 and —S(O)pAR2; wherein any (1-4C)alkyl chain may be optionally substituted by (1-4C)alkyl, cyano, hydroxy or halo; p=0, 1 or 2;

AR1 is an optionally substituted phenyl or optionally substituted naphthyl;

AR2 is an optionally substituted 5- or 6-membered, fully unsaturated (i.e. with the maximum degree of unsaturation) monocyclic heteroaryl ring containing up to four heteroatoms independently selected from O, N and S (but not containing any O—O, O—S or S—S bonds), and linked via a ring carbon atom, or a ling nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e. with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e. with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring;

wherein; optional substituents on AR1, AR2, AR2a, AR2b, AR3, AR3a, AR3b, AR4, AR4a, CY1 and CY2 are (on an available carbon atom) up to three substituents independently selected from (1-4C)alkyl {optionally substituted by substituents selected independently from hydroxy, trifluoromethyl, (1-4C)alkylS(O)$_q$— (q is 0, 1 or 2), (1-4C)alkoxy, (1-4C)alkoxycarbonyl, cyano, nitro, (1-4C)alkanoylamino, —CONRvRw or —NRvRw}, trifluoromethyl, hydroxy, halo, nitro, cyano, thiol, (1-4C)alkoxy, (1-4C)alkanoyloxy, dimethylaminomethyleneaminocarbonyl, di(N-(1-4C)alkyl) aminomethylimino, carboxy, (1-4C)alkoxycarbonyl, (1-4C) alkanoyl, (1-4C)alkylSO$_2$amino, (2-4C)alkenyl {optionally substituted by carboxy or (1-4C)alkoxycarbonyl}, (2-4C) alkynyl, (1-4C)alkanoylamino, oxo (=O), thioxo (=S), (1-4C)alkanoylamino {the (1-4C)alkanoyl group being optionally substituted by hydroxy}, (1-4C)alkyl S(O)$_q$— (q is 0, 1 or 2) {the (1-4C)alkyl group being optionally substituted by one or more groups independently selected from cyano, hydroxy and (1-4C)alkoxy}, —CONRvRw or —NRvRw [wherein Rv is hydrogen or (1-4C)alkyl; Rw is hydrogen or (1-4C)alkyl];

and further optional substituents on AR1, AR2, AR2a, AR2b, AR3, AR3a, AR3b, AR4, AR4a, CY1 and CY2 (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1-4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1-4C)alkyl, (1-4C)alkoxyimino(1-4C)alkyl, halo-(1-4C)alkyl, (1-4C)alkanesulfonamido, —SO$_2$NRvRw [wherein Rv is hydrogen or (1-4C)alkyl; Rw is hydrogen or (1-4C)alkyl]; and optional substituents on AR2, AR2a, AR2b, AR3, AR3a, AR3b, AR4 and AR4a are (on an available nitrogen atom, where such substitution does not result in quaternization) (1-4C)alkyl, (1-4C)alkylcarbonyl {wherein the (1-4C)alkyl and (1-4C)alkylcarbonyl groups are optionally substituted by (preferably one) substituents independently selected from cyano, hydroxy, nitro, trifluoromethyl, (1-4C)alkyl S(O)$_q$— (q is 0, 1 or 2), (1-4C)alkoxy, (1-4C)alkoxycarbonyl, (1-4C) alkanoylamino, —CONRvRw or —NRvRw [wherein Rv is hydrogen or (1-4C)alkyl; Rw is hydrogen or (1-4C)alkyl]}, (2-4C)alkenyl, (2-4C)alkynyl, (1-4C)alkoxycarbonyl or oxo (to form an N-oxide).

In another aspect, the invention relates to compounds of formula (1) as hereinabove defined or to a pharmaceutically acceptable salt.

In another aspect, the invention relates to compounds of formula (1) as hereinabove defined or to a pro-drug thereof. Suitable examples of pro-drugs of compounds of formula (1) are in-vivo hydrolysable esters of compounds of formula (1). Therefore in another aspect, the invention relates to compounds of formula (1) as hereinabove defined or to an in-vivo hydrolysable ester thereof.

In another aspect, there is provided a compound of the formula (I) as hereinbefore defined, wherein HET3 is selected from
 a) HET3-A to HET3-E;
 b) HET3-F to HET3-Y; and
 c) HET3-Z to HET3-AE.

Where optional substituents are chosen from "0, 1, 2 or 3" groups it is to be understood that this definition includes all substituents being chosen from one of the specified groups or the substituents being chosen from two or more of the specified groups. An analogous convention applies to substituents chose from "0, 1 or 2" groups and "1 or 2" groups.

In this specification the term 'alkyl' includes straight chained and branched structures. For example, (1-4C)alkyl includes propyl and isopropyl. However, references to individual alkyl groups such as "propyl" are specific for the straight chained version only, and references to individual branched chain alkyl groups such as "isopropyl" are specific for the branched chain version only. In this specification, the terms 'alkenyl' and 'cycloalkenyl' include all positional and geometrical isomers. In this specification, the term 'aryl' is an unsubstituted carbocyclic aromatic group, in particular phenyl, 1- and 2-naphthyl.

For the avoidance of doubt, reference to a carbon atom in HET1 or HET2 being substituted by an oxo or thioxo group means replacement of a CH$_2$ by C=O or C=S respectively.

Within this specification composite terms are used to describe groups comprising more that one functionality such as (1-4C)alkoxy-(1-4C)alkoxy-(1-4C)alkyl. Such terms are to be interpreted in accordance with the meaning which is understood by a person skilled in the art for each component part For example (1-4C)alkoxy-(1-4C)alkoxy-(1-4C)alkyl includes methoxymethoxymethyl, ethoxymethoxypropyl and propxyethoxymethyl.

It will be understood that where a group is defined such that is optionally substituted by more than one substituent, then substitution is such that chemically stable compounds are formed. For example, a trifluoromethyl group may be allowed but not a trihydroxymethyl group. This convention is applied wherever optional substituents are defined.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention.

Examples of (1-4C)alkyl and (1-5C)alkyl include methyl, ethyl, propyl, isopropyl and t-butyl; examples of (1-6C)alkyl include methyl, ethyl, propyl, isopropyl, t-butyl, pentyl and hexyl; examples of (1-10C)alkyl include methyl, ethyl, propyl, isopropyl, pentyl, hexyl, heptyl, octyl and nonyl; examples of (1-4C)alkanoylamino-(1-4C)alkyl include formamidomethyl, acetamidomethyl and acetamidoethyl; examples of hydroxy(1-4C)alkyl and hydroxy(1-6C)alkyl include hydroxymethyl, 1-hydroxyethyl, 2-hydroxyethyl and 3-hydroxypropyl; examples of (1-4C)alkoxycarbonyl include methoxycarbonyl, ethoxycarbonyl and propoxycarbonyl; examples of (1-4C)alkoxy-(1-4C)alkoxycarbonyl include methoxymethoxycarbonyl, methoxyethoxycarbonyl and propoxymethoxycarbonyl; examples of (1-4C)alkoxy-(1-4C)alkoxy-(1-4C)alkoxycarbonyl include methoxymethoxymethoxycarbonyl, methoxyethoxymethoxycarbonyl and propoxyethoxymethoxycarbonyl; examples of 2-((1-4C)alkoxycarbonyl)ethenyl include 2-(methoxycarbonyl)ethenyl and 2-(ethoxycarbonyl)ethenyl; examples of 2-cyano-2-((1-4C)alkyl)ethenyl include 2-cyano-2-methylethenyl and 2-cyano-2-ethylethenyl; examples of 2-nitro-2-((1-4C)alkyl)ethenyl include 2-nitro-2-methylethenyl and 2-nitro-2-ethylethenyl; examples of 2-((1-4C)alkylaminocarbonyl)ethenyl include 2-(methylaminocarbonyl)ethenyl and 2-(ethylaminocarbonyl)ethenyl; examples of (2-4C)alkenyl include allyl and vinyl; examples of (2-4C)alkenyloxy include allyloxy and vinyloxy; examples of (2-4C)alkynyl include ethynyl and 2-propynyl; examples of (2-4C)alkynyloxy include ethynyloxy and 2-propynyloxy; examples of (1-4C)alkanoyl include formyl, acetyl and propionyl; examples of (1-4C)alkylcarbonyl include acetyl and propionyl; examples of (1-4C)alkoxy include methoxy, ethoxy and propoxy; examples of (1-6C)alkoxy and (1-10C)alkoxy include methoxy, ethoxy, propoxy and pentoxy; examples of (1C)alkylthio include methylthio and ethylthio; examples of (1-4C)alkylamino include ethylamino, ethylamino and propylamino; examples of (2-4C)alkenylamino include vinylamino and allylamino; examples of hydroxy(1-4C)alkylamino include 2-hydroxyethylamino, 2-hydroxypropylamino and 3-hydroxypropylamino; examples of di-((1-4C)alkyl)amino include dimethylamino, N-ethyl-N-methylamino, diethylamino, N-methyl-N-propylamino and dipropylamino; examples of halo groups include fluoro, chloro and bromo; examples of (1-4C)alkylsulfonyl include methylsulfonyl and ethylsulfonyl; examples of (1-4C)alkoxy-(1-4C)alkoxy and (1-6C)alkoxy-(1-6C)alkoxy include methoxymethoxy, 2-methoxyethoxy, 2-ethoxyethoxy and 3-methoxypropoxy; examples of (1-4C)alkoxy-(1-4C)alkoxy-(1-4C)alkoxy include 2-(methoxymethoxy)ethoxy, 2-(2-methoxyethoxy)ethoxy; 3-(2-methoxyethoxy)propoxy and 2-(2-ethoxyethoxy)ethoxy; examples of (1-4C)alkylS(O)$_2$amino include methylsulfonylamino and ethylsulfonylamino; examples of (1-4C)alkanoylamino and (1-6C)alkanoylamino include formamido, acetamido and propionylamino; examples of (1-4C)alkoxycarbonylamino include methoxycarbonylamino and ethoxycarbonylamino; examples of N-(1-4C)alkyl-N-(1-6C)alkanoylamino include N-methylacetamido, N-ethylacetamido and N-methylpropionamido; examples of (1-4C)alkylS(O)$_p$NH— wherein p is 1 or 2 include methylsulfinylamino, methylsulfonylamino, ethylsulfinylamino and ethylsulfonylamino; examples of (1-4C)alkylS(O)$_p$((1-4C)alkyl)N— wherein p is 1 or 2 include methylsulfinylmethylamino, methylsulfonylmethylamino, 2-(ethylsulfinyl)ethylamino and 2-(ethylsulfonyl)ethylamino; examples of fluoro(1-4C)alkylS(O)$_p$NH— wherein p is 1 or 2 include trifluoromethylsulfinylamino and trifluoromethylsulfonylamino; examples of fluoro(1-4C)alkylS(O)$_p$((1-4C)alkyl)NH— wherein p is 1 or 2 include trifluoromethylsulfinylmethylamino and trifluoromethylsulfonylmethylamino examples of (1-4C)alkoxy(hydroxy)phosphoryl include methoxy(hydroxy)phosphoryl and ethoxy(hydroxy)phosphoryl; examples of di-(1-4C)alkoxyphosphoryl include di-methoxyphosphoryl, di-ethoxyphosphoryl and ethoxy(methoxy)phosphoryl; examples of (1-4C)alkylS(O)$_q$— wherein q is 0, 1 or 2, and —S(O)$_n$(1-4C)alkyl (wherein n=1 or 2), include methylthio, ethylthio, methylsulfinyl, ethylsulfinyl, methylsulfonyl and ethylsulfonyl; examples of phenylS(O)$_q$ and naphthylS(O)$_q$— wherein q is 0, 1 or 2 are phenylthio, phenylsulfinyl, phenylsulfonyl and naphthylthio, naphthylsulfinyl and naphthylsulfonyl respectively; examples of benzyloxy-(1-4C)alkyl include benzyloxymethyl and benzyloxyethyl; examples of a (3-4C)alkylene chain are trimethylene or tetramethylene; examples of (1-6C)alkoxy-(1-6C)alkyl include methoxymethyl, ethoxymethyl and 2-methoxyethyl; examples of hydroxy-(2-6C)alkoxy include 2-hydroxyethoxy and 3-hydroxypropoxy; examples of (1-4C)alkylamino-(2-6C)alkoxy include 2-methylaminoethoxy and 2-ethylaminoethoxy; examples of di-(1-4C)alkylamino-(2-6C)alkoxy include 2-dimethylaminoethoxy and 2-diethylaminoethoxy; examples of phenyl(1-4C)alkyl include benzyl and phenethyl; examples of (1-4C)alkylcarbamoyl include methylcarbamoyl and ethylcarbamoyl; examples of di((1-4C)alkyl)carbamoyl include di(methyl)carbamoyl and di(ethyl)carbamoyl; examples of hydroxyimino(1-4C)alkyl include hydroxyiminomethyl, 2-(hydroxyimino)ethyl and 1-(hydroxyimino)ethyl; examples of (1-4C)alkoxyimino-(1-4C)alkyl include methoxyiminomethyl, ethoxyiminomethyl, 1-(methoxyimino)ethyl and 2-(methoxyimino)ethyl; examples of halo(1-4C)alkyl include, halomethyl, 1-haloethyl, 2-haloethyl, and 3-halopropyl; examples of nitro(1-4C)alkyl include nitromethyl, 1-nitroethyl, 2-nitroethyl and 3-nitropropyl; examples of amino(1-4C)alkyl include aminomethyl, 1-aminoethyl, 2-aminoethyl and 3-aminopropyl; examples of cyano(1-4C)alkyl include cyanomethyl, 1-cyanoethyl, 2-cyanoethyl and 3-cyanopropyl; examples of (1-4C)alkanesulfonamido include methanesulfonamido and ethanesulfonamido; examples of (1-4C)alkylaminosulfonyl include methylaminosulfonyl and ethylaminosulfonyl; examples of di-(1-4C)alkylaminosulfonyl include dimethylaminosulfonyl, diethylaminosulfonyl and N-methyl-N-ethylaminosulfonyl; examples of (1-4C)alkanesulfonyloxy include methylsulfonyloxy, ethylsulfonyloxy and propylsulfonyloxy; examples of (1-4C)alkanoyloxy include acetoxy and propionyloxy; examples of (1-4C)alkylaminocarbonyl include methylaminocarbonyl and ethylaminocarbonyl; examples of di((1-4C)alkyl)aminocarbonyl include dimethylaminocarbonyl and diethylaminocarbonyl; examples of (3-6C)cycloalkyl include cyclopropyl, cyclobutyl, cyclopentyl and cyclohexyl; examples of (3-6C)cycloalkenyl include cyclopropenyl, cyclobutenyl, cyclopentenyl and cyclohexenyl; examples of (4-7C)cycloalkyl include cyclobutyl, cyclopentyl and cyclohexyl; examples of di(N-(1-4C)alkyl)aminomethylimino include dimethylaminomethylimino and diethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyrid-4-yl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolan-4-yl, 1,3-dioxan-4-yl, 1,3-dioxan-5-yl and 1,4-dioxan-2-yl.

Particular values for AR3 include, for example, bicyclic benzo-fused systems containing a 5- or 6-membered heteroaryl ring containing one nitrogen atom and optionally 1-3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazine and cinnoline.

Other particular examples of AR3 include 5/5-, 5/6 and 6/6 bicyclic ring systems containing heteroatoms in both of the rings. Specific examples of such ring systems include, for example, purine and naphthyridine.

Further particular examples of AR3 include bicyclic heteroaryl ring systems with at least one bridgehead nitrogen and optionally a further 1-3 heteroatoms chosen from oxygen, sulfur and nitrogen. Specific examples of such ring systems include, for example, 3H-pyrrolo[1,2-a]pyrrole, pyrrolo[2,1-b]thiazole, 1H-imidazo[1,2-a]pyrrole, 1H-imidazo[1,2-a]imidazole, 1H,3H-pyrrolo[1,2-c]oxazole, 1H-imidazo[1,5-a]pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1,2-b]pyridazine, pyrrolo[1,2-c]pyrimidine, pyrrolo[1,2-a]pyrazine, pyrrolo[1,2-a]pyrimidine, pyrido[2,1-c]-s-triazole, s-triazolo[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazine, [3H-oxazolo[3,4-a]pyridine, [6H]-pyrrolo[2,1-c]oxazine and pyrido[2,1-c][1,4]oxazine. Other specific examples of 5/5-bicyclic ring systems are imidazooxazole or imidazothiazole, in particular imidazo[5,1-b]thiazole, imidazo[2,1-b]thiazole, imidazo[5,1-b]oxazole or imidazo[2,1-b]oxazole.

Particular examples of AR3a and AR3b include, for example, indoline, 1,3,4,6,9,9a-hexahydropyrido[2,1c][1,4]oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8,8a-hexahydrooxazolo[3,4a]pyridin-7-yl, (7aS)[3H,5H]-1,7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H]-pyrrolo[1,2-c]oxazol-6-yl, [5H-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo-[3,4-a]pyrid-7-yl, [3H]-5,8-dihydroxazolo[3,4-a]pyrid-7-yl and 5,8-dihydroimidazo-[1,5-a]pyrid-7-yl.

Particular values for AR4 include, for example, pyrrolo[a]quinoline, 2,3-pyrroloisoquinoline, pyrrolo[a]isoquinoline, 1H-pyrrolo[1,2-a]benzimidazole, 9H-imidazo[1,2-a]indole, 5H-imidazo[2,1-a]isoindole, 1H-imidazo[3,4-a]indole, imidazo[1,2-a]quinoline, imidazo[2,1-a]isoquinoline, imidazo[1,5-a]quinoline and imidazo[5,1-a]isoquinoline.

The nomenclature used is that found in, for example, "Heterocyclic Compounds (Systems with bridgehead nitrogen), W. L. Mosby (Interscience Publishers Inc., New York), 1961, Parts 1 and 2.

Where optional substituents are listed such substitution is preferably not geminal disubstitution unless stated otherwise. If not stated elsewhere, suitable optional substituents for a particular group are those as stated for similar groups herein.

Preferable optional substituents on Ar2b as 1,3-dioxolan-4-yl, 1,3-dioxan-4-yl, 1,3-dioxan-5-yl or 1,4-dioxan-2-yl are mono- or disubstitution by substituents independently selected from (1-4C)alkyl (including geminal disubstitution), (1-4C)alkoxy, (1-4C)alkylthio, acetamido, (1-4C)alkanoyl, cyano, trifluoromethyl and phenyl].

Preferable optional substituents on CY1 & CY2 are mono- or disubstitution by substituents independently selected from (1-4C)alkyl (including geminal disubstitution), hydroxy, (1-4C)alkoxy, (1-4C)alkylthio, acetamido, (1-4C)alkanoyl, cyano, and trifluoromethyl.

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the invention may be administered in the form of a pro-drug which is broken down in the human or animal body to give a compound of the invention. A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the invention or a pharmaceutically-acceptable salt thereof.

Various forms of prodrugs are known in the art, for examples see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

Suitable pro-drugs for pyridine or triazole derivatives include acyloxymethyl pyridinium or triazolium salts eg halides; for example a pro-drug such as:

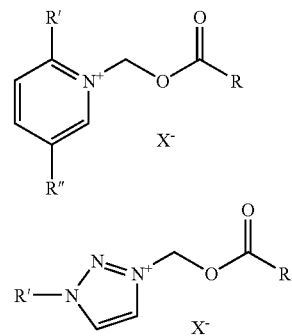

(Ref: T. Yamazaki et al. 42$^{nd}$ Iterscience Conference on Antimicrobial Agents and Chemotherapy, San Diego, 2002; Abstract F820).

Suitable pro-drugs of hydroxyl groups are acyl esters of acetal-carbonate esters of formula RCOOC(R,R')OCO—, where R is (1-4C)alkyl and R' is (1-4C)alkyl or H. Further suitable prodrugs are carbonate and carabamate esters RCOO— and RNHCOO—.

An in-vivo hydrolysable ester of a compound of the invention or a pharmaceutically-acceptable salt thereof containing a carboxy or hydroxy group is, for example, a pharmaceutically-acceptable ester which is hydrolysed in the human or animal body to produce the parent alcohol.

Suitable pharmaceutically-acceptable esters for carboxy include (1-6C)alkoxymethyl esters for example methoxymethyl, (1-6C)alkanoyloxymethyl esters for example pivaloyloxymethyl, phthalidyl esters, (3-8C)cycloalkoxycarbonyloxy(1-6C)alkyl esters for example 1-cyclohexylcarbonyloxyethyl; 1,3-dioxolan-2-onylmethyl esters for example 5-methyl-1,3-dioxolan-2-ylmethyl; and (1-6C)alkoxycarbonyloxyethyl esters for example 1-methoxycarbonyloxyethyl and may be formed at any carboxy group in the compounds of this invention.

An in-vivo hydrolysable ester of a compound of the invention or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1-10C)alkanoyl, benzoyl, phenylacetyl and substituted benzoyl and phenylacetyl, (1-10C)alkoxycarbonyl (to give alkyl carbonate esters), di-(1-4C)alkylcarbamoyl and N-(di-(1-4C)alkylaminoethyl)-N-(1-4C)alkylcarbamoyl (to give carbamates), di-(1-4C)alkylaminoacetyl, carboxy(2-5C)alkylcarbonyl and carboxyacetyl. Examples of ring substituents on phenylacetyl and benzoyl include chloromethyl or aminomethyl, (1-4C)alkylaminomethyl and di-((1-4C)alkyl)aminomethyl, and morpholino or piperazino linked from a ring nitrogen atom via a methylene lining group to the 3- or 4-position of the benzoyl ring. Other interesting in-vivo hydrolysable esters include, for example, $R^A C(O)O(1-6C)alkyl-CO$— (wherein $R^A$ is for example, optionally substituted benzyloxy-(1-4C)alkyl, or optionally substituted phenyl; suitable substituents on a phenyl group in such esters include, for example, 4-(1-4C)piperazino-(1-4C)alkyl, piperazino-(1-4C)alkyl and morpholino-(1-4C)alkyl.

Suitable in-vivo hydrolysable esters of a compound of the formula (I) are described as follows. For example, a 1,2-diol may be cyclised to form a cyclic ester of formula (PD1) or a pyrophosphate of formula (PD2), and a 1,3-diol may be cyclised to form a cyclic ester of the formula (PD3):

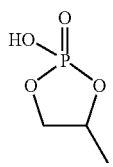
(PD1)

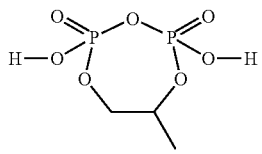
(PD2)

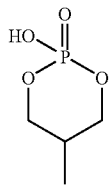
(PD3)

Esters of compounds of formula (I) wherein the HO— function/s in (PD1), (PD2) and (PD3) are protected by (1-4C) alkyl, phenyl or benzyl are useful intermediates for the preparation of such pro-drugs.

Further in-vivo hydrolysable esters include phosphoramidic esters, and also compounds of invention in which any free hydroxy group independently forms a phosphoryl (npd is 1) or phosphiryl (npd is 0) ester of the formula (PD4):

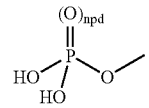
(PD4)

For the avoidance of doubt, phosphono is —P(O)(OH)$_2$; (1-4C)alkoxy(hydroxy)-phosphoryl is a mono-(1-4C)alkoxy derivative of —O—P(O)(OH)$_2$; and di-(1-4C)alkoxyphosphoryl is a di-(1-4C)alkoxy derivative of —O—P(O)(OH)$_2$.

Useful intermediates for the preparation of such esters include compounds containing a group/s of formula (PD4) in which either or both of the —OH groups in (PD1) is independently protected by (1-4C)alkyl (such compounds also being interesting compounds in their own right), phenyl or phenyl-(1-4C)alkyl (such phenyl groups being optionally substituted by 1 or 2 groups independently selected from (1-4C)alkyl, nitro, halo and (1-4C)alkoxy).

Thus, prodrugs containing groups such as (PD1), (PD2), (PD3) and (PD4) may be prepared by reaction of a compound of invention containing suitable hydroxy group/s with a suitably protected phosphorylating agent (for example, containing a chloro or dialkylamino leaving group), followed by oxidation (if necessary) and deprotection.

Other suitable prodrugs include phosphonooxymethyl ethers and their salts, for example a prodrug of R—OH such as:

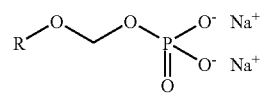

When a compound of invention contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Where pharmaceutically-acceptable salts of an in-vivo hydrolysable ester may be formed this is achieved by conventional techniques. Thus, for example, compounds containing a group of formula (PD1), (PD2), (PD3) and/or (PD4) may ionise (partially or fully) to form salts with an appropriate number of counter-ions. Thus, by way of example, if an in-vivo hydrolysable ester prodrug of a compound of invention contains two (PD4) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at the C-5 positions of the oxazolidinone ring. The pharmaceutically active diastereomer is of the formula (Ia):

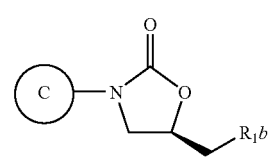
(Ia)

which is generally the (5R) configuration, depending on the nature of $R_1b$ and C.

The present invention includes pure diastereomers or mixtures of diastereomers, for example a racemic mixture. If a mixture of enantiomers is used, a larger amount (depending upon the ratio of the enantiomers) will be required to achieve the same effect as the same weight of the pharmaceutically active enantiomer.

Furthermore, some compounds of the invention may have other chiral centres, for example on substituents on group C. It is to be understood that the invention encompasses all such optical and diastereoisomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

The invention relates to all tautomeric forms of the compounds of the invention that possess antibacterial activity.

It is also to be understood that certain compounds of the invention can exist in solvated as well as unsolvated forms such as, for example, hydrated forms. It is to be understood that the invention encompasses all such solvated forms which possess antibacterial activity.

It is also to be understood that certain compounds of the invention may exhibit polymorphism, and that the invention encompasses all such forms which possess antibacterial activity.

As stated before, we have discovered a range of compounds that have good activity against a broad range of Gram-positive pathogens including organisms known to be resistant to most commonly used antibiotics, together with activity against fastidious Gram negative pathogens such as *H. influenzae, M. catarrhalis, Mycoplasma* and *Chlamydia* strains. The following compounds possess preferred pharmaceutical and/or physical and/or pharmacokinetic properties.

In one embodiment of the invention are provided compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of formula (I).

In one aspect, an in-vivo hydrolysable ester of a compound of the formula (I) is a phosphoryl ester (as defined by formula (PD4) with npd as 1).

Compounds of the formula (I), or a pharmaceutically-acceptable salt or an in-vivo hydrolysable ester thereof, wherein C is selected from group D or group E represent separate and independent aspects of the invention.

Particularly preferred compounds of the invention comprise a compound of the invention, or a pharmaceutically-acceptable salt or an in-vivo hydrolysable ester thereof, wherein the substituents $R_1a$, $R_1b$, $R_2a$, $R_2b$, $R_3a$, $R_6a$ and $R_6b$ and other substituents mentioned above have values disclosed hereinbefore, or any of the following values (which may be used where appropriate with any of the definitions and embodiments disclosed hereinbefore or hereinafter):

In one embodiment are provided compounds of the formula (I) or pharmaceutically acceptable salt or in-vivo hydrolysable ester thereof wherein group C is group D.

In another embodiment are provided compounds of the formula (I) or pharmaceutically acceptable salt or in-vivo hydrolysable ester thereof wherein group C is group E.

In one aspect $R_2a$ and $R_6a$ are hydrogen.

In one aspect one $R_2b$ and $R_6b$ is fluoro and the other is hydrogen. In another aspect both one $R_2b$ and $R_6b$ are fluoro. In a further aspect $R_2b$ is fluoro and $R_6b$ is selected from Cl, $CF_3$, Me, Et, OMe and SMe.

In one aspect one of $R_2b$ and $R_6b$ is chloro and other hydrogen.

In another aspect one of $R_2b$ and $R_6b$ is $CF_3$ and the other hydrogen.

In another aspect one of $R_2b$ and $R_6b$ is Me and the other hydrogen.

In another aspect one of $R_2b$ and $R_6b$ is Et and the other hydrogen.

In another aspect one of $R_2b$ and $R_6b$ is OMe and the other hydrogen.

In another aspect one of $R_2b$ and $R_6b$ is SMe and the other hydrogen.

In one aspect $R_3a$ is selected from H, (1-4C)alkyl, cyano, Br, F, Cl, OH, (1-4C)alkoxy, —S(1-4C)alkyl, amino, nitro and —CHO. In a further aspect $R_3a$ is selected from H, Cl, Br, F, Me, Et, OMe and SMe.

In one embodiment $R_1b$ is HET1 wherein HET1 is selected from the structures (Za) to (Zf) below:

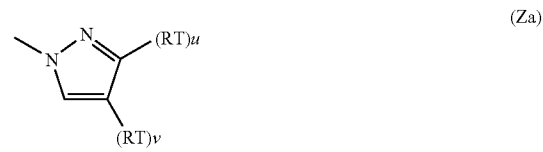
(Za)

(Zb)

(Zc)

(Zd)

(Ze)

(Zf)

wherein u and v are independently 0 or 1 and RT is as defined in any of the embodiments or aspects defined hereinbefore or hereinafter.

In one embodiment $R_1b$ is HET1 wherein HET1 is selected from 1,2,3-triazole (especially 1,2,3-triazol-1-yl (Zd)), 1,2,4-triazole (especially 1,2,4-triazol-1-yl (Zc)) and tetrazole (preferably tetrazol-2-yl (Zf)) and wherein u and v are independently 0 or 1 and RT is as defined in any of the embodiments or aspects defined hereinbefore or hereinafter.

In another embodiment $R_1b$ is HET1 wherein HET1 is selected from 1,2,3-triazol-1-yl (Zd) and tetrazol-2-yl (Zf) and wherein u and v are independently 0 or 1 and RT is as defined in any of the embodiments or aspects defined hereinbefore or hereinafter.

In another embodiment $R_1b$ is HET1 wherein HET1 is 1,2,3-triazol-1-yl (Zd) and wherein u and v are independently 0 or 1 and RT is as defined in any of the embodiments or aspects defined hereinbefore or hereinafter.

In one embodiment $R_1b$ is HET2 wherein HET2 is a dihydro version of pyrimidine, pyridazine, pyrazine, 1,2,3-triazine, 1,2,4-triazine, 1,3,5-triazine and pyridine and wherein RT is as defined in any of the embodiments or aspects defined hereinbefore or hereinafter.

In another embodiment $R_1b$ is HET1 wherein HET2 is selected from pyrimidone, pyridazinone, pyrazinone, 1,2,3-triazinone, 1,2,4-triazinone, 1,3,5-triazinone and pyridone and wherein RT is as defined in any of the embodiments or aspects defined hereinbefore or hereinafter.

In another embodiment $R_1b$ is HET2 wherein HET2 is selected from thiopyrimidone, thiopyridazinone, thiopyrazinone, thio-1,2,3-triazinone, thio-1,2,4-triazinone, thio-1,3,5-triazinone and thiopyridone and wherein RT is as defined in any of the embodiments or aspects defined hereinbefore or hereinafter.

In one aspect RT is preferably selected from a substituent from the groups RTa1 to RTb2, wherein:

(RTa1) hydrogen, halogen, (1-4C)alkoxy, (2-4C)alkenyloxy, (2-4C)alkenyl, (2-4C)alkynyl, (3-6C)cycloalkyl, (3-6C)cycloalkenyl, (1-4C)alkylthio, amino, azido, cyano and nitro;

(RTa2) (1-4C)alkylamino, di-(1-4C)alkylamino and (2-4C)alkenylamino;

(RTb1) a (1-4C)alkyl group which is optionally substituted by one substituent selected from hydroxy, (1-4C)alkoxy, (1-4C)alkylthio, cyano and azido;

(RTb2) a (1-4C)alkyl group which is optionally substituted by one substituent selected from (2-4C)alkenyloxy, (3-6C)cycloalkyl and (3-6C)cycloalkenyl;

and wherein at each occurrence of an RT substituent containing an alkyl, alkenyl, alkynyl, cycloalkyl or cycloalkenyl moiety in (RTa1) or (RTa2), or (RTb1) or (RTb2) each such moiety is optionally substituted on an available carbon atom with one, two, three or more substituents independently selected from F, Cl, Br, OH and CN.

In another aspect RT is preferably selected from a substituent from the groups RTa1 and RTb1, wherein:

(RTa1) hydrogen, halogen, (1-4C)alkoxy, (2-4C)alkenyloxy, (2-4C)alkenyl, (2-4C)alkynyl, (3-6C)cycloalkyl, (3-6C)cycloalkenyl, (1-4C)alkylthio, amino, azido, cyano, and nitro;

(RTb1) a (1-4C)alkyl group which is optionally substituted by one substituent selected from hydroxy, (1-4C)alkoxy, (1-4C)alkylthio, cyano and azido;

and wherein at each occurrence of an RT substituent containing an alkyl, alkenyl, alkynyl, cycloalkyl or cycloalkenyl moiety in (RTa1) or (RTb1) each such moiety is optionally substituted on an available carbon atom with one, two, three or more substituents independently selected from F, Cl, Br, and CN.

In a further aspect RT is most preferably
(a) hydrogen; or
(b) halogen, in particular fluorine, chlorine, or bromine; or
(c) cyano; or
(d) (1-4C)alkyl, in particular methyl; or
(e) monosubstituted (1-4C)alkyl, in particular fluoromethyl, choromethyl, bromomethyl, cyanomethyl, azidomethyl, hydroxymethyl; or
(f) disubstituted (1-4C)alkyl, for example difluoromethyl, or
(g) trisubstituted (1-4C)alkyl, for example trifluoromethyl.

In one aspect $R_4$ is selected from $R_4a$. In another aspect $R_4$ is selected from $R_4b$.

In one aspect $R_4a$ is selected from (1-4C)alkyl, (3-6C)cycloalkyl, AR1, AR2, (1-4C)alkanoyl, —CS(1-4C)alkyl, —C(=W)NRvRw [wherein W is O or S, Rv and Rw are independently H, or (1-4C)alkyl], —COO(1-4C)alkyl, —C=OAR1, —C=OAR2, —COOAR1, —S(O)$_n$(1-4C)alkyl (wherein n=1 or 2), —S(O)pAR1, —S(O)pAR2 and —C(=S)O(1-4C)alkyl; wherein any (1-4C)alkyl chain may be optionally substituted by (1-4C)alkyl, cyano, hydroxy or halo; p=0,1 or 2).

In a further aspect $R_4a$ is selected from azido, —$NR_7R_8$, —$OR_{10}$(1-4C)alkoxy, —$(CH_2)_m$—$R_9$ and —$(C=O)_1$—$R_6$.

In one aspect HET-3 is selected from HET3-A, HET3-B, HET3-C, HET3-D and HET3-E.

In another aspect HET-3 is selected from HET3-F, HET3-G, HET3-H and HET3-I.

In another aspect HET-3 is selected from HET3-J, HET3-K, HET3-L, HET3-M, HET3-N, HET3-O, HET3-P, HET3-Q, HET3-R and HET3-S.

In a further aspect HET-3 is selected from HET3-J, HET3-L, HET3-M, HET3-N, HET3-P, HET3-Q, HET3-R and HET3-S.

In a further aspect HET-3 is selected from HET3-L and HET3-M.

In a further aspect HET-3 is selected from HET3-P and HET3-Q In a farther aspect HET-3 is selected from HET3-T, HET3-U, HET3-V, HET3-W, HET3-X and HET3-Y.

In a further aspect HET-3 is selected HET3-T, HET3-V, HET3-Y and HET-3-W.

In a further aspect HET-3 is selected HET3-V, and HET3-Y.

In a further aspect HET-3 is selected from HET3-Z, HET3-AA, HET3-AB, HET3-AC, HET3-AD, HET3-AE, HET3-AF, HET3-AG and HET3-AH.

When m=1, in one aspect $R_1a$ is selected from $R_1a1$; in another aspect $R_1a$ is selected from $R_1a2$; in a further aspect $R_1a$ is selected from $R_1a3$, in a further aspect $R_1a$ is selected from $R_1a4$ and in a further aspect $R_1a$ is selected from $R_1a5$.

When m=2, in one aspect both groups $R_1a$ are independently selected from the same group $R_1a1$ to $R_1a5$. In a further aspect when m=2, each $R_1a$ is independently selected from different groups $R_1a1$ to $R_1a5$.

Conveniently m is 1 or 2. In one aspect, preferably m is 1. In another aspect, preferably m is 2.

Particular values for $R_1a$ when selected from $R_1a1$ are AR1 and AR2, more particularly AR2.

Particular values for $R_1a$ when selected from $R_1a2$ are cyano and —C(=W)NRvRw [wherein W is O or S, Rv and Rw are independently H, or (1-4C)alkyl and wherein Rv and Rw taken together with the amide or thioamide nitrogen to which they are attached can form a 5-7 membered ring optionally with an additional heteroatom selected from N, O, S(O)$_n$ in place of 1 carbon atom of the so formed ring; wherein when said ring is a piperazine ring, the ring may be optionally substituted on the additional nitrogen by a group selected from (1-4C)alkyl (optionally substituted on a carbon not adjacent to the nitrogen), (3-6C)cycloalkyl, (1-4C)alkanoyl, —COO(1-4C)alkyl, —S(O)$_n$(1-4C)alkyl (wherein n=1 or 2), —COOAR1, —CS(1-4C)alkyl and —C(=S)O(1-4C)alkyl; wherein any (1-4C)alkyl, (1-4C)alkanoyl and (3-6C)cycloalkyl is optionally substituted by cyano, hydroxy or halo].

More particular values for $R_1a$ when selected from $R_1a2$ are cyano, formyl, —COO(1-4C)alkyl, —C(═O)NH$_2$, —C(═O)piperazine and —C(═O)morpholine.

Particular values for $R_1a$ when selected from $R_1a3$ are (1-10C)alkyl {optionally substituted by one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkylcarbonyl, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], and amino; and/or optionally substituted by one group selected from carboxy, cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino-, (1-4C)alkoxycarbonylamino-, N-(1-4C)alkyl-N-(1-6C)alkanoylamino-, —C(═W)NRvRw [wherein W is O, Rv and Rw are independently H, or (1-4C)alkyl and wherein Rv and Rw taken together with the amide nitrogen to which they are attached can form a morpholine, pyrrolidine, piperidine or piperazine ring; wherein when said ring is a piperazine ring, the ring may be optionally substituted on the additional nitrogen by a group selected from (1-4C)alkyl and (1-4C)alkanoyl], (1-4C)alkylS(O)$_q$—, (q is 0, 1 or 2), AR2, AR2-O—, AR2-NH—, and also AR2a, AR2b versions of AR2 containing groups}; wherein any (1-4C)alkyl and (1-4C)acyl present in any substituent on $R_1a3$ may itself be substituted by one or two groups independently selected from cyano, hydroxy, halo, amino, (1-4C)alkylamino and di(1-4C)alkylamino, provided that such a substituent is not on a carbon adjacent to a heteroatom atom if present;

More particular values for $R_1a$ when selected from $R_1a3$ are (1-10C)alkyl {optionally substituted by one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], carboxy, amino, (1-4C)alkylamino, di(1-4C)alkylamino, (1-4C)alkylS(O)q (preferably where q=2), AR2 and AR2b. More particular values for $R_1a$ when selected from $R_1a3$ are (1-6C)alkyl substituted as hereinbefore described. Even more particular values for $R_1a$ when selected from $R_1a3$ are (1-4C)alkyl substituted as hereinbefore described.

Particular values for substituents on a (1-10C)alkyl, (1-6C)alkyl or (1-4C)alkyl group comprising $R_1a3$ are hydroxy, (1-10C)alkoxy, (1-4C)alkoxy-(1-4C)alkoxy, (1-4C)alkoxy-(1-4C)alkoxy-(1-4C)alkoxy, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof] and carboxy. Preferably $R_1a3$ is a (1-4C)alkyl group substituted with 1 or 2 hydroxy groups.

Particular values for $R_1a$ when selected from $R_1a4$ are $R_{14}C(O)O(1-6C)$alkyl- wherein $R_{14}$ is selected from AR1, AR2, AR2a, AR2b and (1-10C)alkyl (optionally substituted by one or more substituents independently selected from OH and di (1-4C)alkylamino. More particular vales for $R_{14}$ are AR2a, AR2b and (1-6C)alkyl substituted with hydroxy. More particular values for $R_{14}$ are AR2a, AR2b and (1-4C)alkyl substituted with hydroxy.

Particular values for $R_1a$ when selected from $R_1a5$ are fluoro, chloro and hydroxy.

Particular values for other substituents (which may be used where appropriate with any of the definitions and embodiments disclosed hereinbefore or hereinafter) are:— a) in one aspect $R_7$ and $R_8$ are independently H or (1-4C)alkyl b) in a further aspect $R_7$ and $R_8$ taken together with the nitrogen to which they are attached form a 5-7 membered ring, optionally substituted as defined hereinbefore or hereinafter c) preferably $R_7$ and $R_8$ taken together with the nitrogen to which they are attached form a pyrrolidinyl, piperidinyl, piperazinyl or morpholinyl ring d) preferable optional subsituents on $R_7$ and $R_8$ as a pyrrolidinyl, piperidinyl, piperazinyl or morpholinyl ring are (1-4C)alkyl and (1-4C)alkanoyl, wherein the (1-4C)alkyl or (1-4C)alkanoyl group itself may be optionally substituted with one or two substituents selected from hydroxy, amino, (1-4C)alkylamino and di(1-4C)alkylamino e) In one aspect $R_9$ is selected from $R_9a$, preferably selected from AR2, AR2a and AR2b f) In another aspect $R_9$ is selected from $R_9b$, preferably selected from —C(═W)NRvRw, wherein W is O, Rv and Rw are independently H, or (1-4C)alkyl and wherein Rv and Rw taken together with the amide nitrogen to which they are attached can form a morpholine, pyrrolidine, piperidine or piperazine ring; wherein when said ring is a piperazine ring, the ring may be optionally substituted on the additional nitrogen by a group selected from (1-4C)alkyl and (1-4C)alkanoyl, and wherein any (1-4C)alkyl and (1-4C)alkanoyl may itself be substituted by one or two groups independently selected from cyano, hydroxy, halo, amino, (1-4C)alkylamino and di(1-4C)alkylamino, provided that such a substituent is not on a carbon adjacent to a heteroatom atom if present g) In a further aspect $R_9$ is selected from $R_9c$, wherein $R_9c$ is (1-6C)alkyl {optionally substituted by one, two or three groups (including germinal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkylcarbonyl, phosphoryl [—O—P(O)(OH)$_2$, and mono- and di-(1-4C)alkoxy derivatives thereof, phosphiryl [—O—P(OH)$_2$ and mono- and di-(1-4C)alkoxy derivatives thereof], and amino; and/or optionally substituted by one group selected from carboxy, cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino-, (1-4C)alkoxycarbonylamino-, N-(1-4C)alkyl-N-(1-6C)alkanoylamino-, —C(═W)NRvRw [wherein W is O, Rv and Rw are independently H, or (1-4C)alkyl and wherein Rv and Rw taken together with the amide nitrogen to which they are attached can form a morpholine, pyrrolidine, piperidine or piperazine ring; wherein when said ring is a piperazine ring, the ling may be optionally substituted on the additional nitrogen by a group selected from (1-4C)alkyl and (1-4C)alkanoyl], (1-4C)alkylS(O)$_q$— (q is 0, 1 or 2), AR2, AR2-O—, AR2-NH—, and also AR2a, AR2b versions of AR2 containing groups}; wherein any (1-4C)alkyl and (1-4C)alkanoyl present in any substituent on $R_9c$ may itself be substituted by one or two groups independently selected from cyano, hydroxy, halo, amino, (1-4C)alkylamino and di(1-4C)alkylamino, provided that such a substituent is not on a carbon adjacent to a heteroatom atom if present.

h) In a further aspect $R_9$ is selected from $R_9c$, wherein $R_9c$ is (1-6C)alkyl {optionally substituted by one, two or three groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)

alkoxy, phosphoryl [—O—P(O)(OH)$_2$, and mono- and di-(1-4C)alkoxy derivatives thereof), phosphiryl [—O—P(OH)$_z$ and mono- and di-(1-4C)alkoxy derivatives thereof], carboxy, amino, (1-4C)alkylamino, di(1-4C)alkylamino, (1-4C)alkylS(O)q (preferably where q=2), AR2 and AR2b. A more particular value for R$_9$c is (1-4C)alkyl, optionally substituted as hereinbefore described.

i) In a further aspect R$_9$ is selected from R$_9$d wherein R$_9$d is R$_{14}$C(O)O(1-6C)alkyl- and R$_{14}$ is selected from AR1, AR2, AR2a, AR2b and (1-10C)alkyl (optionally substituted by one or two substituents independently selected from OH and di (1-4C)alkylamino). Particular vales for R$_{14}$ are AR2a, AR2b and (1-6C)alkyl substituted with hydroxy. More particular values for R$_{14}$ are AR2a, AR2b and (1-4C)alkyl substituted with hydroxy.

j) Particular values for R$_{21}$ are R$_{14}$C(O)O(2-6C)alkyl-, wherein R$_{14}$ is preferably selected from AR1, AR2, AR2a, AR2b and (1-10C)alkyl (optionally substituted by one or two substituents independently selected from OH and di (1-4C)alkylamino.

k) Further particular values for R$_{21}$ are (2-10C)alkyl, optionally substituted other than on a carbon attached to the HET-3 ring nitrogen with one or two groups independently selected from the optional substituents defined hereinbefore or hereinafter for R$_1$a3; further particular values for R$_{21}$ are optionally substituted (2-6C)alkyl, more particularly optionally substituted (2-4C)alkyl.

l) Particular substituents for a (2-6C)alkyl or (2-4C)alkyl group comprising R$_{21}$ are 1 or 2 substituents independently selected from hydroxy, (1-10C)alkoxy, (1-4C)alkoxy-(1-4C)alkoxy, (1-4C)alkoxy-(1-4C)alkoxy-(1-4C)alkoxy, phosphoryl [—O—P(O)(OH)$_2$, and mono- and di-(1-4C) alkoxy derivatives thereof], phosphiryl [—O—P(OH)$_2$ and mono- and di-(1-4C)alkoxy derivatives thereof], carboxy, amino, (1-4C)alkylamino, di(1-4C)alkylamino, (1-4C) alkylS(O)q (preferably where q=2), AR2 and AR2b m) Further particular values for substituents on a (2-6C)alkyl or (2-4C)alkyl group comprising R$_{21}$ are 1 or 2 substituents independently selected from hydroxy, (1-10C)alkoxy, (1-4C)alkoxy-(1-4C)alkoxy, (1-4C)alkoxy-(1-4C)alkoxy-(1-4C)alkoxy, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof] and carboxy. Preferably substituents on a (2-6C)alkyl or (2-4C)alkyl group comprising R$_{21}$ are 1 or 2 hydroxy groups.

n) Preferably R$_{22}$ is cyano.

o) Particularly preferred values for AR2, AR2a and AR2b groups are those containing a basic nitrogen, for example pyridine, pyrrolidine, piperazine and piperidine, optionally substituted as hereinbefore defined.

In one embodiment is provided a compound of the formula (Ia) or a pharmaceutically-acceptable salt or an in-vivo hydrolysable ester thereof,

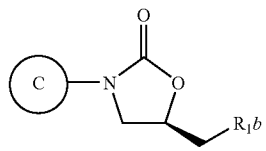

(Ia)

wherein group C is group D; R$_2$a and R$_6$a are both hydrogen; R$_2$b and R$_6$b are independently hydrogen or fluorine; and R$_4$ is selected from HET-3.

In another embodiment is provided a compound of the formula (Ia) or a pharmaceutically-acceptable salt or an in-vivo hydrolysable ester thereof, wherein group C is group D; R$_2$a and R$_6$a are both hydrogen; R$_2$b and R$_6$b are independently hydrogen or fluorine; and R$_4$ is selected from HET3-T, HET3-U, HET3-V, HET3-W, HET3-X and HET3-Y.

In another embodiment is provided a compound of the formula (Ia) or a pharmaceutically-acceptable salt or an in-vivo hydrolysable ester thereof, wherein group C is group D; R$_2$a and R$_6$a are both hydrogen; R$_2$b and R$_6$b are independently hydrogen or fluorine; and R$_4$ is selected from HET3-Z, HET3-AA, HET3-AB, HET3-AC, HET3-AD, HET3-AE, HET3-AF, HET3-AG and HET3-AH.

In another embodiment is provided a compound of the formula (Ia) or a pharmaceutically-acceptable salt or an in-vivo hydrolysable ester thereof, wherein group C is group D; R$_2$a and R$_6$a are both hydrogen; R$_2$b and R$_6$b are independently hydrogen or fluorine; R$_4$ is selected from HET3-Z, HET3-AA, HET3-AB, HET3-AC, HET3-AD, HET3-AE, HET3-AF, HET3-AG and HET3-AH; m=1 and R$_1$a is selected from R$_1$a3.

In another embodiment is provided a compound of the formula (Ia) or a pharmaceutically-acceptable salt or an in-vivo hydrolysable ester thereof, wherein group C is group E; R$_2$a and R$_6$a are both hydrogen; R$_2$b and R$_6$b are independently hydrogen or fluorine; and R$_4$ is selected from HET3-T, HET3-U, HET3-V, HET3-W, HET3-X and HET3-Y.

In another embodiment is provided a compound of the formula (Ia) or a pharmaceutically-acceptable salt or an in-vivo hydrolysable ester thereof, wherein group C is group E; R$_2$a and R$_6$a are both hydrogen; R$_2$b and R$_6$b are independently hydrogen or fluorine; and R$_4$ is selected from HET3-Z, HET3-AA, HET3-AB, HET3-AC, HET3-AD, HET3-AE, HET3-AF, HET3-AG and HET3-AH.

In another embodiment is provided a compound of the formula (Ia) or a pharmaceutically-acceptable salt or an in-vivo hydrolysable ester thereof, wherein group C is group E; R$_2$a and R$_6$a are both hydrogen; R$_2$b and R$_6$b are independently hydrogen or fluorine; R$_4$ is selected from HET3-Z, HET3-AA, HET3-AB, HET3-AC, HET3-AD, HET3-AE, HET3-AP, HET3-AG and HET3-AH; m=1 and R$_1$a is is selected from R$_1$a3.

In another embodiment is provided a compound of the formula (Ia) or a pharmaceutically-acceptable salt or an in-vivo hydrolysable ester thereof, wherein group C is group D; R$_2$a and R$_6$a are both hydrogen; R$_2$b and R$_6$b are independently hydrogen or fluorine; R$_4$ is selected from HET3-T, HET3-U, HET3-V, HET3-W, HET3-X and HET3-Y, R1b is selected from Zd and Zf, u and v are independently 0 or 1 and RT is selected from hydrogen, halogen, cyano, methyl, fluoromethyl, choromethyl, bromomethyl, cyanomethyl, azidomethyl, hydroxymethyl, difluoromethyl, and trifluoromethyl.

In another embodiment is provided a compound of the formula (Ia) or a pharmaceutically-acceptable salt or an in-vivo hydrolysable ester thereof, wherein group C is group D; R$_2$a and R$_6$a are both hydrogen; R$_2$b and R$_6$b are independently hydrogen or fluorine; and R$_4$ is selected HET3-Z, HET3-AA, HET3-AB, HET3-AC, HET3-AD, HET3-AE, HET3-AF, HET3-AG and HET3-AH, R$_1$b is selected from Zd and Zf, u and v are independently 0 or 1 and RT is selected from hydrogen, halogen, cyano, methyl, fluoromethyl, choromethyl, bromomethyl, cyanomethyl, azidomethyl, hydroxymethyl, difluoromethyl, and trifluoromethyl.

In another embodiment is provided a compound of the formula (Ia) or a pharmaceutically-acceptable salt or an in-vivo hydrolysable ester thereof, wherein group C is group D;

$R_2a$ and $R_6a$ are both hydrogen; $R_2b$ and $R_6b$ are independently hydrogen or fluorine; $R_4$ is selected from HET3-Z, HET3-AA, HET3-AB, HET3-AC, HET3-AD, HET3-AE, HET3-AF, HET3-AG and HET3-AH; m=1, $R_1a$ is selected from $R_1a3$, $R_1b$ is selected from Zd and Zf, u and v are independently 0 or 1 and RT is selected from hydrogen, halogen, cyano, methyl, fluoromethyl, choromethyl, bromomethyl, cyanomethyl, azidomethyl, hydroxymethyl, difluoromethyl, and trifluoromethyl In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; and $R_4$ is selected from HET3-T, HET3-U, HET3-V, HET3-W, HET3-X and HET3-Y, $R_1b$ is selected from Zd and Zf, u and v are independently 0 or 1 and RT is selected from hydrogen, halogen, cyano, methyl, fluoromethyl, choromethyl, bromomethyl, cyanomethyl, azidomethyl, hydroxymethyl, difluoromethyl, and trifluoromethyl In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; and $R_4$ is selected from HET3-Z, HET3-AA, HET3-AB, HET3-AC, HET3-AD, HET3-AB, HET3-AF, HET3-AG and HET3-AH, $R_1b$ is selected from Zd and Zf, u and v are independently 0 or 1 and RT is selected from hydrogen, halogen, cyano, methyl, fluoromethyl, choromethyl, bromomethyl, cyanomethyl, azidomethyl, hydroxymethyl, difluoromethyl, and trifluoromethyl In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; $R_4$ is selected from HET3-Z, HET3-AA, HET3-AB, HET3-AC, HET3-AD, HET3-AE, HET3-AF, HET3-AG and HET3-AH; m=1, $R_1a$ is selected from $R_1a3$, $R_1b$ is selected from Zd and Zf, u and v are independently 0 or 1 and RT is selected from hydrogen, halogen, cyano, methyl, fluoromethyl, choromethyl, bromomethyl, cyanomethyl, azidomethyl, hydroxymethyl, difluoromethyl, and trifluoromethyl.

In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; and $R_4$ is HET3-V, $R_1b$ is selected from Zd and Zf, u and v are independently 0 or 1 and RT is selected from hydrogen, halogen, cyano, methyl, fluoromethyl, choromethyl, bromomethyl, cyanomethyl, azidomethyl, hydroxymethyl, difluoromethyl, and trifluoromethyl In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; $R_4$ is HET3-V, $R_1b$ is Zd or Zf, u and v are independently 0 or 1, $R_{21}$ is methyl or (2-4C)alkyl (optionally substituted with 1 or 2 substituents independently selected from hydroxy, (1-10C)alkoxy, (1-4C)alkoxy-(1-4C)alkoxy, (1-4C)alkoxy-(1-4C)alkoxy-(1-4C)alkoxy, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof] and carboxy), and RT is selected from hydrogen, halogen, cyano, methyl, fluoromethyl, choromethyl, bromomethyl, cyanomethyl, azidomethyl, hydroxymethyl, difluoromethyl, and trifluoromethyl.

In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; $R_4$ is HET3-V, $R_1b$ is Zd, u and v are independently 0 or 1, $R_{21}$ is methyl or (2-4C)alkyl (optionally substituted with 1 or 2 hydroxy), and RT is selected from hydrogen, halogen, cyano, methyl, fluoromethyl, choromethyl, bromomethyl, cyanomethyl, azidomethyl, hydroxymethyl, difluoromethyl, and trifluoromethyl.

In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; $R_4$ is HET3-V, $R_1b$ is Zd, u and v are independently 0 or 1, $R_{21}$ is methyl or (2-4C)alkyl (optionally substituted with 1 or 2 hydroxy), and RT is selected from hydrogen, halogen, methyl, fluoromethyl, choromethyl, bromomethyl, difluoromethyl, and trifluoromethyl.

In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; $R_4$ is HET3-V, $R_1b$ is Zd, u and v are independently 0 or 1, $R_{21}$ is methyl or (2-4C)alkyl (optionally substituted with 1 or 2 hydroxy), and RT is selected from hydrogen, fluoro, chloro, methyl, fluoromethyl, choromethyl, difluoromethyl, and trifluoromethyl.

In another embodiment is provided a compound of the formula (Ia) or a pharmaceutically-acceptable salt or an in-vivo hydrolysable ester thereof, wherein group C is group E; $R_2a$ and $R_6a$ are both hydrogen; $R_2b$ and $R_6b$ are independently hydrogen or fluorine; $R_4$ is HET3-V, $R_1b$ is Zd, u and v are independently 0 or 1, $R_{21}$ is methyl or (2-4C)alkyl (optionally substituted with 1 or 2 hydroxy), and RT is selected from hydrogen, chloro, fluoromethyl and difluoromethyl.

In all of the above definitions the preferred compounds are as shown in formula (Ia).

Particular compounds of the present invention include each individual compound described in the Examples, each of which provides an independent aspect of the invention. A more particular compound is Example 1.

Process Section:

In a further aspect the present invention provides a process for preparing a compound of invention or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon. Resins may also be used as a protecting group.

The protecting groups may be removed at any convenient stage in the synthesis using conventional techniques well known in the chemical art.

A compound of the invention, or a pharmaceutically-acceptable salt or an in vivo hydrolysable ester thereof, may be prepared by any process known to be applicable to the preparation of chemically-related compounds. Such processes, when used to prepare a compound of the invention, or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March or Houben-Weyl, Methoden der Organischen Chemie). The preparation of such starting materials is described within the accompanying non-limiting Examples. Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the certain Patent Application Publications, the contents of the relevant process sections of which are hereby incorporated herein by reference; for example WO 94/13649; WO 98/54161; WO 99/64416; WO 99/64417; WO 00/21960; WO 01/40222.

In particular we refer to our PCT patent applications WO 99/64417 and WO 00/21960 wherein detailed guidance is given on convenient methods for preparing oxazolidinone compounds.

The skilled organic chemist will be able to use and adapt the information contained and referenced within the above references, and accompanying Examples therein and also the Examples herein, to obtain necessary starting materials, and products. For example, the skilled chemist will be able to apply the teaching herein for compounds of formula (I) in which a pyrimidyl-phenyl group is present (that is when group C is group D) to prepare compounds in which a pyridyl-phenyl group is present (that is when group C is group E) as hereinbefore defined and vice versa.

Thus, the present invention also provides that the compounds of the invention and pharmaceutically-acceptable salts and in vivo hydrolysable esters thereof, can be prepared by a process (a) to (j); and thereafter if necessary:

i) removing any protecting groups;
ii) forming a pro-drug (for example an in-vivo hydrolysable ester); and/or
iii) forming a pharmaceutically-acceptable salt;

wherein said processes (a) to (j) are as follows (wherein the variables are as defined above unless otherwise stated):

a) by modifying a substituent in, or introducing a substituent into another compound of the invention by using standard chemistry; (see for example, Comprehensive Organic Functional Group Transformations (Pergamon), Katritzky, Meth-Cohn & Rees or Advanced Organic Chemistry (Wiley-Interscience), Jerry March or Houben-Weyl, Methoden der Organischen Chemie); for example:

an acylamino group may be converted into a thioacylamino group;

an acylamino group or thioacylamino group may be converted into another acylamino or thioacylamino; heterocyclyl for instance tetrazolyl or thiazolyl, or heterocyclylamino group (optionally substituted or protected on the amino-nitrogen atom);

an acyloxy group may be converted into a hydroxy group or into the groups that may be obtained from a hydroxy group (either directly or through the intermediacy of a hydroxy group);

an alkyl halide such as alkylbromide or alkyliodide may be converted into an alkyl fluoride or nitrile;

an alkyl sulfonate such as alkyl methanesulfonate may be converted into an alkyl fluoride or nitrile;

an alkylthio group such as methylthio may be converted into a methanesulfinyl or methanesulfonyl group;

an arylthio group such as phentlthio may be converted into a benzenesulfinyl or benzenesulfonyl group;

an amidino or guanidino group may be converted into a range of 2-substituted 1,3-diazoles and 1,3-diazines;

an amino group may be converted for instance into acylamino or thioacylamino for instance an acetamide (optionally substituted), alkyl- or dialkyl-amino and thence into a further range of N-alkyl-amine derivatives, sulfonylamino, sulfinylamino, amidino, guanidino, arylamino, heteroarylamino, N-linked heterocyclic for instance an optionally 4-substituted 1,2,3-triazol-1-yl group;

an aryl- or heteroary-halide group such as an aryl- or heteroaryl chloride or bromide or iodide may be converted by transition metal mediated coupling, especially Pd(0) mediated coupling into a range of aryl-, heteroaryl, alkenyl, alkynyl, acyl, alkylthio, or alkyl- or dialkyl-amino substituted aryl or heteroaryl groups;

an aryl- or heteroary-sulfonate group such as an aryl- or hetero-aryl trifluoromethanesulfonate may be converted by transition metal mediated coupling, especially Pd(0) mediated coupling into a range of aryl-, heteroaryl, alkenyl, alkynyl, acyl, alkylthio, or alkyl- or dialkyl-amino substituted aryl or heteroaryl groups;

an aryl- or heteroary-halide group such as an aryl- or heteroaryl chloride or bromide or iodide may be converted by transition metal mediated coupling, especially Pd(0) mediated coupling into a range of trialkyltin, dialkylboronate, trialkoxysilyl, substituted aryl or heteroaryl groups useful as intermediates for the synthesis of compounds of the invention; an azido group may be converted for instance into a 1,2,3-triazolyl or amine and thence by methods that are well known in the art into any of the range common amine derivatives, such as acylamino for instance acetamido group;

a carboxylic acid group may be converted into trifloromethyl, hydroxymethyl, alkoxycarbonyl, aminocarbonyl optionally substituted on nitrogen, formyl, or acyl groups; a cyano group may be converted into a tetrazole, or an imidate, an amidine, an amidrazone, an N-hydroxyamidrazone, an amide, a thioamide, an ester, or an acid and thence by methods that are well known in the art into any of the range of heterocycles derived from such nitrile derivatives;

a hydroxy group may be converted for instance into an alkoxy, cyano, azido, alkylthio, keto and oximino, fluoro, bromo, chloro, iodo, alkyl- or aryl-sulfonyloxy for instance trifluoromethanesulfonate, methanesulfonate, or tosylsulfonate, silyloxy; acylamino or thioacylamino, for instance an acetamide (optionally substituted or protected on the amido-nitrogen atom); acyloxy, for instance an acetoxy; phosphono-oxy, heterocyclylamino (optionally substituted or protected on the amino-nitrogen atom), for instance an isoxazol-3-ylamino or a 1,2,5-thiadiazol-3-ylamino; heterocyclyl linked through nitrogen (optionally substituted on a carbon other than a carbon atom adjacent to the linking nitrogen ring atom), for instance an optionally 4-substituted 1,2,3-triazol-1-yl; or amidino, for instance an 1-(N-cyanoimino)ethylamino group; such conversions of the hydroxy group taking place directly (for instance by acylation or Mitsunobu reaction) or through the intermediacy of one or more derivatives (for instance a mesylate or an azide);

a silyloxy group may be converted into a hydroxy group or into the groups that may be obtained from a hydroxy group (either directly or through the intermediacy of a hydroxy group);

a keto group may be converted into a hydroxy, thiocarbonyl, oximino, or difluoro group;

a nitro-group may be converted into an amino group and thence by methods that are well known in the art into any of the range common amine derivatives, such as acylamino for instance acetamido group;

a 2-, 4-, or 6-pyridyl or 2-, 4-, or 6-pyrimidyl halide such as chloride or sulfonate such as mesylate substituent may be converted into alkoxy, alkythio, amino, alkylamino, dialkylamino, or N-linked hetero cyclic substituents;

moreover, an optionally substituted heteroaromatic ring D or E may be converted into another heteroaromatic ring D or E by introduction of a new substituent ($R_2a$, $R_3a$, or $R_6a$) or by refunctionalisation of an existing substituent ($R_2a$, $R_3a$, or $R_6a$)

a heterocyclylamino group (optionally substituted or protected on the amino-nitrogen atom) may be converted into another heterocyclyl amino group (optionally substituted or protected on the amino-nitrogen atom) by refunctionalisation, for instance by protection or deprotection, of the amino-nitrogen atom, by introduction of a new ring substituent, or by refunctionalisation of an existing ring substituent;

a heterocyclyl group linked through nitrogen (optionally substituted on a carbon other than a carbon atom adjacent to the linking nitrogen ring atom) may be converted into another heterocyclyl group linked through nitrogen (optionally substituted on a carbon other than a carbon atom adjacent to the linking nitrogen ring atom) by introduction of a new ring substituent or by refunctionalisation of an existing ring substituent, for instance by modifying the 4-substituent of a 4-substituted 1,2,3-triazol-1-yl group;

for instance, examples drawn from the methods for conversion of a hydroxy group into an optionally substituted triazole group are illustrated by the scheme:

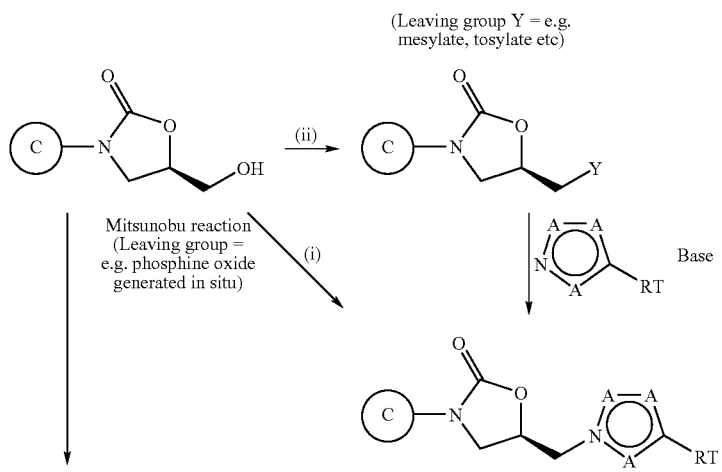

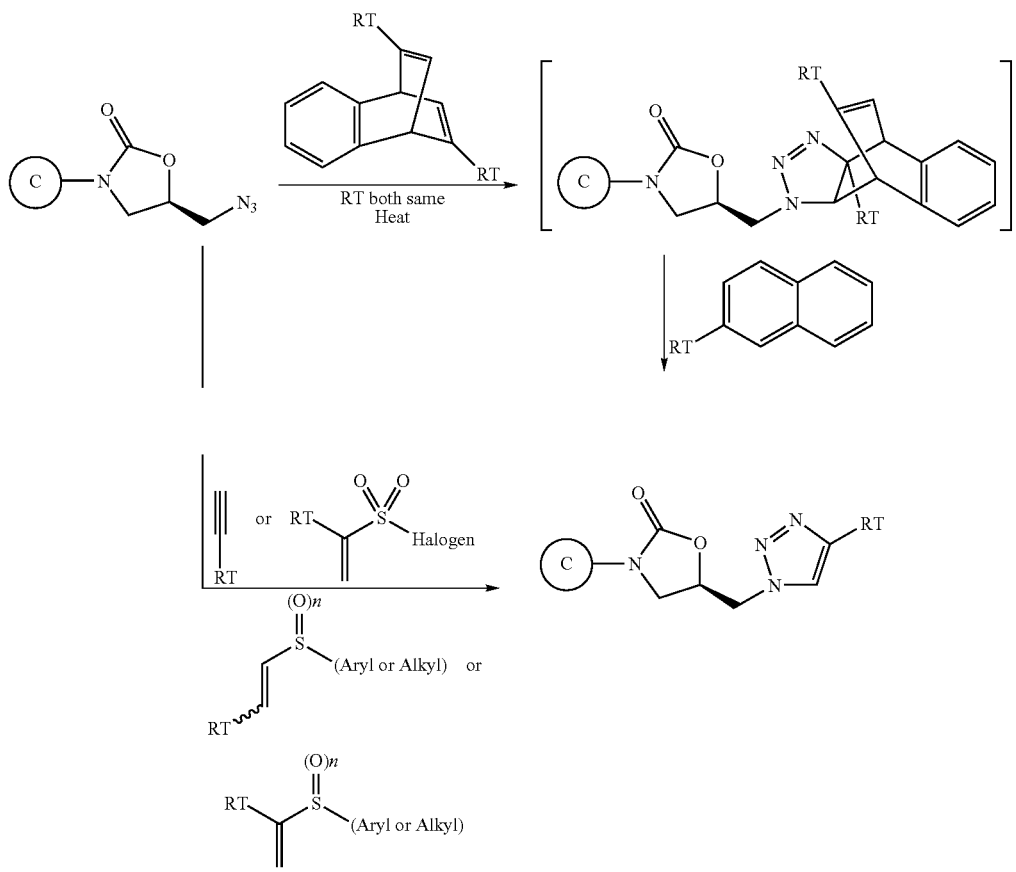

examples drawn from the range of regioselective methods that proceed under very mild conditions are illustrated by processes (h), (i), and (j);

b) by reaction of a molecule of a compound of formula (IIa) [wherein X is a leaving group useful in palladium coupling (for example chloride, bromide, iodide, trifluoromethylsulfonyloxy, trimethylstannyl, trialkoxysilyl, or a boronic acid residue) and in this instance A is either N or C—$R_3$a] with a molecules of a compound of formula (IIb) (wherein X' is a leaving group useful in palladium coupling, for example chloride, bromide, iodide, trifluoromethylsulfonyloxy, trimethylstannyl, trialkoxysilyl, or a boronic acid residue) wherein X and X' are chosen such that an aryl-aryl, heteroaryl-aryl, or heteroaryl-heteroaryl bond replaces the aryl-X (or heteroaryl-X) and aryl-X' (or heteroaryl-X') bonds. Such methods are now well known, see for instance J. K. Stille, *Angew Chem. Int. Ed. Eng.*, 1986, 25, 509-524; N. Miyaura and A Suzuki, *Chem. Rev.*, 1995, 95, 2457-2483, D. Baranano, G. Mann, and J. F. Hartwig, *Current Org. Chem.*, 1997, 1, 287-305, S. P. Stanforth, *Tetrahedron*, 54 1998, 263-303, and P. R. Parry, C. Wang, A. S. Batsanov, M. R. Bryce, and B. Tarbit, *J. Org. Chem.*, 2002, 67, 7541-7543;

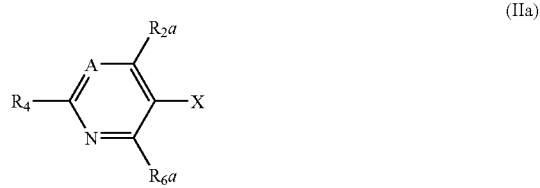

(IIa)

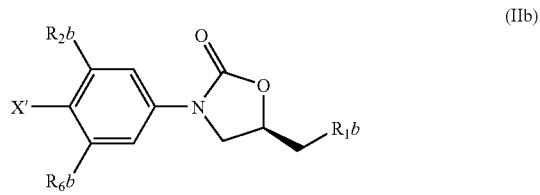

(IIb)

the leaving groups X and X' are chosen to be different and to lead to the desired cross-coupling products of formula (I);

for example

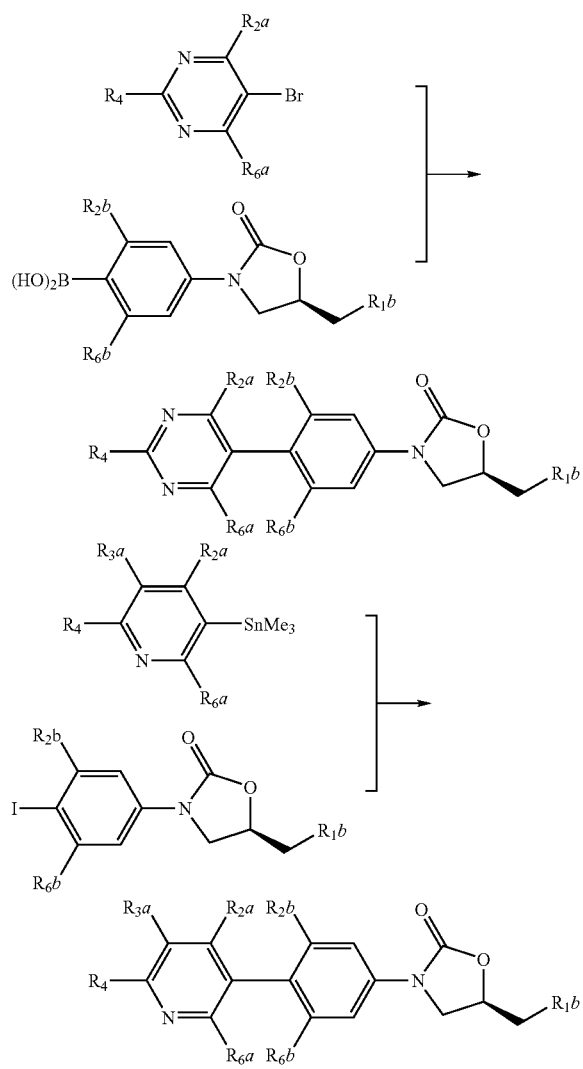

the pyridines, pyrimidines, and aryl oxazolidinones required as reagents for process b) or as intermediates for the preparation of reagents for process b) may be prepared by standard organic methods, for instance by methods analogous to those set out in process sections (c) to (j). Methods for the introduction and interconversion of Groups X and X' are well known in the art.

c) by reaction of a heterobiaryl derivative (III) carbamate with an appropriately substituted oxirane to form an oxazolidinone ring;

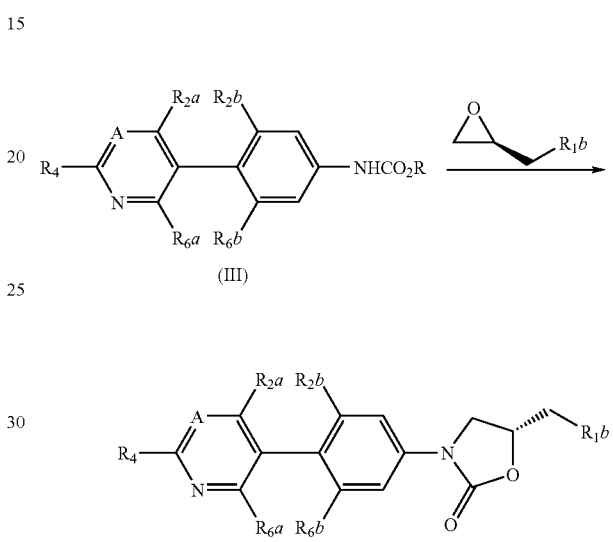

variations on this process in which the carbamate is replaced by an isocyanate or by an amine or/and in which the oxirane is replaced by an equivalent reagent X—CH$_2$CH(O-optionally protected)CH$_2$R$_1$b where X is a displaceable group are also well known in the art.

For example,

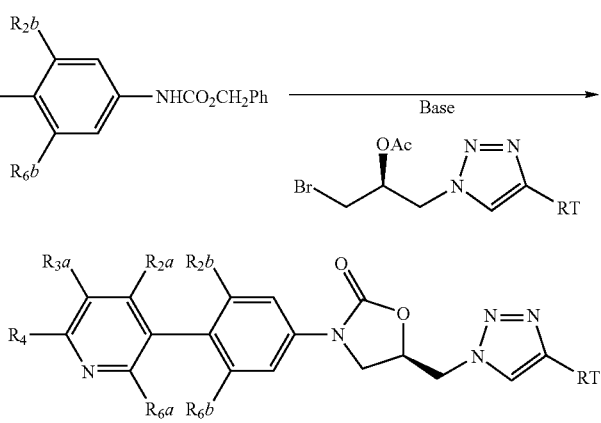

(d) by reaction of a compound of formula (VI):

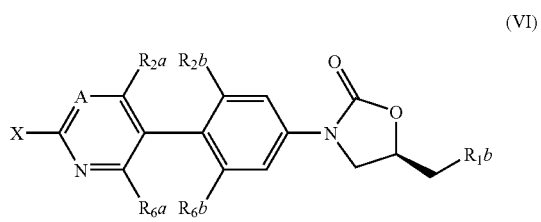
(VI)

where X is a replaceable substituent—such as chloride, bromide, iodide, trifluoromethylsulfonyloxy, trimethylstannyl, trialkoxysilyl, or a boronic acid residue with a compound of the formula (VII):

T-X' (VII)

wherein T-X' is HET3 as herein above defined and X' is a replaceable C-inked substituent—such as chloride, bromide, iodide, trifluoromethylsulfonyloxy, trimethylstannyl, trialkoxysilyl, or a boronic acid residue; wherein the substituents X and X' are chosen to be complementary pairs of substituents known in the art to be suitable as complementary substrates for coupling reactions catalysed by transition metals such as palladium(0);

(d(i)) by reaction catalysed by transition metals such as palladium(0) of a compound of formula (VIII):

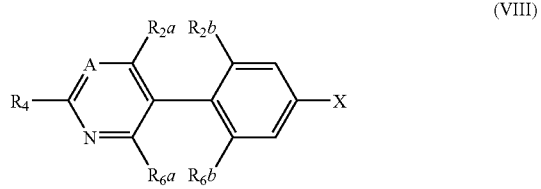
(VIII)

wherein X is a replaceable substituent—such as chloride, bromide, iodide, trifluoromethylsulfonyloxy, trimethylstannyl, trialkoxysilyl, or a boronic acid residue with a compound of the formula (IX) (*Tetrahedron Letts.*, 2001, 42(22), 3681-3684);

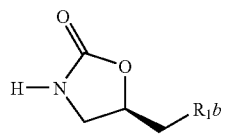
(IX)

(d(ii)) by reaction of a compound of formula (X):

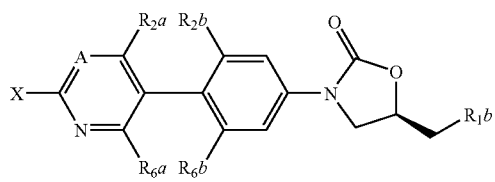
(X)

X is a replaceable substituent—such as chloride, bromide, iodide, trifluoromethylsulfonyloxy—with a compound of the formula (XI):

T-H (XI)

wherein T-H is an amine $R_7R_8NH$, an alcohol $R_{10}OH$, or an azole with an available ring-NH group to give compounds (XIIa), (XIIb), or (XIIc) wherein in this instance A is nitrogen or C—$R_3a$ and A' is nitrogen or carbon optionally substituted with one or more groups R1a;

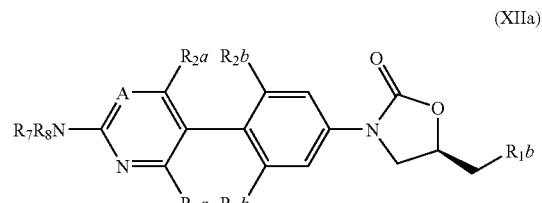
(XIIa)

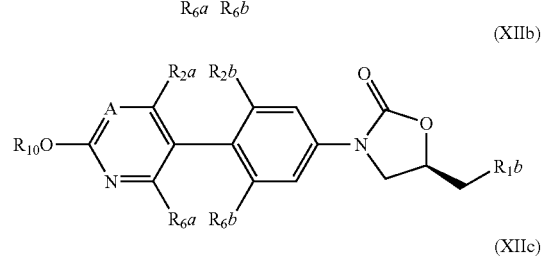
(XIIb)

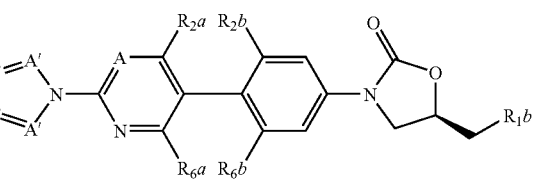
(XIIc)

e) by reaction of a compound of formula (XIII):

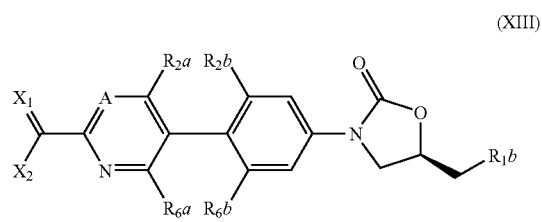
(XIII)

wherein $X_1$ and $X_2$ here are independently optionally substituted heteroatoms drawn in combination from O, N, and S such that $C(X_1)X_2$ constitutes a substituent that is a carboxylic acid derivative substituent with a compound of the formula (XIV) and $X_3$ and $X_4$ are independently optionally substituted heteroatoms drawn in combination from O, N, and S:

(XIV)

and wherein one of $C(X_1)X_2$ and $C(X_3)X_4$ constitutes an optionally substituted hydrazide, thiohydrazide, or amidrazone, hydroximidate, or hydroxamidine and the other one of $C(X_1)X_2$ and $C(X_3)X_4$ constitutes an optionally substituted acylating, thioacylating, or imidoylating agent such that $C(X_1)X_2$ and $C(X_3)X_4$ may be condensed together to form a 1,2,4-heteroatom 5-membered heterocycle containing 3 heteroatoms drawn in combination from O, N, and S, for instance thiadiazole, by methods well-known in the art;

(e (i)) by reaction of a compound of formula (XV):

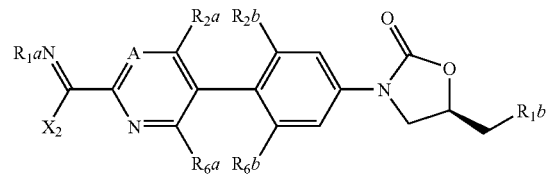

(XV)

wherein $X_2$ is a displaceable group such as ethoxy or diphenylphosphonyloxy with a source of azide anion such as sodium azide to give a tetrazole (XVI)

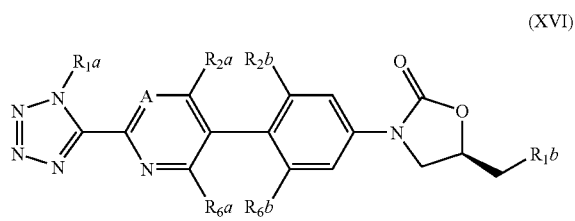

(XVI)

Alternatively nitriles of formula (XVII)

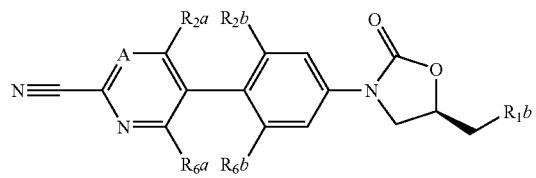

(XVII)

may be reacted directly with azides such as ammonium azide or trialkylstannylazides to give tetrazoles (XVI, R1a=H) that are subsequently alkylated with groups R1a ≠H to give tetrazoles (XVIIIa) and (XVIIIb);

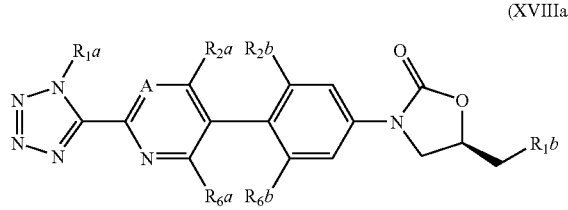

(XVIIIa)

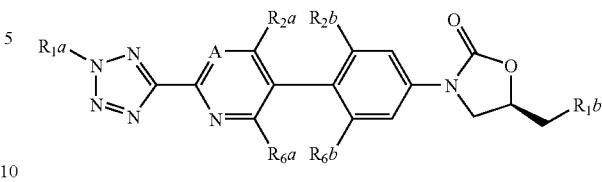

(XVIIIb)

(f) by reaction of a compound of formula (XIX):

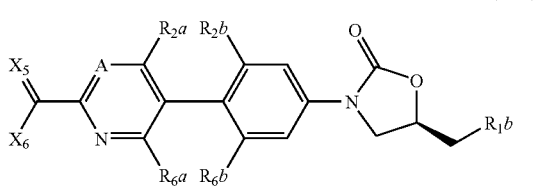

(XIX)

with a compound of the formula (XX):

(XX)

wherein one of $C(X_5)X_6$ and $C(X_7)X_8$ constitutes an optionally substituted alpha-(leaving-group-substituted)ketone, wherein the leaving group is for example a halo-group or an (alkyl or aryl)-sulfonyloxy-group, and the other one of $C(X_5)X_6$ and $C(X_7)X_8$ constitutes an optionally substituted amide, thioamide, or amidine, such that $C(X_5)X_6$ and $C(X_7)X_8$ are groups that may be condensed together to form a 1,3-heteroatom 5-membered heterocycle containing 2 hetero atoms drawn in combination from O, N, and S, for instance thiazole, by methods well-known in the art;

(g) for HET as optionally substituted 1,2,3-triazoles, compounds of the formula (I) may be made by cycloaddition via the azide (wherein e.g. Y in (II) is azide) to acetylenes, or to acetylene equivalents such as optionally substituted cylcohexa-1,4-dienes or optionally substituted ethylenes bearing eliminatable substituents such as arylsulfonyl;

(h) for HET as 4-substituted 1,2,3-triazole compounds of formula (I) may be made by reacting aminomethyloxazolidinones with 1,1-dihaloketone sulfonylhydrazones (Sakai, Kunihazu; Hida, Nobuko; Kondo, Kiyosi; *Bull. Chem. Soc. Jpn.*, 59, 1986, 179-183; Sakai, Kunikazu; Tsunemoto, Daiei; Kobori, Takeo; Kondo, Kiyoshi; Hido, Noboko EP 103840 A2 19840328);

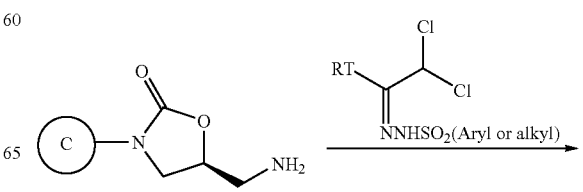

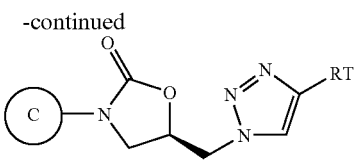
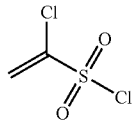

(i) for HET as 4-substituted 1,2,3-triazole compounds of formula (I) may also be made by reacting azidomethyl oxazolidinones with terminal alkynes using Cu(I) catalysis in e.g. aqueous alcoholic solution at ambient temperatures to give 4-substituted 1,2,3-triazoles (V. V. Rostovtsev, L. G. Green, V. V. Fokin, and K. B. Sharpless, Angew. Chem. Int. Ed., 2002, 41, 2596-2599):

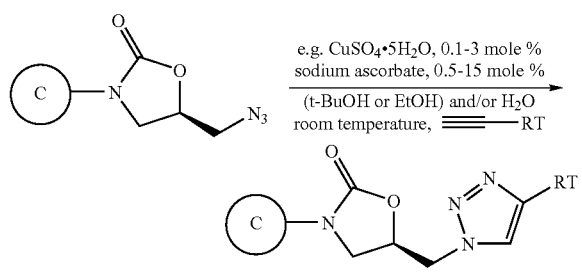

(j) for HET as 4-halogenated 1,2,3-triazole compounds of formula (I) may also be made by reacting azidomethyl oxazolidinones with halovinylsulfonyl chlorides at a temperature between 0° C. and 100° C. either neat or in an inert diluent such as chlorobenzene, chloroform or dioxan.

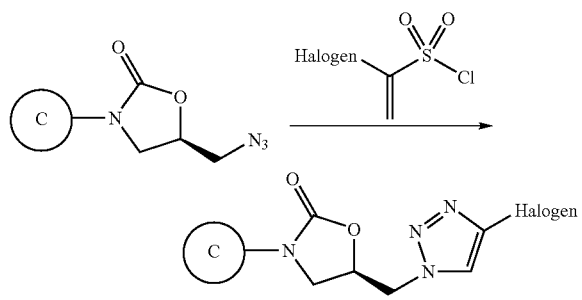

A similar cycloaddition reaction to that shown in (j) with an unrelated azide to give an unrelated triazole has been disclosed in the literature for the case where the halogen in the vinylsulfonylchloride reagent shown above is bromine (C. S. Rondestvedt, Jr. and P. K. Chang, J. Amer. Chem. Soc., 77, 1955, 6532-6540; preparation of 1-bromo-1-ethenesulfonyl chloride by C. S. Rondestvedt, Jr., J. Amer. Chem. Soc., 76, 1954, 1926-1929). However, a reaction of vinylsulfonyl chloride failed to stop at the desired product and gave instead an unwanted by-product. Moreover, the factors that govern the formation of either the undesired triazole by elimination of the elements of H-Halogen from the intermediate cycloadduct or the desired triazole by elimination of the elements of HCl and $SO_2$ from the intermediate cycloadduct are not set out in the literature.

We have now surprisingly found that, when the halogen is chlorine, that is when the reagent is the compound 1-chloro-1-ethenesulfonyl chloride the cycloaddition reaction is highly regioselective and gives a good yield of the desired product. Furthermore the reagent 1-chloro-1-ethenesulfonyl chloride is novel. Therefore a further aspect of the invention comprises the compound 1-chloro-1-ethenesulfonyl chloride. Another aspect of the invention comprises the use of 1-chloro-1-ethenesulfonyl chloride in a cycloaddition reaction with an azide to form a 4-chloro-1,2,3-triazole. A further aspect of the invention comprises use of 1-chloro-1-ethenesulfonyl chloride with an azide derivative in a process to form a compound of the formula (I) wherein $R_1b$ is 4-chloro-1,2,3-triazole, or R4 is 4-chloro-HET3-AB.

The cycloaddition reaction with 1-chloro-1-ethenesulfonyl chloride with an azide derivative in a process to form a compound of the formula (I) wherein $R_1b$ is 4-chloro-1,2,3-triazole and or $R_4$ is 4-chloro-HET3-AB is carried out at 0° C. and 100° C., preferably at room temperature, either in an inert solvent, preferably chlorobenzene, chloroform, or dioxan, or more preferably without a solvent.

The removal of any protecting groups, the formation of a pharmaceutically-acceptable salt and/or the formation of an in-vivo hydrolysable ester are within the skill of an ordinary organic chemist using standard techniques. Furthermore, details on the these steps, for example the preparation of in-vivo hydrolysable ester prodrugs has been provided, for example, in the section above on such esters.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

According to a further feature of the invention there is provided a compound of the invention, or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the invention, or a pharmaceutically-acceptable salt, or in-vivo hydrolysable ester thereof, for use as a medicament; and the use of a compound of the invention of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the invention, an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the invention, an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration as eye-drops, for administration by inhalation (for example as a finely divided powder or a liquid aerosol), for administration by insufflation (for example as a finely divided powder) or for parenteral administration (for example as a sterile aqueous or oily solution for intravenous, subcutaneous, sub-lingual, intramuscular or intramuscular dosing or as a suppository for rectal dosing).

In addition to the compounds of the present invention, the pharmaceutical composition of this invention may also contain (ie through co-formulation) or be co-administered (simultaneously, sequentially or separately) with one or more known drugs selected from other clinically useful antibacterial agents (for example, β-lactams, macrolides, quinolones or aminoglycosides) and/or other anti-infective agents (for example, an antifungal triazole or amphotericin). These may include carbapenems, for example meropenem or imipenem, to broaden the therapeutic effectiveness. Compounds of this invention may also be co-formulated or co-administered with bactericidal/permeability-increasing protein (BPI) products or efflux pump inhibitors to improve activity against gram negative bacteria and bacteria resistant to antimicrobial agents. Compounds of this invention may also be co-formulated or co-administered with a vitamin, for example Vitamin B, such as Vitamin B2, Vitamin B6, Vitamin B12 and folic acid. Compounds of the invention may also be formulated or co-administered with cyclooxygenase (COX) inhibitors, particularly COX-2 inhibitors.

In one aspect of the invention, a compound of the invention is co-formulated with an antibacterial agent which is active against gram-positive bacteria.

In another aspect of the invention, a compound of the invention is co-formulated with an antibacterial agent which is active against gram-negative bacteria.

In another aspect of the invention, a compound of the invention is co-administered with an antibacterial agent which is active against gram-positive bacteria.

In another aspect of the invention, a compound of the invention is co-administered with an antibacterial agent which is active against gram-negative bacteria.

The compositions of the invention may be obtained by conventional procedures using conventional pharmaceutical excipients, well known in the art. Thus, compositions intended for oral use may contain, for example, one or more colouring, sweetening, flavouring and/or preservative agents. A pharmaceutical composition to be dosed intravenously may contain advantageously (for example to enhance stability) a suitable bactericide, antioxidant or reducing agent, or a suitable sequestering agent.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol. Solubility enhancing agents, for example cyclodextrins may be used.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 50 mg to 5 g of active agent compounded with an appropriate and convenient amount of excipients which may vary from about 5 to about 98 percent by weight of the total composition. Dosage unit forms will generally contain about 200 mg to about 2 g of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg$^{-1}$ to 20 mgkg$^{-1}$ of a compound of this invention, the composition being administered 1 to 4 times per day. In another embodiment a daily dose of 5 mgkg$^{-1}$ to 20 mgkg$^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

In the above other, pharmaceutical composition, process, method, use and medicament manufacture features, the alternative and preferred embodiments of the compounds of the invention described herein also apply.

Antibacterial Activity:

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of *S. aureus* and coagulase negative staphylococci, together with *haemophilus* and *moraxella* strains. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of $10^4$ CFU/spot. Typically, compounds are active in the range 0.01 to 256 µg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms. Fastidious Gram negative organisms were tested in Mueller-Hinton broth supplemented with hemin and NAD, grown aerobically for 24 hours at 37° C., and with an innoculum of $5 \times 10^4$ CFU/well.

For example, the following results were obtained for the compound of Example 1:

| Organism | | MIC (µg/ml) |
|---|---|---|
| *Staphylococcus aureus*: | MSQS | 0.25 |
| | MRQR | 0.25 |
| *Streptococcus pneumoniae* | | <0.06 |
| *Enterococcus faecium* | | 0.25 |
| *Haemophilus influenzae* | | 2 |
| *Moraxella catarrhalis* | | 0.25 |
| Linezolid Resistant *Streptococcus pneumoniae* | | 0.5 |

MSQS = methicillin sensitive and quinolone sensitive
MRQR = methicillin resistant and quinolone resistant Certain intermediates and/or Reference Examples described hereinafter are within the scope of the invention and may also possess useful activity, and are provided as a further feature of the invention.

The invention is now illustrated but not limited by the following Examples in which unless otherwise stated:

(i) evaporations were carried out by rotary evaporation in-vacuo and work-up procedures were carried out after removal of residual solids by filtration;

(ii) operations were carried out at ambient temperature, that is typically in the range 18-26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the invention were generally confirmed by NMR and mass spectral techniques [proton magnetic resonance spectra were generally determined in DMSO-$d_6$ unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected]; optical rotations were determined at 589 nm at 20° C. for 0.1M solutions in methanol using a Perkin Elmer Polarimeter 341;

(vi) each intermediate was purified to the standard required for the subsequent stage and was characterised in sufficient detail to confirm that the assigned structure was correct; purity was assessed by HPLC, TLC, or NMR and identity was determined by infra-red spectroscopy (IR), mass spectroscopy or NMR spectroscopy as appropriate; NOE is nuclear overhauser effect;

(vii) in which the following abbreviations may be used:

DMF is N,N-dimethylformamide; DMA is N,N-dimethylacetamide; TLC is thin layer chromatography; HPLC is high pressure liquid chromatography; MPLC is medium pressure liquid chromatography; NMP is N-methylpyrrolidone; DMSO is dimethylsulfoxide; $CDCl_3$ is deuterated chloroform; MS is mass spectroscopy; ESP is electrospray; EI is electron impact; CI is chemical ionisation; APCI is atmospheric pressure chemical ionisation; EtOAc is ethyl acetate; MeOH is methanol; phosphoryl is $(HO)_2$—P(O)—O—; phosphiryl is $(HO)_2$—P—O—; Bleach is "Clorox" 6.15% sodium hypochlorite; THF is tetrahydrofuran (viii) temperatures are quoted as ° C.

EXAMPLE 1

(5R)-3-(3-Fluoro-4-(6-(2-methyl-2H-tetrazol-5-yl) pyrid-3-yl)phenyl)-5-(1H-1,2,3-triazol-1-ylmethyl)-1,3-oxazolidin-2-one

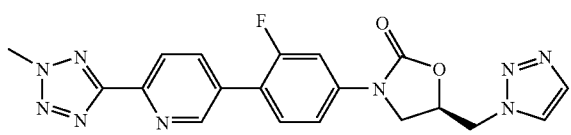

A mixture of (5R)-3-(3-fluoro-4-iodophenyl)-5-(1H-1,2,3-triazol-1-ylmethyl)-1,3-oxazolidin-2-one (370 mg, 0.95 mmol), bis(pinacolato)diboron (605 mg, 2.4 mmol), and potassium acetate (326 mg, 3.3 mmol) in dimethylsulfoxide (5 mL) was degassed, flushed with nitrogen and trated with dichloro[1,1']bis(diphenylphosphino)ferrocene]palladium (II) dichloromethane adduct (69 mg, 10 mol %). The mixture was heated to 80° C. for 1.5 hours, cooled to room temperature, filtered through Celite, and extracted with ethyl acetate. The organic phase was washed with aqueous ammonium chloride solution, dried over magnesium sulfate, and evaporated to dryness. The involatile residue was purified by chromatography on silica-gel [elution with hexanes:ethyl acetate (3:2)] to give a mixture of (5R)-3-(3-fluoro-4-(4,4,5,5-tetramethyl-1,3,2-dioxaborolan-2-yl)phenyl)-5-(1H-1,2,3-triazol-1-ylmethyl)-1,2-oxazolidin-2-one and the corresponding boronic acid (210 mg, ~0.54 mmol, 57%) that was used without further purification.

A mixture of the mixture of boronate ester and boronic acid prepared above, 5-bromo-2-(2-methyl-2H-tetrazol-5-yl)pyridine (160 mg, 0.67 mmol), and potassium carbonate (448 mg, 3.24 mmol) in N,N-dimethyl formamide and water (10 mL, 7:1) was degassed, flushed with nitrogen, and treated with tetrakis (triphenylphospine) palladium (0) (62 mg, 0.054 mmol). The reaction mixture was heated at 80° C. for 1.5 hours, cooled to room temperature, filtered through Celite, extracted with ethyl acetate, dried over magnesium sulfate, and evaporated to dryness. The involatile residue was purified by chromatography on silica-gel [elution with ethyl acetate: hexanes (3:2)] to give the product as a colorless amorphous solid (140 mg, 61%).

MS (ESP): 422.47 ($MH^+$) for $C_{19}H_{16}FN_9O_2$ $^1$H-NMR (DMSO-$d_6$) δ: 3.98 (dd, 1H); 4.31 (dd, 1H); 4.47 (s, 3H); 4.86 (m, 2H); 5.18 (m, 1H); 7.45 (m, 1H); 7.61 (m, 1H); 7.74 (m, 1H); 7.77 (brs, 1H); 8.12-8.27 (m, 3H); 8.93 (s, 1H).

The intermediates for Example 1 were prepared as follows:

Acetic acid (5R)-3-(3-fluorophenyl)-1,3-oxazolidin-2-on-5-ylmethyl ester

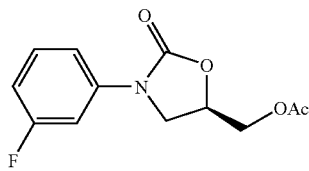

(5R)-3-(3-Fluorophenyl)-5-hydroxymethyl-1,3-oxazolidin-2-one (40 g, 0.189 M, see Upjohn WO 94-13649) was suspended by stirring in dry dichloromethane (400 mL) under nitrogen. Triethylamine (21 g, 0.208 M) and 4-dimethylaminopyridine (0.6 g, 4.9 mM) were added, followed by dropwise addition of acetic anhydride (20.3 g, 0.199 M) over 30 minutes, and stirring continued at ambient temperature for 18 hours. Saturated aqueous sodium bicarbonate (250 mL) was added, the organic phase separated, washed with 2% sodium dihydrogen phosphate, dried (magnesium sulfate), filtered and evaporated to give the desired product (49.6 g) as an oil.

MS (ESP): 254 ($MH^+$) for $C_{12}H_{12}FNO_4$

NMR ($CDCl_3$) δ: 2.02 (s, 3H); 3.84 (dd, 1H); 4.16 (t, 1H); 4.25 (dd, 1H); 4.32 (dd, 1H); 4.95 (m, 1H); 6.95 (td, 1H); 7.32 (d, 1H); 7.43 (t, 1H); 7.51 (d, 1H).

Acetic acid (5R)-3-(3-fluoro-4-iodo-phenyl)-1,3-oxazolidin-2-one-5-ylmethyl ester

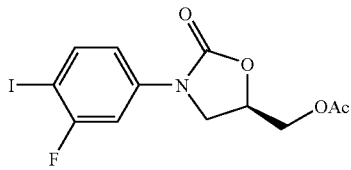

Acetic acid (5R)-3-(3-fluoro-phenyl)-1,3-oxazolidin-2-one-5-ylmethyl ester (15.2 g, 60 mM) was dissolved in a mixture of chloroform (100 mL) and acetonitrile (100 mL) under nitrogen, and silver trifluoroacetate (16.96 g, 77 mM) added. Iodine (18.07 g, 71 mM) was added in portions over 30 minutes to the vigorously stirred solution, and stirring continued at ambient temperature for 18 hours. As reaction was not complete, a further portion of silver trifluoroacetate (2.64 g, 12 mM) was added and stirring continued for 18 hours. After filtration, the mixture was added to sodium thiosulfate solution (3%, 200 mL) and dichloromethane (200 mL), and the organic phase separated, washed with sodium thiosulfate (200 mL), saturated aqueous sodium bicarbonate (200 mL), brine (200 mL), dried (magnesium sulfate), filtered and evaporated. The crude product was suspended in isohexane (100 mL), and sufficient diethyl ether added to dissolve out the brown impurity while stirring for 1 hour. Filtration gave the desired product (24.3 g) as a cream solid.

MS (ESP): 380 (MH$^+$) for $C_{12}H_{11}FINO_4$

NMR (DMSO-$d_6$) δ: 2.03 (s, 3H); 3.82 (dd, 1H); 4.15 (t, 1H); 4.24 (dd, 1H); 4.30 (dd, 1H); 4.94 (m, 1H); 7.19 (dd, 1H); 7.55 (dd, 1H); 7.84 (t, 1H).

(5R)-3-(3-Fluoro-4-iodophenyl)-5-hydroxymethyl-1,3-oxazolidin-2-one

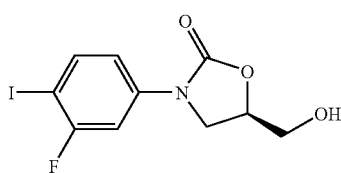

Acetic acid (5R)-3-(3-fluoro-4-iodophenyl)-1,3-oxazolidin-2-one-5-ylmethyl ester (30 g, 79 mM) was treated with potassium carbonate (16.4 g, 0.119 mM) in a mixture of methanol (800 mL) and dichloromethane (240 mL) at ambient temperature for 25 minutes, then immediately neutralised by the addition of acetic acid (10 mL) and water (500 mL). The precipitate was filtered, washed with water, and dissolved in dichloromethane (1.2 L), the solution washed with saturated sodium bicarbonate, and dried (magnesium sulfate). Filtration and evaporation gave the desired product (23 g).

MS (ESP): 338 (MH$^+$) for $C_{10}H_9FINO_3$

NMR (DMSO-$d_6$) δ: 3.53 (m, 1H); 3.67 (m, 1H); 3.82 (dd, 1H); 4.07 (t, 1H); 4.70 (m, 1H); 5.20 (t, 1H); 7.21 (dd, 1H); 7.57 (dd, 1H); 7.81 (t, 1H).

(5R)-5-Azidomethyl-3-(3-fluoro-4-iodophenyl)-1,3-oxazolidin-2-one

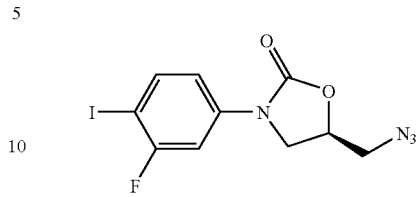

Methanesulfonyl chloride (17.9 mL) was added dropwise to a stirred solution of (5R)-3-(3-fluoro-4-iodophenyl)-5-hydroxymethyl-1,3-oxazolidin-2-one (55.8 g) and triethylamine (46.1 mL) in dry dichloromethane (800 mL) under an atmosphere of dry nitrogen and maintained below room temperature by an ice-bath. The stirred reaction mixture was allowed to warm to room temperature during 3 hours and then washed sequentially with water and brine and then dried ($Na_2SO_4$). Solvent was removed under reduced pressure to give the intermediate mesylate as a yellow solid (68 g) that was used without further purification. A stirred solution in DMF (800 mL) of a mixture of the intermediate mesylate (68 g) and sodium azide (32.3 g) was heated at 75° C. overnight. The mixture was allowed to cool to room temperature, diluted with water, and extracted twice with ethyl acetate. The combined extracts were washed sequentially with water and brine, and then dried ($Na_2SO_4$). Solvent was removed under reduced pressure to give a yellow oil that was purified by column chromatography on silica-gel [elution with ethyl acetate:hexanes (1:1)] to give the product azide as an off-white solid (49 g). The product could be further purified by trituration with ethyl acetate/hexanes.

$^1$H-NMR (DMSO-$d_6$) δ: 3.57-3.64 (dd, 1H); 3.70-3.77 (dd, 1H); 3.81-3.87 (dd, 1H); 4.06 (t, 1H); 4.78-4.84 (m, 1H); 7.05-7.09 (ddd, 1H); 7.45 (dd, 1H); 7.68-7.74 (dd, 1H).

(5R)-3-(3-Fluoro-4-iodophenyl)-5-(1H-1,2,3-triazol-1-ylmethyl)-1,3-oxazolidin-2-one

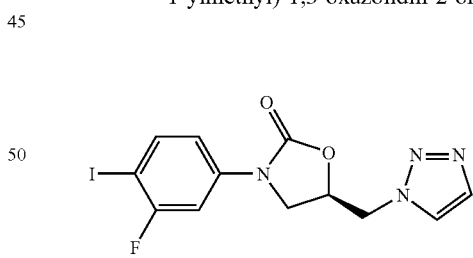

A stirred solution in dioxan (300 mL) of a mixture of the (5R)-5-azidomethyl-3-(3-fluoro-4-iodophenyl)-1,3-oxazolidin-2-one (30 g) and bicyclo[2.2.1]heptadiene (30 mL) was heated under reflux overnight. The mixture was allowed to cool to room temperature and then evaporated to dryness under reduced pressure to give a brown solid. The brown solid was purified by column chromatography on silica-gel [elution with a gradient from 98:2 to 95:5 methanol:chloroform] to give the product triazole as a pale yellow solid (20 g). The product could be further purified by trituration with dichloromethane/hexanes (1:1) to give an off-white solid.

¹H-NMR (DMSO-d₆) δ: 3.86-3.92 (dd, 1H); 4.23 (t, 1H); 4.83 (d, 2H); 5.11-5.19 (m, 1H); 7.12-7.16 (dd, 1H); 7.47-7.51 (dd, 1H); 7.76 (s, 1H); 7.79-7.85 (dd, 1H); 8.16 (s, 1H).

3-Bromo-6-cyano-pyridine

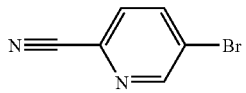

A stirred solution of 2,5-dibromopyridine (39.465 g, 0.17 mol) in anhydrous NMP (100 mL) was treated with CuCN (14.42 g, 0.17 mol) for 20 hours at 110° C. under nitrogen. The reaction mixture was cooled to 40° C. and treated with aqueous sodium hydroxide (2M; 200 mL) and then with ethyl acetate (200 mL). The mixture was stirred for 1 hour and then filtered through Celite to remove the resulting precipitate. The retained solid was washed with aqueous sodium hydroxide (2M; 600 mL) and then with ethyl acetate (600 mL). The organic layers were combined and washed with aqueous ammonium hydroxide (5M; 800 mL), dried over magnesium sulfate, and evaporated to dryness under reduced pressure. The involatile residue was purified by chromatography on silica gel [elution gradient 1% to 7% of ethyl acetate in hexanes] to give the title compound (8.538 g, 28%), as a colorless amorphous solid.

¹H-NMR (DMSO-d₆) (300 MHz) δ 8.05 (d, 1H); 8.40 (dd, 1H); 8.95 (d, 1H).

5-Bromo-2-tetrazol-5-ylpyridine

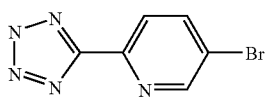

A mixture of 3-bromo-6-cyano-pyridine (2 g, 10.9 mmol), sodium azide (0.85 g, 13 mmol), and ammonium chloride (0.59 g, 11 mmol) in N,N-dimethylformamide (20 mL) was heated for 1 h at 120° C. The reaction mixture was diluted with ethyl acetate (~100 mL) and the product was isolated by filtration and then washed with ethyl acetate to give the title compound, an off-white amorphous solid which was used in the next step without further purification.

5-Bromo-2-(2-methyl-2H-tetrazol-5-yl)pyridine and 5-bromo-2-(1-methyl-1H-tetrazol-5-yl)pyridine

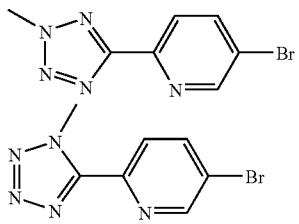

5-Bromo-2-(2-methyl-2H-tetrazol-5-yl)pyridine and 5-bromo-2-(1-methyl-1H-tetrazol-5-yl)pyridine were prepared according to the procedure described by Dong A Pharmaceuticals (WO 01/94342).

A mixture of 6.5 g unpurified 5-bromo-2-tetrazol-5-ylpyridine [Dong A Pharmaceuticals (WO 01/94342)] (~28 mmol) and sodium hydroxide (9 g, 125 mmol) in dry DMF was evaporated to dryness under reduced pressure. A stirred solution of the involatile residue in dry DMF (50 mL) was treated dropwise at ice-bath temperature with iodomethane (3.0 mL, 48 mmol). The stirred reaction mixture was allowed to warm and then maintained at room temperature for 2 hours. The reaction mixture was partitioned between iced water and ethyl acetate. The organic phase was washed with water, dried over magnesium sulfate, and then evaporated under reduced pressure to give a residue that was purified by chromatography on silica gel [elution with dichloromethane:ethyl acetate (60:1)] to give:
1. 5-bromo-2-(1-methyl-1H-tetrazol-5-yl)pyridine (1.397 g), a colorless solid, (TLC: silica-gel, hexanes:ethyl acetate (4:1), Rf: 0.3), ¹H-NMR (DMSO-d₆) (300 MHz) δ: 4.38 (s, 3H); 8.17 (d, 1H); 8.35 (dd, 1H); 8.96 (d, 1H).
2. 5-bromo-2-(2-methyl-2H-tetrazol-5-yl)pyridine (1.07 g), a colorless solid, (TLC: silica-gel, hexanes:ethyl acetate (4:1), Rf: 0.1). ¹H-NMR (DMSO-d₆) (300 MHz) δ: 4.46 (s, 3H); 8.09 (d, 1H); 8.28 (dd, 1H); 8.88 (d, 1H).

Structure assignment based on nmr HMBC (Heteronuclear Multiple Bond Correlation) experiments, in which long range coupling of the protons of CH₃ to the C5 of the tetrazole ring is observed in the 1-methyl-1H-isomer of Rf 0.3, but not in the 2-methyl-2H-isomer of Rf 0.1). The compound referred to as 5-bromo-2-(1-methyl-1H-tetrazol-5-yl)pyridine is thus the isomer of Rf 0.3 and the compound referred to as 5-bromo-2-(2-methyl-2H-tetrazol-5-yl)pyridine is thus the isomer of Rf 0.1

EXAMPLE 2

(5R)-3-(3-Fluoro-4-(6-(2-methyl-2H-tetrazol-5-yl)pyrid-3-yl)phenyl)-5-(4-fluoromethyl-1H-1,2,3-triazol-1-ylmethyl)-1,3-oxazolidin-2-one

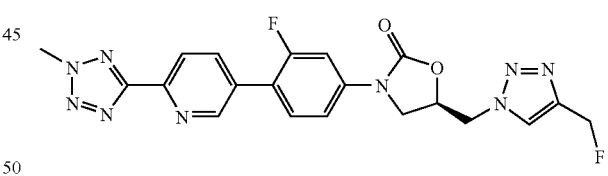

A mixture of (5R)-3-(3-fluoro-4-iodophenyl)-5-(4-fluoromethyl-1H-1,2,3-triazol-1-ylmethyl)-1,3-oxazolidin-2-one (1.5 g, 3.57 mmol), bis(pinacolato)diboron (2.26 g, 8.9 mmol), and potassium acetate (1.22 g, 12.5 mmol) in dimethylsulfoxide (15 mL) was treated with dichloro[1,1']bis(diphenylphosphino)ferrocene]palladium (II) dichloromethane adduct (261 mg, 10 mol %) and allowed to react as described for Example 1. The reaction mixture was purified by chromatography on silica gel [elution with hexanes:ethyl acetate (3:2)] to give a mixture of (5R)-3-(3-fluoro-4-(4,4,5,5-tetramethyl-1,3,2-dioxaborolan-2-yl)phenyl)-5-(4-fluoromethyl-1H-1,2,3-triazol-1-ylmethyl)-1,3-oxazolidin-2-one with the corresponding boronic acid (562 mg, ~37%) that was sufficiently pure for further use.

A mixture of a portion of the mixture of boronate ester and boronic acid prepared above (337 g, 0.8 mmol), 5-bromo-2-

(2-methyl-2H-tetrazol-5-yl)pyridine (175 mg, 0.73 mmol), and potassium carbonate (504 mg, 3.65 mmol) in N,N-dimethylformamide:water (10 mL, 7:1) was treated with tetrakis(triphenylphospine) palladium (0) (84 mg, 10 mol %) and allowed to react as described for Example 1. The reaction mixture was purified by chromatography on silica gel [elution with ethyl acetate:hexanes (1:2)] to give the product as a colorless amorphous solid (180 mg, 49%).

MS (ESP): 454.45 (MH$^+$) for $C_{20}H_{17}F_2N_9O_2$ $^1$H-NMR (DMSO-d$_6$) δ: 3.98 (dd, 1H); 4.32 (dd, 1H); 4.47 (s, 3H); 4.88 (m, 2H); 5.19 (m, 1H); 5.46 (d, 2H, $J_{H,F}$ 48 Hz); 7.45 (m, 1H); 7.63 (m, 1H); 7.75 (m, 1H); 8.15-8.24 (m, 2H); 8.38 (d, 1H); 8.93 (s, 1H).

The intermediates for Example 2 were prepared as follows:

(5R)-3-(3-Fluoro-4-iodophenyl)-5-(4-hydroxymethyl-1H-1,2,3-triazol-1-ylmethyl)-1,3-oxazolidin-2-one

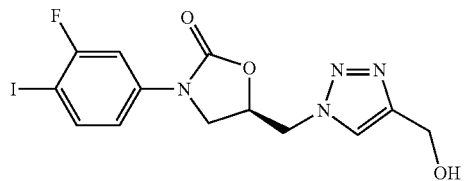

A mixture of (5R)-3-(3-fluoro-4-iodophenyl)-5-azidomethyl-1,3-oxazolidin-2-one (10 g, 28 mmol) and propargyl alcohol (3.2 mL, 56 mmol) in acetonitrile (80 mL) was treated with CuI (526 mg, 2.8 mmol) and then stirred overnight. The solidified reaction mixture was extracted with ethyl acetate:acetonitrile, washed with water, and dried over magnesium sulfate, and then evaporated under reduced pressure to give a crude product sufficiently pure for further use (12.3 g, quantitative).

MS (ESP): 419.13 (MH$^+$) for $C_{13}H_{12}FIN_4O_3$ $^1$H-NMR (DMSO-d$_6$) δ: 3.88 (dd, 1H); 4.23 (dd, 1H); 4.51 (d, 2H); 4.80 (m, 2H); 5.14 (m, 1H); 5.22 (dd, 1H); 7.16 (m, 1H); 7.51 (m, 1H); 7.83 (m, 1H); 8.01 (d, 1H).

(5R)-3-(3-Fluoro-4-iodophenyl)-5-(4-bromomethyl-1H-1,2,3-triazol-1-ylmethyl)-1,3-oxazolidin-2-one

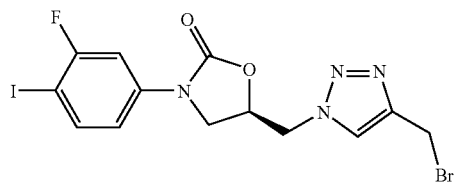

A stirred mixture of (5R)-3-(3-fluoro-4-iodophenyl)-5-(4-hydroxymethyl-1H-1,2,3-triazol-1-ylmethyl)-1,3-oxazolidin-2-one (14.7 g, 35.1 mmol) and carbon tetrabromide (12.16 g, 36.7 mmol) in dichloromethane (1 L) was treated at 0° C. with triphenylphosphine (12.34 g, 61.2 mmol). The reaction mixture was stirred for 30 minutes at 0° C. and then at room temperature overnight. The reaction mixture was applied onto a silica-gel column and eluted with hexanes:ethyl acetate (1:1) and then with ethyl acetate:methanol (95: 5) to give a product that was further purified by recrystallization from ethyl acetate to give the title compound as a colorless solid (14 g).

MS (ESP): 482.69 (MH$^+$ for Br$^{81}$) for $C_{13}H_{11}BrFIN_4O_2$ $^1$H-NMR (DMSO-d$_6$) δ: 3.87 (dd, 1H); 4.23 (dd, 1H); 4.74 (s, 2H); 4.81 (m, 2H); 5.12 (m, 1H); 7.14 (m, 1H); 7.49 (m, 1H); 7.81 (m, 1H); 8.22 (d, 1H).

(5R)-3-(3-fluoro-4-iodophenyl)-5-[(4-fluoromethyl-1H-1,2,3-triazol-1-yl)methyl]oxazolidin-2-one

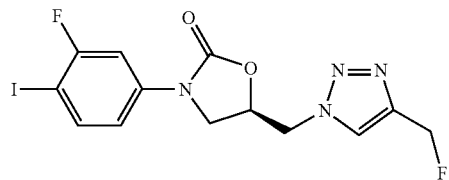

A mixture of (5R)-3-(3-fluoro-4-iodophenyl)-5-(4-bromomethyl-1H-1,2,3-triazol-1-ylmethyl)-1,3-oxazolidin-2-one (6.94 g, 14.4 mmol), potassium fluoride (4.19 g, 72.1 mmol), and 1-butyl-3-methylimidazolium tetrafluoroborate (18.4 mL) in acetonitrile (250 mL) and water (1.5 mL) was heated to 90° C. overnight. The reaction mixture was diluted with ethyl acetate, washed with water, dried over magnesium sulfate, and evaporated to dryness. The involatile residue was purified by chromatography on silica gel [elution with ethyl acetate] gave the title compound as an off-white amorphous solid (2.7 g, 45%).

MS (ESP): 421.34 (MH$^+$) for $C_{13}H_{11}F_2IN_4O_2$ $^1$H-NMR (DMSO-d$_6$) δ: 3.88 (dd, 1H); 4.23 (dd, 1H); 4.84 (m, 2H); 5.14 (m, 1H); 5.45 (d, 2H, $J_{H,F}$ 52 Hz); 7.14 (m, 1H); 7.49 (m, 1H); 7.81 (m, 1H); 8.34 (d, 1H).

EXAMPLE 3

(5R)-3-(3-Fluoro-4-(6-(2-methyl-2H-tetrazol-5-yl)pyrid-3-yl)phenyl)-5-(4-chloro-1H-1,2,3-triazol-1-ylmethyl)-1,3-oxazolidin-2-one

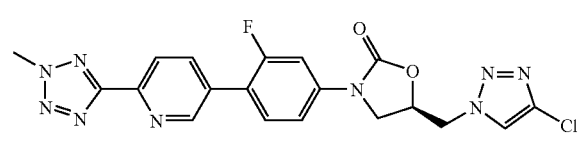

A mixture of (5R)-3-(3-fluoro-4-(4,4,5,5-tetramethyl-1,3,2-dioxaborolan-2-yl)phenyl)-5-(4-chloro-1H-1,2,3-triazol-1-ylmethyl)-1,3-oxazolidin-2-one (300 mg, 0.71 mmol), 5-bromo-2-(2-methyl-2H-tetrazol-5-yl)pyridine (170 mg, 0.71 mmol), and sodium carbonate (226 mg, 2.13 mmol) in N,N-dimethylformamide:water (5 mL, 10:1) was degassed, flushed with nitrogen, and treated with tetrakis(triphenylphosphine)palladium (0) (82 mg, 10 mol %). The reaction mixture was heated at 70° C. for 3 hours, cooled to room temperature, and evaporated to dryness under reduced pressure. The involatile residue was purified by chromatography on silica gel [elution with dichloromethane:N,N-dimethylformamide (25:1 to 20:1)]. The product fraction was concentrated to a small volume (~3 mL) and treated with dichloromethane (5 mL) and hexanes (15 mL) to precipitate the product as a colorless amorphous solid (229 mg, 71%).

MS (ESP): 456.27 (MH$^+$) for $C_{19}H_{15}FN_9O_2$ $^1$H-NMR (DMSO-d$_6$) δ: 3.98 (dd, 1H); 4.32 (dd, 1H); 4.47 (s, 3); 4.86 (m, 2H); 5.19 (m, 1H); 7.46 (m, 1H); 7.63 (m, 1H); 7.76 (m, 1H); 8.15-8.27 (m, 2H); 8.47 (s, 1H); 8.93 (s, 1H).

The intermediates for Example 3 were prepared as follows:

Ethenesulfonyl Chloride

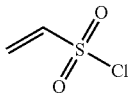

A stirred solution of 2-chloroethanesulfonyl chloride (50 g, 0.307 mol) in dry ether (400 mL) was treated at −60° C. to −50° C. under an atmosphere of nitrogen with a solution of 2,6-lutidine (42.2 mL, 0.36 mol) in dry ether (60 mL) and then with a further portion of dry ether (200 mL). The stirred reaction mixture was allowed to warm to room temperature, cooled to 0° C. and then treated slowly with dilute aqueous sulfuric acid (1%; 125 mL). The ethereal phase was separated, washed with dilute aqueous sulfuric acid (1%; 125 mL) and brine (2×120 mL), dried over magnesium sulfate, and concentrated under reduced pressure (500 mmHg) to give a crude oil that was purified by distillation to give ethenesulfonyl chloride (C. S. Rondestveldt, *J. Amer. Chem. Soc.*, 76, 1954, 1926) (24.6 g, 63%), b.p. 27.2° C./0.2 mmHg.

$^1$H- nmr (CDCl$_3$) δ 7.20 (dd, J=16.2 and 9.4 Hz, 1H), 6.55 (dd, J=16.2 and 1.7 Hz, 1H), and 6.24 (dd, J=9.4 and 1.7 Hz, 1H).

1,2-Dichloroethanesulfonyl chloride

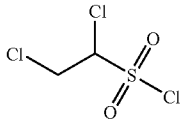

A stirred solution of chlorine in a solution of ethenesulfonyl chloride (32 g, 0.25 mol) in carbon tetrachloride was irradiated at about room temperature (200 W light) for 5 h. The reaction mixture was concentrated under reduced pressure (50 mmHg) and the involatile residue was fractionally distilled to give 1,2-dichloroethanesulfonyl chloride (Goldstein et al. *Zh. Obshch. Khim.*, 28, 1958, 2107) (15,5 g, 31%), b.p. 75° C./0.7 mmHg.

$^1$H-nmr (CDCl$_3$) δ 5.29 (dd, J=8.9 and 3.3 Hz, 1H), 4.40 (dd, J=12.4 and 3.3 Hz, 1H), and 3.97 (dd, J=12.4 and 8.9 Hz, 1H).

1-Chloro-1-ethenesulfonyl chloride

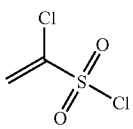

A stirred solution of 1,2-dichloroethanesulfonyl chloride (14.54 g, 73.62 mmol) in dry ether (140 mL) was treated at −60° C. to −50° C. under an atmosphere of nitrogen with 2,6-lutidine (10.30 mL, 88.34 mmol). The stirred reaction mixture was allowed to warm to room temperature, cooled to 0° C. and then treated slowly with dilute aqueous sulfuric acid (1%; 50 mL). The ethereal phase was separated, washed with dilute aqueous sulfuric acid (1%; 2×60 mL) and brine (3×60 mL), dried over magnesium sulfate, and concentrated under reduced pressure (60 mmHg) to give an oil that was purified by distillation to give 1-chloro-1-ethenesulfonyl chloride (7.2 g, 61%), b.p. 26° C./2 mmHg.

$^1$H-nmr (CDCl$_3$) δ 6.70 (d, J=3.8 Hz, 1H) and 6.22 (d, J=3.8 Hz, 1H).

(5R)-3-(3-Fluoro-4-iodophenyl)-5-(4-chloro-1H-1,2,3-triazol-1-ylmethyl)-1,3-oxazolidin-2-one

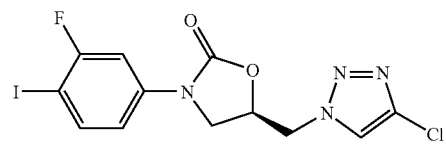

A stirred mixture of (5R)-3-(3-fluoro-4-iodophenyl)-5-azidomethyl-1,3-oxazolidin-2-one (1 g, 28 mmol) and 1-chloro-1-ethenesulfonyl chloride (1 g, 6.2 mmol) was heated in a pressure tube at 80° C. for one hour. The reaction mixture was cooled to room temperature, diluted with chloroform (15 mL), and heated at 80° C. for an additional 4 hours. The reaction mixture was cooled to room temperature and the precipitate was collected by filtration and washed with little dichloromethane to yield the title compound as a colorless amorphous solid (725 mg, 62%).

MS (ESP): 423.3 (MH$^+$) for $C_{12}H_9FIN_4O_2$ $^1$H-NMR (DMSO-d$_6$) δ: 3.89 (dd, 1H); 4.22 (dd, 1H); 4.82 (m, 2H); 5.15 (m, 1H); 7.15 (m, 1H); 7.49 (m, 1H); 7.82 (m, 1H); 8.44 (s, 1H).

(5R)-3-(3-Fluoro-4-(4,4,5,5-tetramethyl-1,3,2-dioxaborolan-2-yl)phenyl)-5-(4-chloro-1H-1,2,3-triazol-1-ylmethyl)-1,3-oxazolidin-2-one

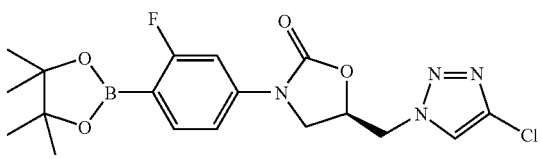

A mixture of (5R)-3-(3-fluoro-4-iodophenyl)-5-(4-chloro-1H-1,2,3-triazol-1-ylmethyl)-1,3-oxazolidin-2-one (725 mg, 1.7 mmol), bis(pinacolato)diboron (1.09 g, 4.3 mmol), and potassium acetate (590 mg, 6 mmol) in dimethylsulfoxide (10 mL) was treated with dichloro[1,1']bis(diphenylphosphino)ferrocene]palladium (II) dichloromethane adduct (90 mg, 0.11 mmol) and allowed to react as described for Example 1. After 45 minutes the reaction mixture was cooled to room temperature, diluted with ethyl acetate and washed with aqueous ammonium chloride solution. The aqueous layer was extracted two times with ethyl acetate and the combined organic layers were washed with water, dried over sodium sulfate, and evaporated to dryness. The involatile residue was purified by chromatography on silica gel [elution with with hexanes:acetone (2:1)] and further purified by precipitation from dichloromethane with hexanes to give the product as a colorless amorphous solid (590 mg 81%) that was sufficiently pure for subsequent reactions.

MS (ESP): 423 (MH+) for $C_{18}H_{21}BFN_4O_4$ $^1$H-NMR (DMSO-d$_6$) δ: 1.28 (s, 12H); 3.92 (dd, 1H); 4.24 (dd, 1H); 4.83 (m, 2H); 5.16 (m, 1H); 7.30 (m, 1H); 7.39 (m, 1H); 7.63 (m, 1H); 8.45 (s, 1H).

EXAMPLE 4

(5R)-3-{3-Fluoro-4-[6-(2-methyl-2H-tetrazol-5-yl)-1-oxidopyridin-3-yl]phenyl}-5-(1H-1,2,3-triazol-1-ylmethyl)-1,3-oxazolidin-2-one

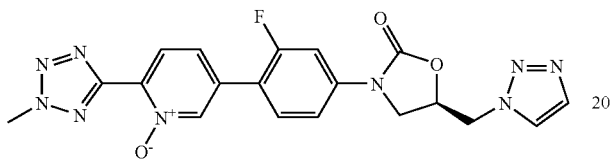

5-Bromo-2-(2-methyl-2H-tetrazol-5-yl)pyridine (175 mg, 0.73 mM) and 3-chloroperbenzoic acid (wet, 70%: 0.50 g, 2.05 mM) were dissolved in 1,2-dichloroethane (5 ml) and heated at 80° C. for 1.5 hours. The mixture was submitted directly to silica gel chromatography, eluting with 25% acetonitrile in dichloromethane. 5-Bromo-2-(2-methyl-2H-tetrazol-5-yl)pyridine 1-oxide was thus obtained as a white solid (165 mg). This material was homogeneous by tlc analysis and was used in the subsequent step without further characterization or purification.

The above sample of pyridine oxide was combined with (5R)-3-[3-fluoro-4-(4,4,5,5-tetramethyl-1,3,2-dioxaborolan-2-yl)phenyl]-5-(1H-1,2,3-triazol-1-ylmethyl)-1,3-oxazolidin-2-one (335 mg, 0.86 mMol, prepared as in Example 1), potassium carbonate (400 mg, 2.9 mMol), and tetrakis (triphenylphosphino)palladium(0) (80 mg, 0.07 mMol) and suspended in THF (10 ml) and water (1 ml). The mixture was heated at 75° C. for 2 hours, then diluted with water. The precipitated solids were collected on a filter, rinsed with water, ether and 1:1 methylene chloride:hexane and dried in vacuo to give the pure product as an off-white solid, 134 mg.

MS (electrospray): 438 (M+1) for $C_{19}H_{16}FN_9O_3$ $^1$H-NMR (300 MHz, DMSO-d$_6$) δ: 3.97 (dd, 1H); 4.30 (t, 1H); 4.49 (s, 3H); 4.86 (d, 2H); 5.19 (m, 1H); 7.43 (dd, 1H); 7.61 (dd, 1H); 7.68 (dd, 1H); 7.77 (t, 2H); 8.06 (d, 1H); 8.18 (s, 1H); 8.68 (s, 1H).

EXAMPLE 5

(5R)-3-[3-Fluoro-4-[6-(2-(2-hydroxyethyl)-2H-1,2,3,4-tetrazol-5-yl)-3-pyridinyl]phenyl]-5-(1H-1,2,3-triazol-1-ylmethyl)oxazolidin-2-one

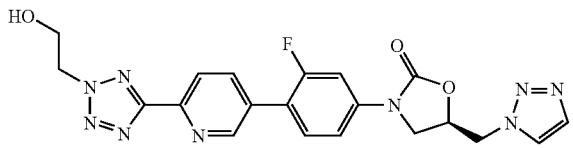

2-[5-(5-Bromopyridin-2-yl)-2H-tetrazol-2-yl]ethanol (167 mg, 0.62 mmol), (5R)-3-[3-fluoro-4-(4,4,5,5-tetramethyl-1,3,2-dioxaborolan-2-yl)phenyl]-[(1H-1,2,3-triazol-1-yl)methyl]oxazolidin-2-one (240 mg, 0.62 mmol) and sodium carbonate (262 mg, 2.47 mmol) were dissolved/suspended in N,N-dimethyl formamide/water (5 ml, 10:1). It was degassed, flushed with nitrogen and tetrakis (triphenylphosphine) palladium (0) (71 mg, 0.061 mmol) was added. It was heated at 70° C. for 3 hours, cooled to room temperature, and the solvent was evaporated. Chromatography on silica gel with dichloromethane/DMF (20:1) gave the required product (198 mg, 71%) as a colorless solid.

MS (ESP): 452.18 (MH+) for $C_{20}H_{18}FN_9O_3$ $^1$H-NMR (DMSO-d$_6$) δ: 3.97 (m, 3H); 4.31 (dd, 1H); 4.70-4.90 (m, 4H); 5.05-5.25 (m, 2H); 7.40-7.80 (m, 4H); 8.15-8.30 (m 6,3H); 8.93 (s, 1H).

The intermediates for Example 5 were prepared as follows:

(5R)-3-[3-fluoro-4-(4,4,5,5-tetramethyl-1,3,2-dioxaborolan-2-yl)-phenyl]-[(1H-1,2,3-triazol-1-yl)methyl]oxazolidin-2-one

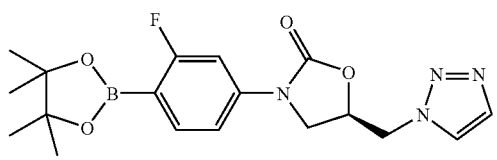

(as in Example 1)

2-[5-(5-Bromopyridin-2-yl)-2H-tetrazol-2-yl]ethanol

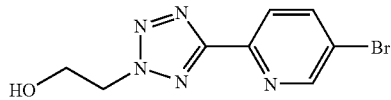

5-Bromo-2-(2H-tetrazol-5-yl)pyridine (WO 0194342 A1) (1.2 g, 5.3 mmol) was dissolved/suspended in 1-propanol (15 ml), a solution of potassium hydroxide (250 mg, 4.5 mmol) in 1-propanol (15 ml) was added and it was heated at 80° C. for 1 hour. 2-Bromoethanol (0.344 ml, 4.8 mmol) was added and it was refluxed for one day. Further potassium hydroxide (270 mg) and 2-bromoethanol (0.35 ml) were added and the mixture was heated for another 4 hours at reflux. Further potassium hydroxide and 2-bromoethanol were added once more and the mixture was refluxed for 14 hours. The reaction mixture was filtered through a 0.45 μM membrane and the filter cake was washed with ethanol and dichloromethane. Chromatography on silica gel with hexanes/ethyl acetate 1:1 to ethyl actetate gave 0.342 g of the title compound (24%), together with 0.225 g of the corresponding 1H-tetrazole regioisomer.

$^1$H-NMR (DMSO-d$_6$) δ: 3.90-4.02 (dt, 2H); 4.78 (t, 2H); 5.09 (t, 1H); 8.10 (m, 1H); 8.27 (dd, 1H); 8.88 (d, 1H).

The assignment of structure for the regioisomers is based upon HMBC NMR experiments with the 1H-tetrazole isomer.

EXAMPLE 6

(5R)-3-[3-Fluoro-4-[6-(1-(propane-1,3-diol-2-yl)-1H-1,2,3,4-tetrazol-5-yl)-3-pyridinyl]phenyl]-5-[(4-fluoromethyl-1H-1,2,3-triazol-1-yl)methyl]oxazolidin-2-

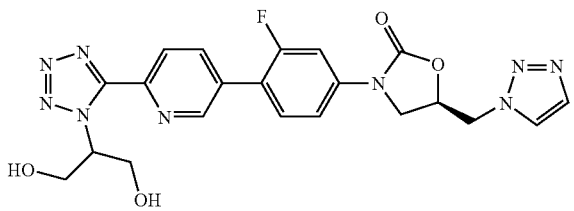

2-[5-(5-Bromopyridin-2-yl)-1H-tetrazol-1-yl]propane-1,3-diol (170 mg, 0.57 mmol), (5R)-3-[3-fluoro-4-(4,4,5,5-tetramethyl-1,3,2-dioxaborolan-2-yl)phenyl]-[(1H-1,2,3-triazol-1-yl)methyl]oxazolidin-2-one (220 mg, 0.57 mmol) and sodium carbonate (240 mg, 2.27 mmol) were dissolved/suspended in N,N-dimethyl formamide/water (5 mL, 10:1). It was degassed, flushed with nitrogen and tetrakis (triphenylphospine) palladium (0) (65 mg, 0.056 mmol) was added. It was heated at 70° C. for 3 hours, cooled to room temperature, and the solvent was evaporated. Chromatography on silica gel with dichloromethane/DMF (20:1) gave 189 mg product (69%) as a colorless solid.

MS (ESP): 482.17 (MH$^+$) for $C_{20}H_{18}FN_9O_3$ $^1$H-NMR (DMSO-d$_6$) δ: 3.85-4.00 (m, 5H); 4.31 (dd, 1H); 4.86 (m, 2H); 5.03(dd, 2H); 5.19 (m, 1H); 5.84 (m, 1H); 7.46 (dd, 1H); 7.62 (dd, 1H); 7.73-7.82 (m, 2H); 8.19 (s, 1H); 8.22-8.35 (m, 2H); 8.98 (s, 1H).

The intermediate for Example 6 was prepared as follows:

2-[5-(5-Bromopyridin-2-yl)-1H-tetrazol-1-yl]propane-1,3-diol

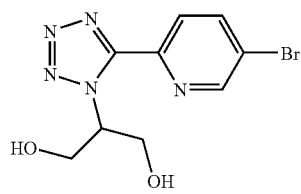

5-Bromo-2-(2H-tetrazol-5-yl)pyridine 0.56 g (2.5 mmol) (WO 0194342 A1, the free acid was generated by dissolving the material obtained following the procedure in WO 0194342 A1 (1 g) in hot water (70 mL, 90° C.); upon addition of HCl (aqueous, 1M, 4 mL) and cooling to room temperature the free acid precipitated, was collected by filtration, washed with water and dried under high vacuum to give 0.56 g free acid), triphenyl phosphine (0.65 g, 2.5 mmol) and 1,3-bis-(tert-butyl-dimethyl-silanyloxy)-propan-2-ol (0.79 g, 2.5 mmol) (D. P. Curran and J.-C. Chao, Synth. Commun. 20, No 22, 1990, 3575-3584) were dissolved/suspended in dry THF (25 mL). It was cooled to 0° C. and diisopropylazodicarboxylate (0.49 mL, 2.5 mmol) was added and the reaction was allowed to warm to room temp. over night. The solvent was evaporated under reduced pressure and the residue subjected to chromatography on silica gel with hexanes/ethyl acetate (30:1) to give the bis-silyl ether of the title compound as a mixture together with the corresponding 2H-tetrazole regioisomer (809 mg). This mixture was dissolved in dry THF (10 mL), cooled to 0° C. and tetrabutylammonium fluoride (1M in THF, 5 mL, 5 mmol) was added drop wise. After one hour solvent was evaporated and the residue subjected to chromatography on silica gel with dichloromethane/acetone (3:1 to 2:1) to give 318 mg of the title compound and 69 mg of the corresponding regioisomeric 2H-substituted tetrazole. The assignment of structure was based on NOE-NMR experiments with the title compound.

$^1$H-NMR (DMSO-d$_6$) δ: 3.80-3.95 (m, 4H); 5.01 (t, 2H); 5.69 (m, 1M); 8.14 (m, 1H); 8.35 (m, 1H); 8.94 (m, 1H).

EXAMPLE 7

(5R)-5-{[4-(Difluoromethyl)-1H-1,2,3-triazol-1-yl]methyl}-3-}3-fluoro-4-[6-(2-methyl-2H-tetrazol-5-yl)pyridin-3-yl]phenyl}-1,3-oxazolidin-2-one

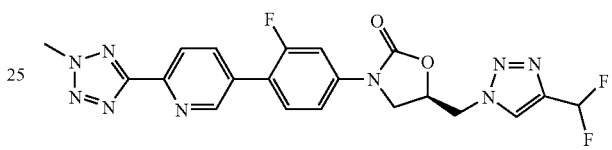

(5R)-5-{[4-(Difluoromethyl)-1H-1,2,3-triazol-1-yl]methyl}-3-[3-fluoro-4-(4,4,5,5-tetramethyl-1,3,2-dioxaborolan-2-yl)phenyl]-1,3-oxazolidin-2-one (0.25 g, 0.586 mmol) were taken together with 5-bromo-[2-(2-methyl-2H-1,2,3,4-tetrazol-5-yl)]pyridine (155 mg, 0.645 mmol) and potassium carbonate (404 mg, 2.93 mmol) and dissolved/suspended in N,N-dimethyl formamide/water (10 mL, 7:1) and reacted under catalysis with Tetrakis (triphenylphospine) palladium (0) (67 mg, 10 mol %) like described for example 1. Chromatography on silica gel with ethyl acetate/hexanes (1:2) gave 200 mg product as a colorless amorphous solid.

MS (ESP): 472.15 (MH$^+$) for $C_{20}H_{16}F_3N_9O_2$ $^1$H-NMR (DMSO-d$_4$) δ: 3.98 (dd, 1H); 4.32 (dd, 1H); 4.47 (s, 3H); 4.88 (d, 2H); 5.22 (m, 1H); 7.05~7.42 (t, br, 1H); 7.46 (m, 1H); 7.60 (m, 1H); 7.75 (m, 1H); 8.15-8.24 (m, 2H); 8.65 (s, 1H); 8.93 (s, 1H).

The intermediates for Example 7 were prepared as follows:

(5R)-5-{[4-(Difluoromethyl)-1H-1,2,3-triazol-1-yl]methyl}-3-[3-fluoro-4-(4,4,5,5-tetramethyl-1,3,2-dioxaborolan-2-yl)phenyl]-1,3-oxazolidin-2-one

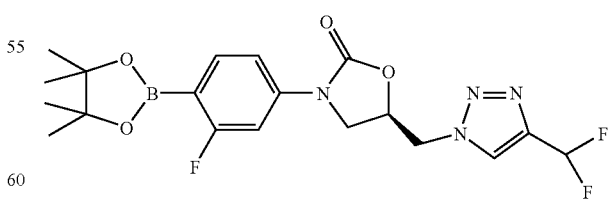

(5R)-5-{[4-(Difluoromethyl)-1H-1,2,3-triazol-1-yl]methyl}-3-(3-fluoro-4-iodophenyl)-1,3-oxazolidin-2-one (2.56 g, 5.84 mmol), bis(pinacolato)diboron (3.71 g, 14.6 mmol), potassium acetate (2.0 g, 20.44 mmol), and 1,1'-[bis(diphenylphosphino)ferrocene]dichloropalladium(II)

dichoromethane complex (0.427 g, 0.584 mmol) were suspended in DMSO (10 ml). The mixture was heated at 80° C. for 90 minutes to give a clear black solution. After cooling down to room temperature, ethyl acetate (150 ml) was then added and the mixture was filtered through celite, washed with saturated brine (2×100 ml), dried over sodium sulfate and concentrated to dryness. The dark residue was dissolved in dichloromethane (20 ml), followed by slow addition of hexanes (100 ml), the resulting precipitate was filtered and washed with 5% dichloromethane in hexanes and collected as the desirred product (1.73 g) which was used directly as an intermediate without further purification.

$^1$H-NMR (DMSO-$d_6$) δ: 1.12 (s, 12H); 3.88 (dd, 1H); 4.23 (dd, 1H); 4.84 (m, 2H); 5.14 (m, 1H); 6.80~7.20 (t, br, 1H); 7.14 (m, 1H); 7.28 (m, 1H); 7.51 (m,1H); 8.45 (s, 1H).

(5R)-5-{[4-(Difluoromethyl)-1H-1,2,3-triazol-1-yl]methyl}-3-(3-fluoro-4-iodophenyl)-1,3-oxazolidin-2-one

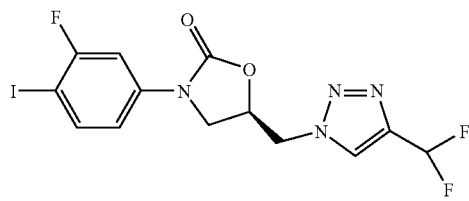

1-{[(5R)-3-(3-Fluoro-4-iodophenyl)-2-oxo-1,3-oxazolidin-5-yl]methyl}-1H-1,2,3-triazole-4-carbaldehyde (3.6 g, 8.65 mmol) and [Bis(2-methoxyethyl)amino]-sulfur trifluoride (2.3 g, 10.38 mmol) were mixed in dry dichloromethane (20 ml), followed by the addition of ethanol (20 ul), the reaction mixture was then refluxed for 14 hours, cooled down to room temperature, washed with saturated aqueous sodium bicarbonate solution and dried over anhydrous magnesium sulphate. The concentrated crude sample was then purified by column chromatography eluted with hexanes/ethylacetate (1.5:1) to give the title compound (2.58 g).

MS (ESP): 439.02 (MH$^+$) for $C_{13}H_{10}F_3IN_4O_2$ $^1$H-NMR (DMSO-$d_6$) δ: 4.02 (dd, 1H); 4.40 (dd, 1H); 5.03 (d, 2H); 5.30 (m, 1H); 7.15~7.53(t, br, 1H); 7.28 (dd, 1H); 7.6 (dd,1H); 7.95 (t, 1H); 8.70 (s, 1H).

1-{[(5R)-3-(3-Fluoro-4-iodophenyl)-2-oxo-1,3-oxazolidin-5-yl]methyl}-1H-1,2,3-triazole-4-carbaldehyde

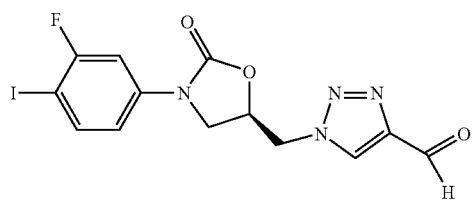

(5R)-3-(3-Fluoro-4-iodophenyl)-5-[(4-hydroxymethyl-1H-1,2,3-triazol-1-yl)methyl]oxazolidin-2-one (5.7 g, 13.6 mmol) and manganese oxide (3.56 g, 40.9 mmol) were mixed and heated up to 100° C. in dry 1,4-dioxane for 48 hours, then the mixture was cooled down to 70° C. and filtered through celite. The filtrate was concentrated and dissolved in 5% methanol in dichloromethane, hexaneses was added and the formed precipitates were filtered and collected as the title compound (3.6 g).

MS (ESP): 416.91 (MH$^+$) for $C_{13}H_{10}FIN_4O_3$ $^1$H-NMR (DMSO-$d_6$) δ: 3.87 (m, 1H); 4.18 (dd, 1H); 4.85 (d, 2H); 5.15 (m, 1H); 7.12 (d, 1H); 7.42 (d, 1H); 7.8 (dd,1H); 8.88 (s, 1H); 10.01 (s, 1H).

(5R)-3-(3-Fluoro-4-iodophenyl)-5-[(4-hydroxymethyl-1H-1,2,3-triazol-1-yl)methyl]oxazolidin-2-one

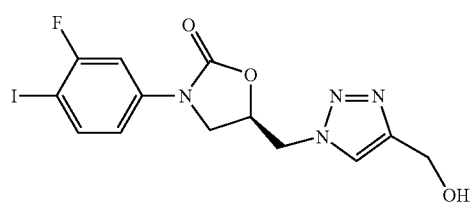

(5R)-3-(3-Fluoro-4-iodophenyl)-5-(azidomethyl)oxazolidin-2-one (10 g, 28 mmol) was dissolved in acetonitrile (80 mL). Propargyl alcohol (3.2 mL, 56 mmol) was added and then CuI (526 mg, 2.8 mmol) and it was stirred overnight. The solidified reaction mixture was extracted with ethyl acetate/acetonitrile, washed with water and dried over magnesium sulfate. Evaporation of solvent under vacuum gave 12.3 g crude product (quantitative).

MS (ESP): 419.13 (MH$^+$) for $C_{13}H_{12}FIN_4O_3$ $^1$H-NMR (DMSO-$d_6$) δ: 3.88 (dd, 1H); 4.23 (dd, 1H); 4.51 (d, 2H); 4.80 (m, 2H); 5.14 (m, 1H); 5.22 (dd, 1H); 7.16 (m, 1H); 7.51 (m, 1H); 7.83 (m, 1H); 8.01 (d, 1H).

EXAMPLE 8

(5R)-3-{3-Fluoro-4-[2-methyl-6-(4-methyl-1H-1,2,3-triazol-1-yl)pyrid-3-yl]phenyl}-5-(1H-1,2,3-triazol-1-ylmethyl)-1,3-oxazolidin-2-one

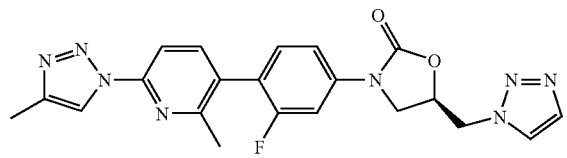

3-Bromo-2-methyl-6-(4-methyl-1H-1,2,3-triazol-1-yl)pyridine (196 mg, 0.773 mmol), (5R)-3-[3-fluoro-4-(4,4,5,5-tetramethyl-1,3,2-dioxaborolan-2-yl)phenyl]-5-(1H-1,2,3-triazol-1-ylmethyl)-1,3-oxazolidin-2-one (300 mg, 0.773 mmol), potassium carbonate (320 mg, 2.31 mmol), and tetrakis(triphenylphosphino) palladium(0) (89 mg, 0.077 mmol) were combined and suspended in DMF (3 ml) and water (0.3 ml). The mixture was heated at 80° C. for 2 hours, then diluted with water to 7 ml. The solids were collected, rinsed with water and resuspended in warm DMSO (3 ml). The suspension was diluted with dichloromethane (5 ml) and ether (4 ml). The solid was collected, rinsed with ether and methanol, and dried in vacuo to give the pure product as a white solid, 110 mg.

MS (APCI): 435 (M+1) for $C_{21}H_{19}N_8O_2F$

NMR (DMSO-$d_6$) δ: 2.36 (s, 3H); 2.41(s, 3H); 3.95 (dd, 1H); 4.31 (t, 1H); 4.88 (d, 2H); 5.15-5.24 (m, 1H); 7.44 (dd, 1H); 7.50 (t,1H); 7.62 (dd, 1H); 7.79 (d, 1H); 7.95 (q, 2H); 8.20 (d, 1H); 8.61 (d, 1H).

The intermediates for the above compound was made as follows:

3-Bromo-2-methyl-6-(4-methyl-1H-1,2,3-triazol-1-yl)pyridine

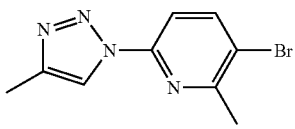

To a solution of 6-amino-3-bromo-2-methylpyridine (1.0 g, 5.3 mmol) in methanol (20 ml) was added diisopropylethylamine (2.8 ml, 16.0 mmol) at room temperature. The solution was stirred for 10 min., [(1E)-2,2-dichloro-1-methylethylidene]hydrazide-4-methyl-benzenesulfonic acid (2.0 g, 6.95 mmol) was added at 4° C. and the reaction mixture was stirred over weekend at room temperature. The solvent was evaporated in vacuo and the residue purified by chromatography on silica gel eluting with 25% ethyl acetate in hexane to give the title compound (758 mg).

MS (APCI): 254 (M+1) for $C_9H_9BrN_4$ $^1$H-NMR(DMSO-$d_6$) δ: 2.34 (s, 3H); 2.64 (s, 3H); 7.83 (d, 2H); 8.26 (d, 1H); 8.56 (s,1H).

(5R)-3-[3-Fluoro-4-(4,4,5,5-tetramethyl-1,3,2-dioxaborolan-2-yl)phenyl]-5-(1H-1,2,3-triazol-1-ylmethyl)-1,3-oxazolidin-2-one see Example 1

The invention claimed is:

1. A compound of the formula (I), or a pharmaceutically-acceptable salt, or an in-vivo-hydrolysable ester thereof,

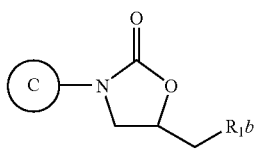

(I)

wherein C is selected from D and E,

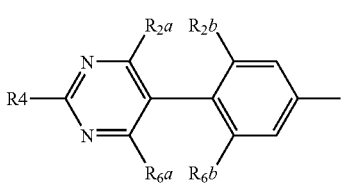

D

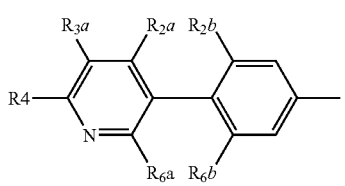

E wherein in D and E the phenyl ring is attached to the oxazolidinone in (I);

$R_1b$ is HET1 or HET2, wherein i) HET1 is an N-linked 5-membered, fully or partially unsaturated heterocyclic ring, containing either (i) 1 to 3 further nitrogen heteroatoms or (ii) a further heteroatom selected from O and S together with an optional further nitrogen heteroatom; which ring is optionally substituted on a C atom, other than a C atom adjacent to the linking N atom, by an oxo or thioxo group; and/or which ring is optionally substituted on any available C atom, other than a C atom adjacent to the linking N atom, by a substituent selected from RT as hereinafter defined and/or on an available nitrogen atom, other than a N atom adjacent to the linking N atom, (provided that the ring is not thereby quaternised) by (1-4C)alkyl;

ii) HET2 is an N-linked 6-membered di-hydro-heteroaryl ring containing up to three nitrogen heteroatoms in total (including the linking heteroatom), which ring is substituted on a suitable C atom, other than a C atom adjacent to the linking N atom, by oxo or thioxo and/or which ring is optionally substituted on any available C atom, other than a C atom adjacent to the linking N atom, by one or two substituents independently selected from RT as hereinafter defined and/or on an available nitrogen atom, other than a N atom adjacent to the linking N atom, (provided that the ring is not thereby quaternised) by (1-4C)alkyl;

RT is selected from a substituent from the group:

(RTa1) hydrogen, halogen, (1-4C)alkoxy, (2-4C)alkenyloxy, (2-4C)alkenyl, (2-4C)alkynyl, (3-6C)cycloalkyl, (3-6C)cycloalkenyl, (1-4C)alkylthio, amino, azido, cyano and nitro; or (RTa2) (1-4C)alkylamino, di-(1-4C)alkylamino, and (2-4C)alkenylamino;

or RT is selected from the group (RTb1) (1-4C)alkyl group which is optionally substituted by one substituent selected from hydroxy, (1-4C)alkoxy, (1-4C)alkylthio, cyano and azido; or (RTb2) (1-4C)alkyl group which is optionally substituted by one substituent selected from (2-4C)alkenyloxy, (3-6C)cycloalkyl, and (3-6C)cycloalkenyl;

or RT is selected from the group (RTc) a fully saturated 4-membered monocyclic ring containing 1 or 2 heteroatoms independently selected from O, N and S (optionally oxidised), and linked via a ring nitrogen or carbon atom;

and wherein at each occurrence of an RT substituent containing an alkyl, alkenyl, alkynyl, cycloalkyl or cycloalkenyl moiety in (RTa1) or (RTa2), (RTb1) or (RTb2), or (RTc) each such moiety is optionally substituted on an available carbon atom with one, two, three or more substituents independently selected from F, Cl, Br, OH and CN;

$R_2a$ and $R_6a$ are independently selected from H, $CF_3$, OMe, SMe, Me and Et;

$R_2b$ and $R_6b$ are independently selected from H, F, Cl, $CF_3$, OMe, SMe, Me and Et;

$R_3a$ is selected from H, (1-4C)alkyl, cyano, Br, F, Cl, OH, (1-4C)alkoxy, —S(O)$_n$(1-4C)alkyl (wherein n=0, 1, or 2), amino, (1-4C)alkylcarbonylamino, nitro, —CHO, —CO(1-4C)alkyl, —CONH$_2$ and —CONH(1-4C)alkyl;

R4 is selected from $R_4a$ and $R_4b$, wherein $R_4a$ is selected from azido, —NR$_7$R$_8$, OR$_{10}$, (1-4C)alkyl, (1-4C)alkoxy, (3-6C)cycloalkyl, —(CH$_2$)$_k$—R$_9$, AR1, AR2, (1-4C)alkanoyl, —CS(1-4C)alkyl, —C(=W)NRvRw [wherein W is O or S, Rv and Rw are independently H, or (1-4C)alkyl], —(C=O)$_l$—R$_6$, —COO(1-4C)alkyl, —C=OAR1, —C=OAR2, —COOAR1, S(O)n(1-4C)alkyl (wherein n=1 or 2), —S(O)pAR1, —S(O)pAR2 and —C(=S)O(1-4C)alkyl; wherein any (1-4C)alkyl chain may be optionally substituted by (1-4C)alkyl, cyano, hydroxy or halo; p=0, 1 or 2;

$R_4b$ is selected from HET-3;

$R_6$ is selected from hydrogen, (1-4C)alkoxy, amino, (1-4C)alkylamino and hydroxy(1-4C)alkylamino;

k is 1 or 2;

l is 1 or 2;

$R_7$ and $R_8$ are independently selected from H and (1-4C)alkyl, or wherein $R_7$ and $R_8$ taken together with the nitrogen to which they are attached can form a 5-7 membered ring optionally with an additional heteroatom selected from N, O, S(O)n (wherein n=1 or 2) in place of 1 carbon atom of the so formed ring; wherein the ring may be optionally substituted by one or two groups independently selected from (1-4C)alkyl, (3-6C)cycloalkyl, (1-4C)alkanoyl, —COO(1-4C)alkyl, —S(O)n (1-4C)alkyl (wherein n=1 or 2), AR1, AR2, —C=OAR1, —C=OAR2, —COOAR1, —CS(1-4C)alkyl, —C(=S)O(1-4C)alkyl, —C(=W)NRvRw [wherein W is O or S, Rv and Rw are independently H, or (1-4C)alkyl], —S(O)pAR1 and —S(O)pAR2; wherein any (1-4C)alkyl, (3-6C)cycloalkyl or (1-4C)alkanoyl group may be optionally substituted (except on a carbon atom adjacent to a heteroatom) by one or two substituents selected from (1-4C)alkyl, cyano, hydroxy, halo, amino, (1-4C)alkylamino and di(1-4C)alkylamino; p=0, 1 or 2;

$R_9$ is independently selected from $R_9a$ to $R_9d$ below:

$R_9a$: AR1, AR2, AR2a, AR2b, AR3, AR3a, AR3b, AR4, AR4a, CY1, CY2;

$R_9b$: cyano, carboxy, (1-4C)alkoxycarbonyl, —C(=W)NRvRw [wherein W is O or S, Rv and Rw are independently H, or (1-4C)alkyl and wherein Rv and Rw taken together with the amide or thioamide nitrogen to which they are attached can form a 5-7 membered ring optionally with an additional heteroatom selected from N, O, S(O)n in place of 1 carbon atom of the so formed ring; wherein when said ring is a piperazine ring, the ring may be optionally substituted on the additional nitrogen by a group selected from (1-4C)alkyl, (3-6C)cycloalkyl, (1-4C)alkanoyl, —COO(1-4C)alkyl, —S(O)n (1-4C)alkyl (wherein n=1 or 2), —COOAR1, —CS(1-4C)alkyl and —C(=S)O(1-4C)alkyl; wherein any (1-4)alkyl, (3-6C)cycloalkyl or (1-4C)alkanoyl group may itself optionally be substituted by cyano, hydroxy or halo], ethenyl, 2-(1-4C)alkylethenyl, 2-cyanoethenyl, 2-cyano-2-((1-4C)alkyl)ethenyl, 2-nitroethenyl, 2-nitro-2-((1-4C)alkyl)ethenyl, 2-((1-4C)alkylaminocarbonyl)ethenyl, 2-((1-4C)alkoxycarbonyl)ethenyl, 2-(1-4C)alkoxycarbonyl)ethenyl, 2-(AR1)ethenyl, 2-(AR2)ethenyl, 2-(AR2a)ethenyl;

$R_9c$: (1-6C)alkyl {optionally substituted by one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkylcarbonyl, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], and amino; and/or optionally substituted by one group selected from carboxy, phosphonate [phosphono, —P(O)(OH)$_2$, and mono- and di-(1-4C)alkoxy derivatives thereof], phosphinate [—P(OH)$_2$ and mono- and di-(1-4C)alkoxy derivatives thereof], cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino-, (1-4C)alkoxycarbonylamino-, N-(1-4C)alkyl-N-(1-6C)alkanoylamino-, —C(=W)NRvRw [wherein W is O or S, Rv and Rw are as hereinbefore defined], (=NORv) wherein Rv is as hereinbefore defined, (1-4C)alkylS(O)$_p$NH, (1-4C)alkylS(O)$_p$-((1-4C)alkyl)N—, fluoro(1-4C)alkylS(O)$_p$NH—, fluoro(1-4C)alkylS(O)$_p$((1-4C)alkyl)N—, (1-4C)alkylS(O)$_q$—, CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups}; wherein any (1-4C)alkyl present in any substituent on R9c may itself be substituted by one or two groups independently selected from cyano, hydroxy, halo, amino, (1-4C)alkylamino and di(1-4C)alkylamino, provided that such a substituent is not on a carbon adjacent to a heteroatom atom if present;

$R_9d$: $R_{14}$C(O)O(1-6C)alkyl- wherein $R_{14}$ is AR1, AR2, (1-4C)alkylamino, benzyloxy-(1-4C)alkyl or (1-10C)alkyl {optionally substituted as defined for (R$_9$c)};

$R_{10}$ is selected from hydrogen, R$_9$c (as hereinbefore defined), (1-4C)acyl and (1-4C)alkylsulfonyl;

HET-3 is selected from:

a) a 5-membered heterocyclic ring containing at least one nitrogen and/or oxygen in which any carbon atom is a C=O, C=N, or C=S group, wherein said ring is of the formula HET3-A to HET3-E below:

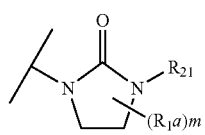

HET3-A

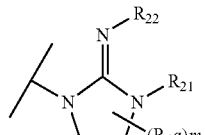

HET3-B

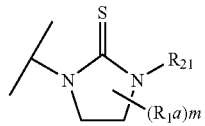

HET3-C

-continued
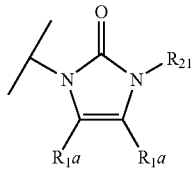
HET3-D
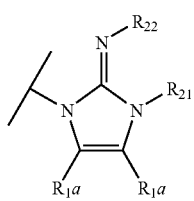
HET3-E
b) a carbon-linked 5- or 6-membered heteroaromatic ring containing 1, 2, 3, or 4 heteroatoms independently selected from N, O and S selected from HET3-F to HET3-Y below:
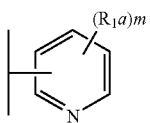
HET3-F
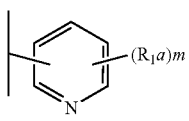
HET3-G
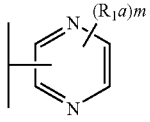
HET3-H
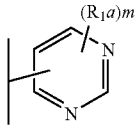
HET3-I
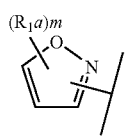
HET3-J
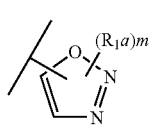
HET3-K
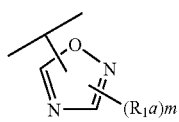
HET3-L
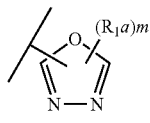
HET3-M
-continued
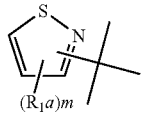
HET3-N
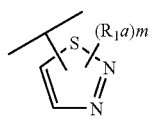
HET3-O
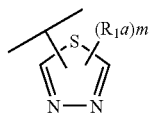
HET3-P
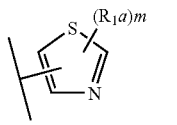
HET3-Q
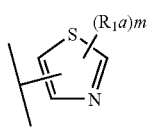
HET3-R
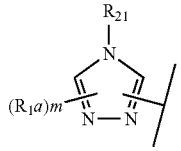
HET3-S
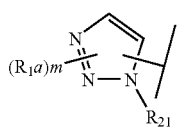
HET3-T
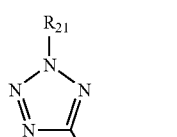
HET3-U
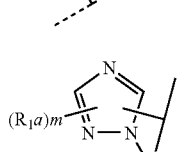
HET3-V
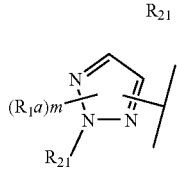
HET3-W
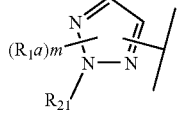
HET3-X -continued

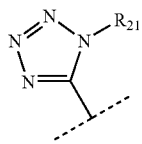

HET3-Y c) a nitrogen-linked 5- or 6-membered heteroaromatic ring containing 1, 2, 3, or 4 heteroatoms independently selected from N, O and S selected from HET3-Z to HET3-AH below:

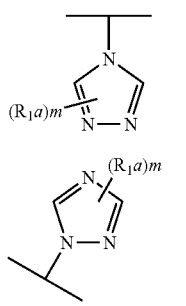

HET3-Z

HET3-AA

HET3-AB

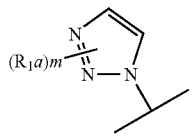

HET3-AC

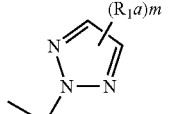

HET3-AD

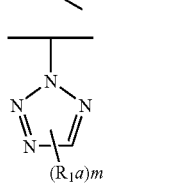

HET3-AE

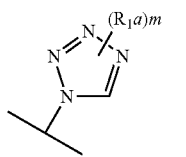

HET3-AF

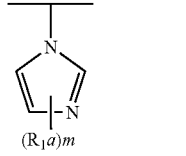

HET3-AG

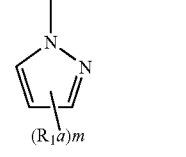

-continued

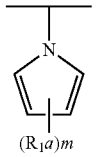

HET3-AH wherein in HET-3, $R_1a$ is a substituent on carbon;

$R_1a$ is independently selected from $R_1a1$ to $R_1a5$ below:

$R_1a1$: AR1, AR2, AR2a, AR2b, AR3, AR3a, AR3b, AR4, AR4a, CY1, CY2;

$R_1a2$: cyano, carboxy, (1-4C)alkoxycarbonyl, —C(=W)NRvRw [wherein W is O or S, Rv and Rw are independently H, or (1-4C)alkyl and wherein Rv and Rw taken together with the amide or thioamide nitrogen to which they are attached can form a 5-7 membered ring optionally with an additional heteroatom selected from N, O, S(O)n in place of 1 carbon atom of the so formed ring; wherein when said ring is a piperazine ring, the ring may be optionally substituted on the additional nitrogen by a group selected from (1-4C)alkyl, (3-6C)cycloalkyl, (1-4C)alkanoyl, —COO(1-4C)alkyl, —S(O)n(1-4C)alkyl (wherein n=1 or 2), —COOAR1, —CS(1-4C)alkyl) and —C(=S)O(1-4C)alkyl; wherein any (1-4C)alkyl, (1-4C)acyl and (1-4C)cycloalkyl substituent may itself be substituted by cyano, hydroxy or halo, provided that, such a substituent is not on a carbon adjacent to a nitrogen atom of the piperazine ring], ethenyl, 2-(1-4C)alkylethenyl, 2-cyanoethenyl, 2-cyano-2-((1-4C)alkyl)ethenyl, 2-nitroethenyl, 2-nitro-2-((1-4C)alkyl)ethenyl, 2-((1-4C)alkylaminocarbonyl)ethenyl, 2-((1-4C)alkoxycarbonyl)ethenyl, 2-(AR1)ethenyl, 2-(AR2)ethenyl, 2-(AR2a)ethenyl;

$R_1a3$: (1-10C)alkyl

{optionally substituted by one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkylcarbonyl, phosphoryl [—O—P(O)(OH)$_2$, and mono- and di-(1-4C)alkoxy derivatives thereof], phosphiryl [—O—P(OH)$_2$ and mono- and di-(1-4C)alkoxy derivatives thereof], and amino; and/or optionally substituted by one group selected from carboxy, phosphonate [phosphono, —P(O)(OH)$_2$, and mono- and di-(1-4C)alkoxy derivatives thereof], phosphinate [—P(OH)$_2$ and mono- and di-(1-4C)alkoxy derivatives thereof], cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino-, (1-4C)alkoxycarbonylamino-, N-(1-4C)alkyl-N-(1-6C)alkanoylamino-, —C(=W)NRvRw [wherein W is O or S, Rv and Rw are independently H, or (1-4C)alkyl and wherein Rv and Rw taken together with the amide or thioamide nitrogen to which they are attached can form a 5-7 membered ring optionally with an additional heteroatom selected from N, O, S(O)n in place of 1 carbon atom of the so formed ring; wherein when said ring is a piperazine ring, the ring may be optionally substituted on the additional nitrogen by a group selected from (1-4C)alkyl, (3-6C)cycloalkyl, (1-4C)alkanoyl, —COO(1-4C)alkyl, —S(O)n(1-4C)alkyl (wherein n=1 or 2), —COOAR1, —CS(1-4C)alkyl and —C(=S)O(1-4C)alkyl], (=NORv) wherein Rv is as hereinbefore defined, (1-4C)alkylS(O)$_p$NH—, (1-4C)alkylS(O)$_p$-((1-4C)alkyl)N—, fluoro(1-4C)alkylS(O)$_p$NH—, fluoro(1-4C)alkylS(O)$_p$((1-4C)alkyl)N—, (1-4C)alkylS(O)$_q$—, CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups}; wherein any (1-4C)alkyl, (1-4C)alkanoyl and (3-6C)cycloalkyl present in any substituent on R$_1$a3 may itself be substituted by one or two groups independently selected from cyano, hydroxy, halo, amino, (1-4C)alkylamino and di(1-4C)alkylamino, provided that such a substituent is not on a carbon adjacent to a heteroatom atom if present;

R$_1$a4: R$_{14}$C(O)O(1-6C)alkyl- wherein R$_{14}$ is AR1, AR2, AR2a, AR2b, (1-4C)alkylamino, benzyloxy-(1-4C)alkyl or (1-10C)alkyl {optionally substituted as defined for (R$_1$a3)};

R$_1$a5: F, Cl, hydroxy, mercapto, (1-4C)alkylS(O)p- (p=0, 1 or 2), —NR$_7$R$_8$ (wherein R$_7$ and R$_8$ are as hereinbefore defined) or —OR$_{10}$ (where R$_{10}$ is as hereinbefore defined);

m is 0, 1 or 2;

R$_{21}$ is selected from hydrogen, methyl [optionally substituted with cyano, trifluoromethyl, —C=WNRvRw (where W, Rv and Rw are as hereinbefore defined for R$_1$a3), (1-4C)alkoxycarbonyl, (1-4C)alkoxy-(1-4C)alkoxycarbonyl, (1-4C)alkoxy-(1-4C)alkoxy-(1-4C)alkoxycarbonyl, CY1, CY2, AR1, AR2, AR2a, AR2b (not linked through nitrogen) or AR3], (2-10C)alkyl [optionally substituted other than on a carbon attached to the HET-3 ring nitrogen with one or two groups independently selected from the optional subsituents defined for R$_1$a3] and R$_{14}$C(O)O(2-6C)alkyl- wherein R$_{14}$ is as defined hereinbefore for R$_1$a4 and wherein R$_{14}$C(O)O group is attached to a carbon other than the carbon attached to the HET-3 ring nitrogen;

R$_{22}$ is cyano, —COR$_{12}$, —COOR$_{12}$, —CONHR$_{12}$, —CON(R$_{12}$)(R$_{13}$), —SO$_2$R$_{12}$ (provided that R$_{12}$ is not hydrogen), —SO$_2$NHR$_{12}$, —SO$_2$N(R$_{12}$)(R$_{13}$) or NO$_2$, wherein R$_{12}$ and R$_{13}$ are as defined hereinbelow;

R$_{12}$ and R$_{13}$ are independently selected from hydrogen, phenyl (optionally substituted with one or more substituents selected from halogen, (1-4C)alkyl and (1-4C)alkyl substituted with one, two, three or more halogen atoms) and (1-4C)alkyl (optionally substituted with one, two, three or more halogen atoms), or for any N(R$_{12}$)(R$_{13}$) group, R$_{12}$ and R$_{13}$ may be taken together with the nitrogen to which they are attached to form a 5-7 membered ring optionally with an additional heteroatom selected from N, O, S(O)n in place of 1 carbon atom of the so formed ring; wherein the ring may be optionally substituted by one or two groups independently selected from (1-4C)alkyl (optionally substituted on a carbon not adjacent to the nitrogen by cyano, hydroxy or halo), (1-4C)cycloalkyl, (1-4C)alkanoyl, —COO(1-4C)alkano, —S(O)n(1-4C)alkyl (wherein n=1 or 2), AR1, AR2, —C=OAR1, —C=OAR2, —COOAR1, —CS(1-4C)alkyl, —C(=S)O(1-4C)alkyl, —C(=W)NRvRw [wherein W is O or S, Rv and Rw are independently H, or (1-4C)alkyl], —S(O)pAR1 and —S(O)pAR2; wherein any (1-4C)alkyl chain may be optionally substituted by (1-4C)alkyl, cyano, hydroxy or halo; p=0, 1 or 2;

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some but not the full, degree of unsaturation), linked via a ring carbon atom or linked via nitrogen atom if ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e. with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full degree of unsaturation), linked via a ring carbon atom, or linked via a ring nitrogen atom if the ring is not thereby quaternised, in any of the rings comprising the tricyclic system;

CY1 is an optionally substituted cyclopentenyl or cyclohexenyl ring;

CY2 is an optionally substituted cyclopentenyl or cyclohexenyl ring;

wherein; optional substituents on AR1, AR2, AR2a, AR2b, AR3, AR3a, AR3b, AR4, AR4a, CY1 and CY2 are (on an available carbon atom) up to three substituents independently selected from (1-4C)alkyl {optionally substituted by substituents selected independently from hydroxy, trifluoromethyl, (1-4C)alkylS(O)$_q$— (q is 0, 1 or 2), (1-4C)alkoxy, (1-4C)alkoxycarbonyl, cyano, nitro, (1-4C)alkanoylamino, —CONRvRw or —NRvRw}, trifluoromethyl, hydroxy, halo, nitro, cyano, thiol, (1-4C)alkoxy, (1-4C)alkanoyloxy, dimethylaminomethyleneaminocarbonyl, di(N-(1-4C)alkyl)aminomethylimino, carboxy, (1-4C)alkoxycarbonyl, (1-4C)alkanoyl, (1-4C)alkylSO$_2$amino, (2-4C)alkenyl {optionally substituted by carboxy or (1-4C)alkoxycarbonyl}, (2-4C)alkynyl, (1-4C)alkanoylamino, oxo (=O), thioxo (=S), (1-4C)alkanoylamino {the (1-4C)alkanoyl group being optionally substituted by hydroxy}, (1-4C)alkyl S(O)$_q$— (q is 0, 1 or 2) {the (1-4C)alkyl group being optionally substituted by one or more groups independently selected from cyano, hydroxy and (1-4C)alkoxy}, —CONRvRw or —NRvRw [wherein Rv is hydrogen or (1-4C)alkyl; Rw is hydrogen or (1-4C)alkyl];

and further optional substituents on AR1, AR2, AR2a, AR2b, AR3, AR3a, AR3b, AR4, AR4a, CY1 and CY2 (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1-4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1-4C)alkyl, (1-4C)alkoxyimino(1-4C)alkyl, halo-(1-4C)alkyl, (1-4C)alkanesulfonamido, —SO$_2$NRvRw [wherein Rv is hydrogen or (1-4C)alkyl; Rw is hydrogen or (1-4C)alkyl]; and optional substituents on AR2, AR2a, AR2b, AR3, AR3a, AR3b, AR4 and AR4a are (on an available nitrogen atom, where such substitution does not result in quaternization) (1-4C)alkyl, (1-4C)alkanoyl {wherein the (1-4C)alkyl and (1-4C)alkanoyl groups are optionally substituted by (preferably one) substituents independently selected from cyano, hydroxy, nitro, trifluoromethyl, (1-4C)alkyl S(O)$_q$— (q is 0, 1 or 2), (1-4C)alkoxy, (1-4C)alkoxycarbonyl, (1-4C)alkanoylamino, —CONRvRw or —NRvRw [wherein Rv is hydrogen or (1-4C)alkyl; Rw is hydrogen or (1-4C)alkyl]}, (2-4C)alkenyl, (2-4C)alkynyl, (1-4C)alkoxycarbonyl or oxo (to form an N-oxide).

2. A compound of the formula (I) as claimed in claim 1 or a pharmaceutically acceptable salt or an in-vivo-hydrolysable ester thereof, wherein R$_1$b is HET1 and wherein HET1 is selected from the structures (Za) to (Zf),

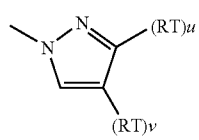
(Za)

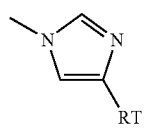
(Zb)

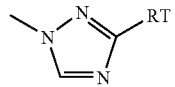
(Zc)

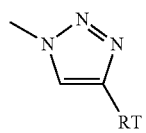
(Zd)

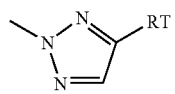
(Ze)

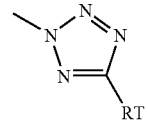
(Zf)

wherein u and v are independently 0 or 1 and RT selected from:
(a) hydrogen;
(b) halogen;
(c) cyano;
(d) (1-4C)alkyl;
(e) monosubstituted (1-4C)alkyl;
(f) disubstituted (1-4C)alkyl, and
(g) trisubstituted (1-4C)alkyl.

3. A compound of claim 2 or a pharmaceutically acceptable salt or an in-vivo-hydrolysable ester thereof, wherein R$_4$ is R$_4$b.

4. A compound of claim 3 or a pharmaceutically acceptable salt or an in-vivo-hydrolysable ester thereof, wherein HET-3 is selected from HET-3-T, HET3-V, HET3-Y and HET-3-W.

5. A compound of the claim 4 or a pharmaceutically acceptable salt or an in-vivo-hydrolysable ester thereof, wherein HET-3 is selected from HET3-V and HET3-Y.

6. A compound of claim 5 or a pharmaceutically acceptable salt or an in-vivo-hydrolysable ester thereof, wherein R$_1$a is R$_1$a3.

7. A compound of claim 6 or a pharmaceutically acceptable salt or an in-vivo-hydrolysable ester thereof wherein group C is group D.

8. A compound of claim 6 or a pharmaceutically acceptable salt or an in-vivo-hydrolysable ester thereof, wherein group C is group E.

9. A method for treating a bacterial infection comprising administering to a warm blooded animal in need thereof an effective amount of a compound of claim 1 or a pharmaceutically-acceptable salt, or in-vivo hydrolysable ester thereof, wherein the infection is caused by bacteria selected from the group consisting of methacillin resistant staphylococcus, methacillin resistant coagulase negative staphylococci, streptococcus pneumoniae, Enterococcus faecium, Haemophillus influenzae, Moraxella catarrhalis and Linezolid resistant streptococcus pneumoniae.

10. A pharmaceutical composition which comprises a compound of claim 1 or a pharmaceutically acceptable salt or an in-vivo-hydrolysable ester thereof and a pharmaceutically-acceptable diluent or carrier.

11. A process for the preparation of a compound of formula (I) as claimed in claim 1 or pharmaceutically acceptable salts or in-vivo hydrolysable esters thereof, which process comprises one of processes (a) to (i);
   a) converting one compound of formula (I) into another compound of formula (I);
   b) reacting a molecule of a compound of formula (IIa) [wherein X is a leaving group useful in palladium coupling and A is either N or C—R$_3$a] with a molecule of a compound of formula (IIb) (wherein X' is a leaving group useful in palladium coupling) wherein X and X' are such that an aryl-aryl, heteroaryl-aryl, or heteroaryl-heteroaryl bond replaces the aryl-X (or heteroaryl-X) and aryl-X' (or heteroaryl-X') bonds; and X and X' are chosen to be different to lead to the desired cross-coupling products of formula (I);

(IIa)

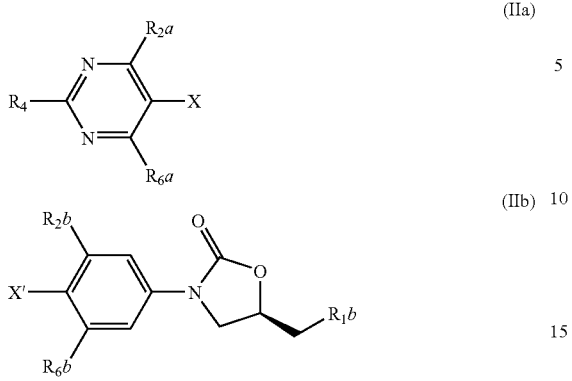

(IIb)

c) reacting a heterobiaryl derivative (III) carbamate with an appropriately substituted oxirane

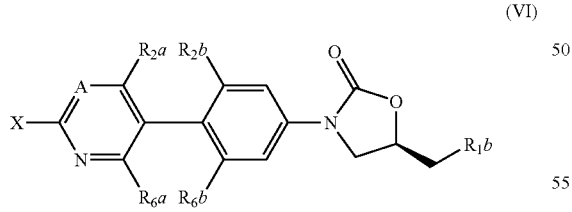

to form an oxazolidinone ring;

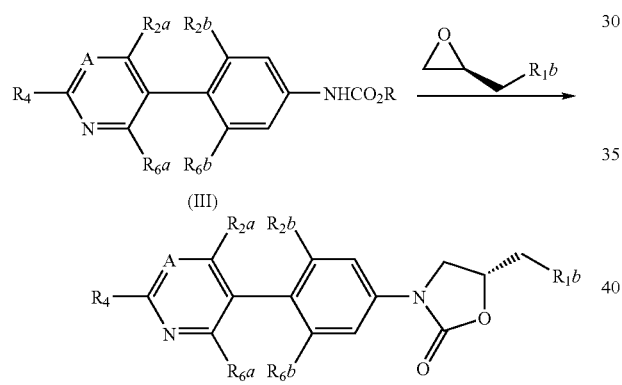

(d) reacting a compound of formula (VI):

(VI)

where X is a replaceable substituent with a compound of the formula (VII):

T-X'  (VII)

wherein T-X' is HET1 or HET2 as herein above defined and X' is a replaceable C-linked substituent; wherein the substituents X and X' are chosen to be complementary pairs of substituents suitable as complementary substrates for coupling reactions catalysed by transition metals;

(d(i)) by reaction catalysed by transition metals of a compound of formula (VIII):

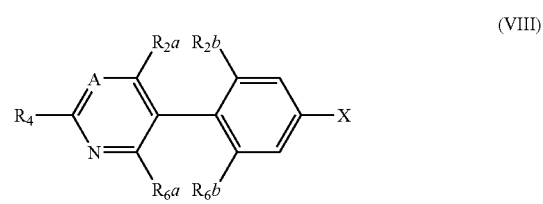

wherein X is a replaceable substituent with a compound of the formula (IX);

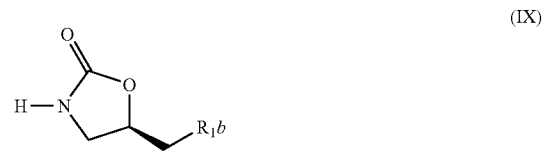

or (d(ii)) by reaction of a compound of formula (X):

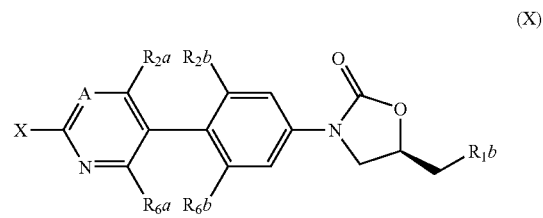

X is a replaceable substituent with a compound of the formula (XI):

T-H  (XI)

wherein T-H is an amine $R_7R_8NH$, an alcohol $R_{10}OH$, or an azole with an available ring-NH group to give compounds (XIIa), (XIIb), or (XIIc) wherein A is nitrogen or C—$R_3$a and A' is nitrogen or carbon optionally substituted with one or more groups R1a;

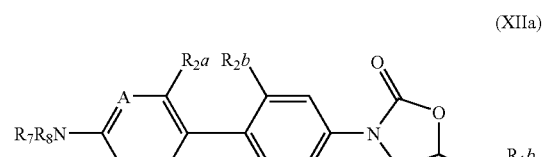

(XIIa)

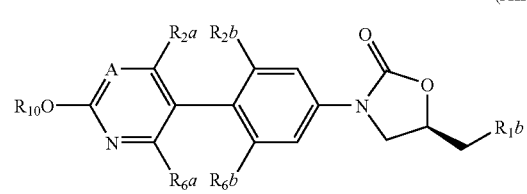

(XIIb)

-continued

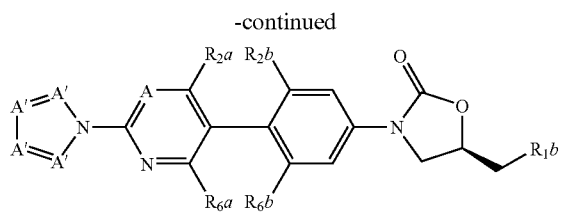

(e) reacting a compound of formula (XIII):

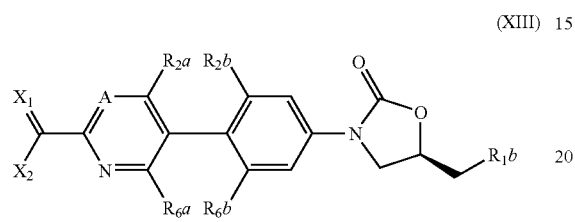
(XIII)

wherein $X_1$ and $X_2$ here are independently optionally substituted heteroatoms drawn in combination from O, N, and S such that $C(X_1)X_2$ constitutes a substituent that is a carboxylic acid derivative substituent with a compound of the formula (XIV) and $X_3$ and $X_4$ are independently optionally substituted heteroatoms drawn in combination from O, N, and S:

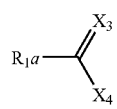
(XIV)

and wherein one of $C(X_1)X_2$ and $C(X_3)X_4$ constitutes an optionally substituted hydrazide, thiohydrazide, or amidrazone, hydroximidate, or hydroxamidine and the other one of $C(X_1)X_2$ and $C(X_3)X_4$ constitutes an optionally substituted acylating, thioacylating, or imidoylating agent such that $C(X_1)X_2$ and $C(X_3)X_4$ may be condensed together to form a 1,2,4-heteroatom 5-membered heterocycle containing 3 heteroatoms drawn in combination from 0, N, and S;

(e(i)) by reaction of a compound of formula (XV):

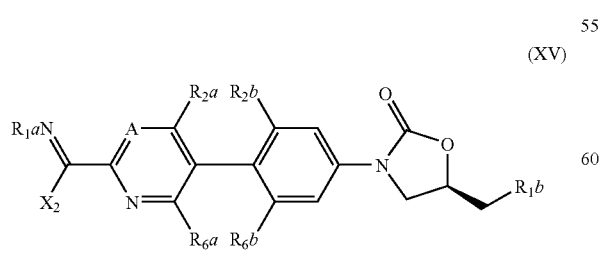
(XV)

wherein X2 is a displaceable group with a source of azide anion to give a tetrazole (XVI);

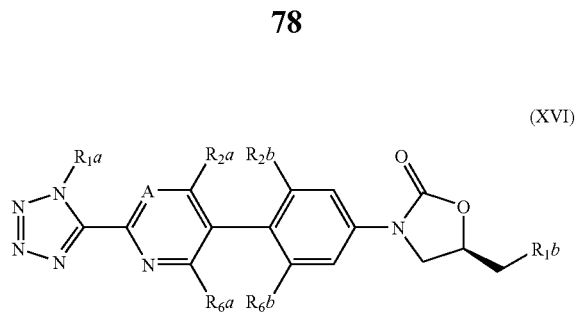
(XVI)

or nitriles of formula (XVII)

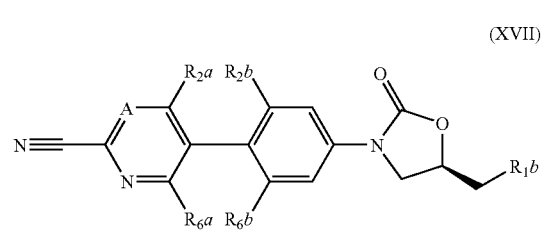
(XVII)

may be reacted directly with azides to give tetrazoles (XVI, R1a=H) that are subsequently alkylated with groups R1a≠H to give tetrazoles (XVIIIa) and (XVIIIb);

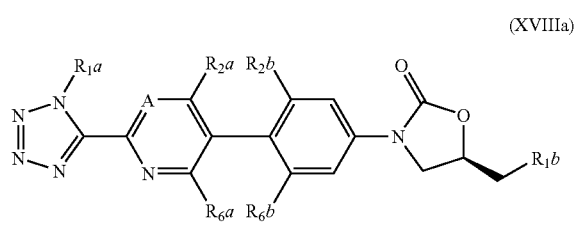
(XVIIIa)

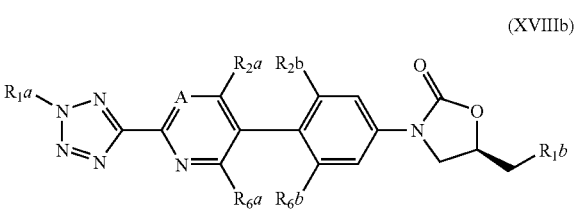
(XVIIIb)

(f) by a compound of formula (XIX):

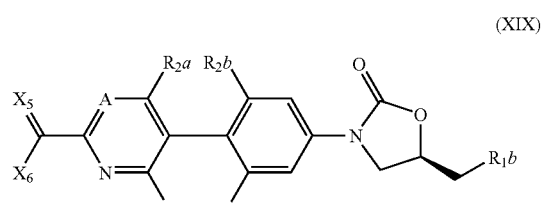
(XIX)

with a compound of the formula (XX):

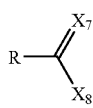

(XX)

wherein one of C(X$_5$)X$_6$ and C(X$_7$)X$_8$ constitutes an optionally substituted alpha-(leaving-group-substituted)keton wherein the leaving group is a halo-group or an (alkyl or aryl)-sulfonyloxy-group, and the other one of C(X$_5$)X$_6$ and C(X$_7$)X$_8$ constitutes an optionally substituted amide, thioamide, or amidine, such that C(X$_5$)X$_6$ and C(X$_7$)X$_8$ are groups that may be condensed together to form a 1,3-heteroatom 5-membered heterocycle containing 2 heteroatoms drawn in combination from O, N, and S;

(g) for HET as optionally substituted 1,2,3-triazoles, compounds of the formula (I), by cycloaddition via the azide to acetylenes, or to acetylene equivalents optionally substituted cylcohexa-1,4-dienes or optionally substituted ethylenes bearing eliminatable substituents;

(h) for HET as 4-substituted 1,2,3-triazole compounds of formula (I), by reacting aminomethyloxazolidinones with 1,1-dihaloketone sulfonylhydrazones;

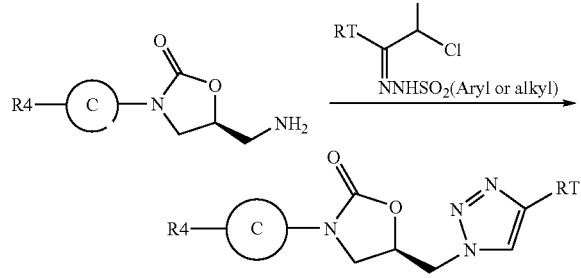

(i) for HET as 4-substituted 1,2,3-triazole compounds of formula (I), by reacting azidomethyl oxazolidinones with terminal alkynes using Cu(I) to give 4-substituted 1,2,3-triazoles.

12. A process for the preparation of a compound of formula (I) as claimed in claim 1 or pharmaceutically acceptable salts or in-vivo hydrolysable esters thereof, wherein HET-1 is 4-halogenated 1,2,3-triazole comprising reacting azidomethyl oxazolidinones with halovinylsulfonyl chlorides at a temperature between 0° C. and 100° C. either neat or in an inert diluent

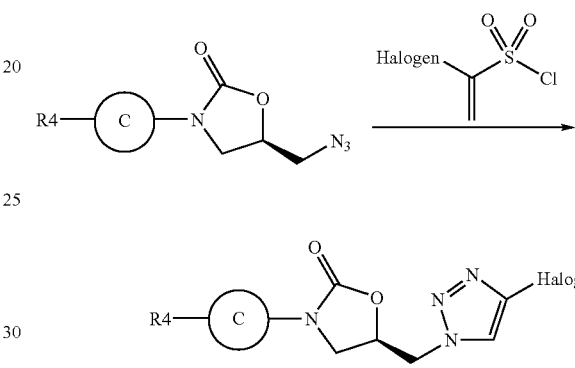

13. A process according to claim 12, wherein the halovinylsulfonyl chloride is 1-chloro-1-ethenesulfonyl chloride.

14. The process of claim 11, wherein in process (e), the 1,2,4-heteroatom 5-membered heterocycle is a thiadiazole.

15. The process of claim 11, wherein in process (g), the eliminatable substituent is arylsulfonyl.

* * * * *